US011577050B2

(12) United States Patent
Kanemasa et al.

(10) Patent No.: US 11,577,050 B2
(45) Date of Patent: *Feb. 14, 2023

(54) MEDICAL DEVICE

(71) Applicant: SUMITOMO BAKELITE CO., LTD., Shinagawa-ku (JP)

(72) Inventors: Kenichi Kanemasa, Akita (JP); Iji Onozuka, Akita (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 237 days.

This patent is subject to a terminal disclaimer.

(21) Appl. No.: 16/624,604

(22) PCT Filed: Aug. 2, 2018

(86) PCT No.: PCT/JP2018/029023
§ 371 (c)(1),
(2) Date: Dec. 19, 2019

(87) PCT Pub. No.: WO2019/026995
PCT Pub. Date: Feb. 7, 2019

(65) Prior Publication Data
US 2020/0121893 A1 Apr. 23, 2020

(30) Foreign Application Priority Data

Aug. 2, 2017 (JP) .............. JP2017-150210
Jan. 31, 2018 (JP) .............. JP2018-015534
Jan. 31, 2018 (JP) .............. JP2018-015535

(51) Int. Cl.
A61M 25/01 (2006.01)
A61M 25/00 (2006.01)

(52) U.S. Cl.
CPC .... A61M 25/0147 (2013.01); A61M 25/0136 (2013.01); A61M 25/005 (2013.01);
(Continued)

(58) Field of Classification Search
CPC .......... A61M 25/0147; A61M 25/0136; A61M 25/005; A61M 25/0138; A61M 2025/015;
(Continued)

(56) References Cited

U.S. PATENT DOCUMENTS 5,413,107 A * 5/1995 Oakley et al. .... A61M 25/0147
600/463
2003/0109778 A1* 6/2003 Rashidi ............. A61B 18/1492
606/41

(Continued)

FOREIGN PATENT DOCUMENTS

CN 103156686 A 6/2013
CN 104883945 A 9/2015

(Continued)

OTHER PUBLICATIONS

International Search Report dated Oct. 30, 2018 in PCT/JP2018/029023 filed on Aug. 2, 2018, 4 pages.

(Continued)

Primary Examiner — Shefali D Patel
(74) Attorney, Agent, or Firm — Oblon, McClelland, Maier & Neustadt, L.L.P.

(57) ABSTRACT

A medical device includes an elongated medical device body; a first operating line and a second operating line inserted in an axial direction of the medical device body; and a bending operating part for performing a bending operation of a distal end part of the medical device body by pulling the first and second operating lines, at an intermediate part and a proximal end part in the axial direction of the medical device body, the first and second operating lines extending in parallel so as to be spaced apart from each other in a circumferential direction of the medical device body, and at the distal end part in the axial direction of the medical device body, the first and second operating lines being curved and joined together so as to approach each other in the circum- (Continued)

ferential direction of the medical device body gradually toward a distal end side.

36 Claims, 22 Drawing Sheets

(52) U.S. Cl.
CPC ..... *A61M 25/0108* (2013.01); *A61M 25/0138* (2013.01); *A61M 2025/015* (2013.01)

(58) Field of Classification Search
CPC .............. A61M 25/0133; A61B 1/0057; A61B 1/0052; A61B 1/0051
See application file for complete search history.

(56) References Cited

U.S. PATENT DOCUMENTS

| | | | |
|---|---|---|---|
| 2004/0059288 A1* | 3/2004 | Webler .............. | A61M 25/0147 604/95.04 |
| 2006/0100640 A1* | 5/2006 | Bolduc .............. | A61M 25/0147 606/108 |
| 2006/0167467 A1 | 7/2006 | Rourke | |
| 2006/0252993 A1* | 11/2006 | Freed et al. ...... | A61M 25/0147 600/146 |
| 2008/0312506 A1* | 12/2008 | Spivey et al. .... | A61M 25/0147 600/149 |
| 2015/0202409 A1* | 7/2015 | Kanemasa ........ | A61M 25/0147 604/95.04 |
| 2016/0158497 A1* | 6/2016 | Tran .................. | A61M 25/0071 604/95.04 |
| 2016/0206853 A1* | 7/2016 | Bolduc et al. .... | A61M 25/0147 |
| 2017/0156711 A1* | 6/2017 | Jogasaki et al. ............................. A61M 2025/015 |

FOREIGN PATENT DOCUMENTS

| | | |
|---|---|---|
| EP | 2 604 174 A1 | 6/2013 |
| JP | 2011-251068 A1 | 12/2011 |
| JP | 2013-48711 A | 3/2013 |
| JP | 2016-518203 A | 6/2016 |
| WO | WO 2014/093457 A1 | 6/2014 |
| WO | WO 2014/184665 A2 | 11/2014 |

OTHER PUBLICATIONS

International Search Report dated Oct. 30, 2018 in PCT/JP2018/029101 filed on Aug. 2, 2018 (with English translation), 2 pages.

* cited by examiner

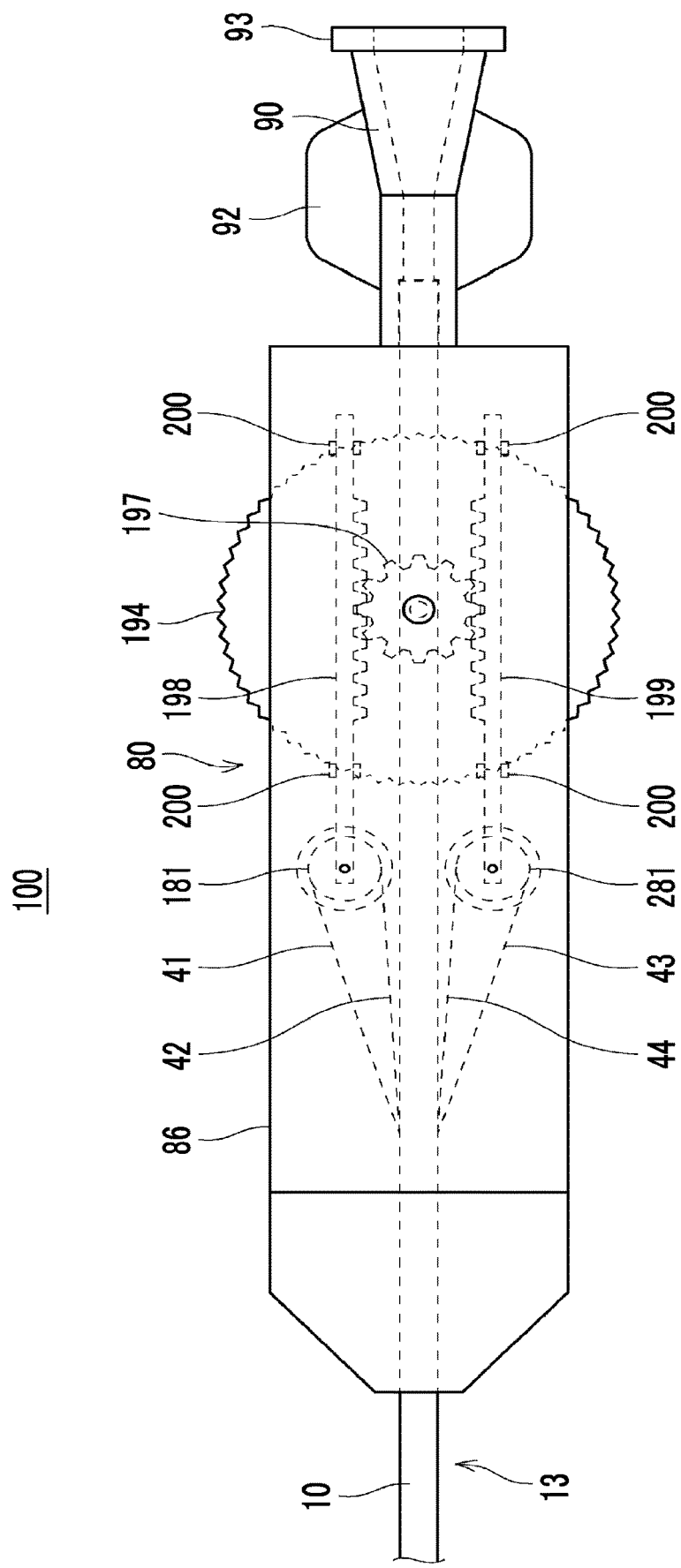

MEDICAL DEVICE

TECHNICAL FIELD

The present invention relates to a medical device.

The present application is a National Stage Application of PCT/JP2018/029023, filed Aug. 2, 2018, which is based on and claims the benefit of priority to Japanese Patent Application No. 2017-150210, filed Aug. 2, 2017, Japanese Patent Application No. 2018-015534, filed Jan. 31, 2018, and Japanese Patent Application No. 2018-015535, filed Jan. 31, 2018, the contents of which are incorporated herein by reference.

BACKGROUND ART

As an elongated medical device, such as a catheter capable of bending a distal end part, a type having operating lines is known (for example, Patent Document 1).

In the catheter of Patent Document 1, a plurality of hollow tubes are disposed around a central lumen, and operating lines are respectively inserted through the two hollow tubes that face each other via the central lumen. In the catheter of this document, distal ends of the operating lines are fixed to the distal end part of the catheter. The catheter of this document is configured to bend rear ends of the operating lines. Accordingly, the distal end part of the catheter can be bent by selecting and pulling an operating line.

CITATION LIST

Patent Literature

[Patent Document 1] Japanese Unexamined Patent Application, First Publication No. 2013-48711

SUMMARY OF INVENTION

Technical Problem

However, in the catheter of Patent Document 1, when the distal end part is further bent after passing through a body cavity, such as a curved blood vessel, the distal end part can be easily bent in an inward direction of the curve.

However, the distal end part is not easily bent in an outward direction. This is because, if an operating line located on an out-course side of the curve is pulled to bend a distal end of the catheter in the outward direction, the catheter rotates around the axis of the catheter within the curved blood vessel in a direction in which the path of the operating line to be pulled becomes short.

The invention has been made in view of the above problem, and provides a medical device, such as a catheter having a structure capable of more reliably bending the distal end part in a desired direction.

Additionally, in the medical device, such as a catheter, operability according to various needs is required, and there is room for improvements in the technique of Patent Document 1 from this viewpoint.

The invention has been made in view of the above problems, and provides a medical device, such as a catheter having a structure capable of suitably realizing operability according to various needs.

Solution to Problem

The invention provides a medical device including an elongated medical device body; a first operating line and a second operating line that are inserted in an axial direction of the medical device body; and a bending operating part for performing a bending operation of a distal end part of the medical device body by pulling the first operating line and the second operating line, at an intermediate part and a proximal end part in the axial direction of the medical device body, the first operating line and the second operating line extending in parallel so as to be spaced apart from each other in a circumferential direction of the medical device body, and at a distal end part in the axial direction of the medical device body, a first operating line and a second operating line being curved and joined together so as to approach each other in the circumferential direction of the medical device body gradually toward a distal end side.

Additionally, the invention provides an elongated medical device body; a first operating line and a second operating line that are inserted in an axial direction of the medical device body; and a bending operating part for performing a bending operation of a distal end part of the medical device body by pulling the first operating line and the second operating line, the bending operating part including a rotating member that is rotatably journaled and to which a proximal end part of the first operating line and a proximal end part of the second operating line are fixed, a moving mechanism that moves the rotating member in a pulling direction in which the first operating line and the second operating line are pulled, and an opposite direction opposite to the pulling direction, and an operation receiving part that operates in response to a user's operation, and the rotating member moves in the pulling direction and the opposite direction as power of the operation receiving part is transmitted to the rotating member via the moving mechanism.

Advantageous Effects of Invention

According to the invention, it is possible to more reliably bend the distal end part in a desired direction. Additionally, according to the invention, it is possible to preferably realize operability according to various needs.

BRIEF DESCRIPTION OF DRAWINGS

FIG. 22 is a plan view showing a bending operating part and a portion in the vicinity thereof in a medical device related to Embodiments 1-7 and 2-7.

DESCRIPTION OF EMBODIMENTS

Hereinafter, embodiments of the invention will be described with reference to the drawings. In addition, in all the drawings, the same components will be designated by the same reference signs, and the detailed description thereof will be omitted.

Various components of medical devices related to the present embodiments do not need to be individually independent, and it is allowed that a plurality of components are formed as one member, one component is formed by a plurality of members, a certain component is a portion of another component, a portion of a certain component and a portion of another component duplicate overlap each other, and the like.

Terms used when describing the embodiments of the invention are defined as follows unless otherwise noted.

In the description of the embodiments, there are cases where terms, such as a distal end part and a proximal end part, are used. The distal end part refers to a predetermined length region including an end (distal end) on an insertion distal end side of a medical device in respective units of the medical device. Additionally, the proximal end part refers to a predetermined length region including an end (proximal end) on a proximal end side of the medical device in respective units of the medical device.

Additionally, an axis refers to a central axis along a longitudinal direction of a medical device body.

The longitudinal section of the medical device refers to a section obtained by cutting the medical device along the axis. The cross-section of the medical device refers to a cross-section obtained by cutting the medical device in a plane orthogonal to the axis.

Embodiment 1-1

First, Embodiment 1-1 will be described with reference to FIG. 1 to FIG. 8(*b*).

Figure 1:
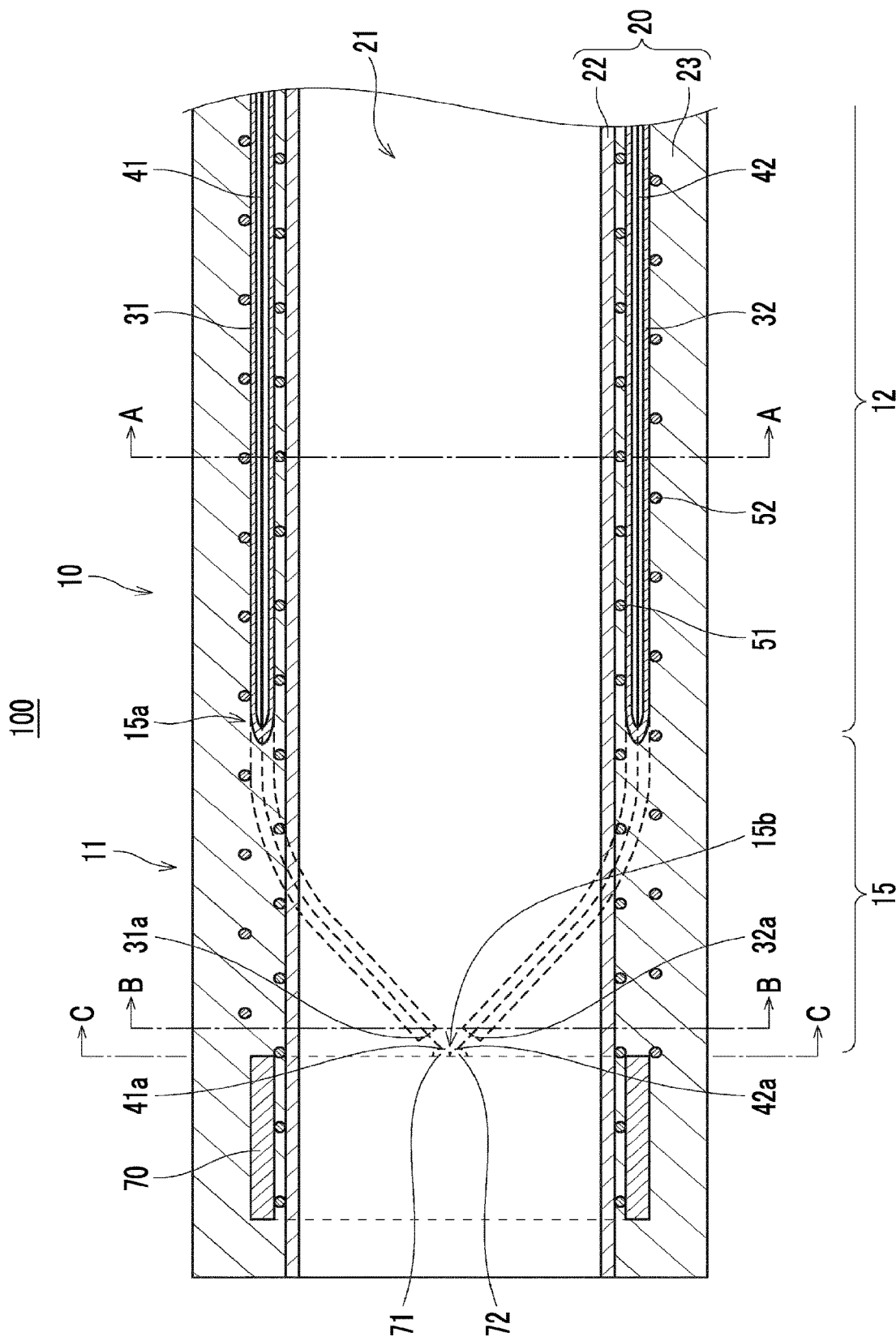
FIG. 1 is a longitudinal sectional view showing a portion on a distal end side in a medical device body of a medical device related to Embodiments 1-1 and 2-1.
Figure 2:
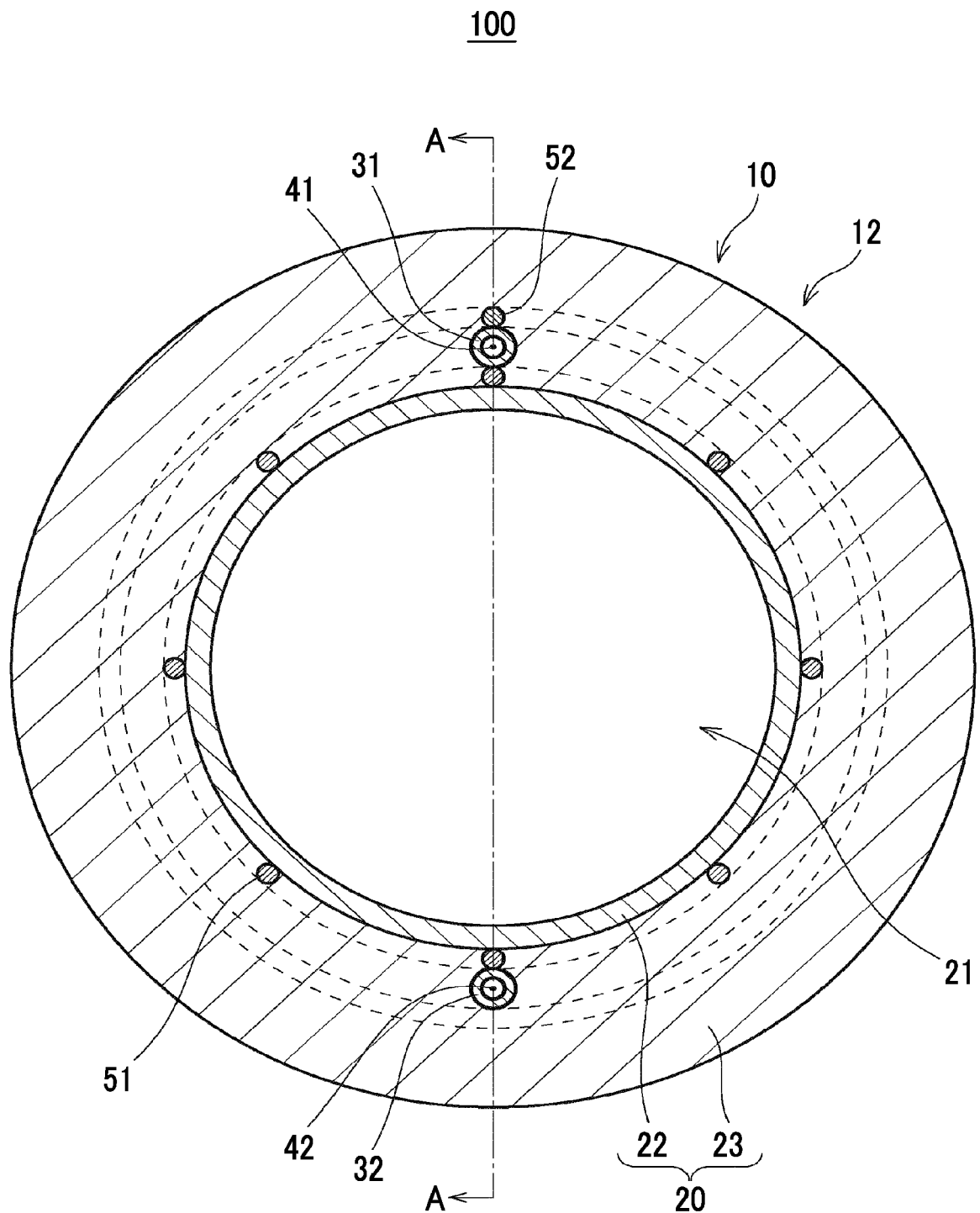
FIG. 2 is a cross-sectional view of the medical device body along line A-A of FIG. 1.

In addition, FIG. 1 is a sectional view along line A-A of FIG. 2.

Figure 4:
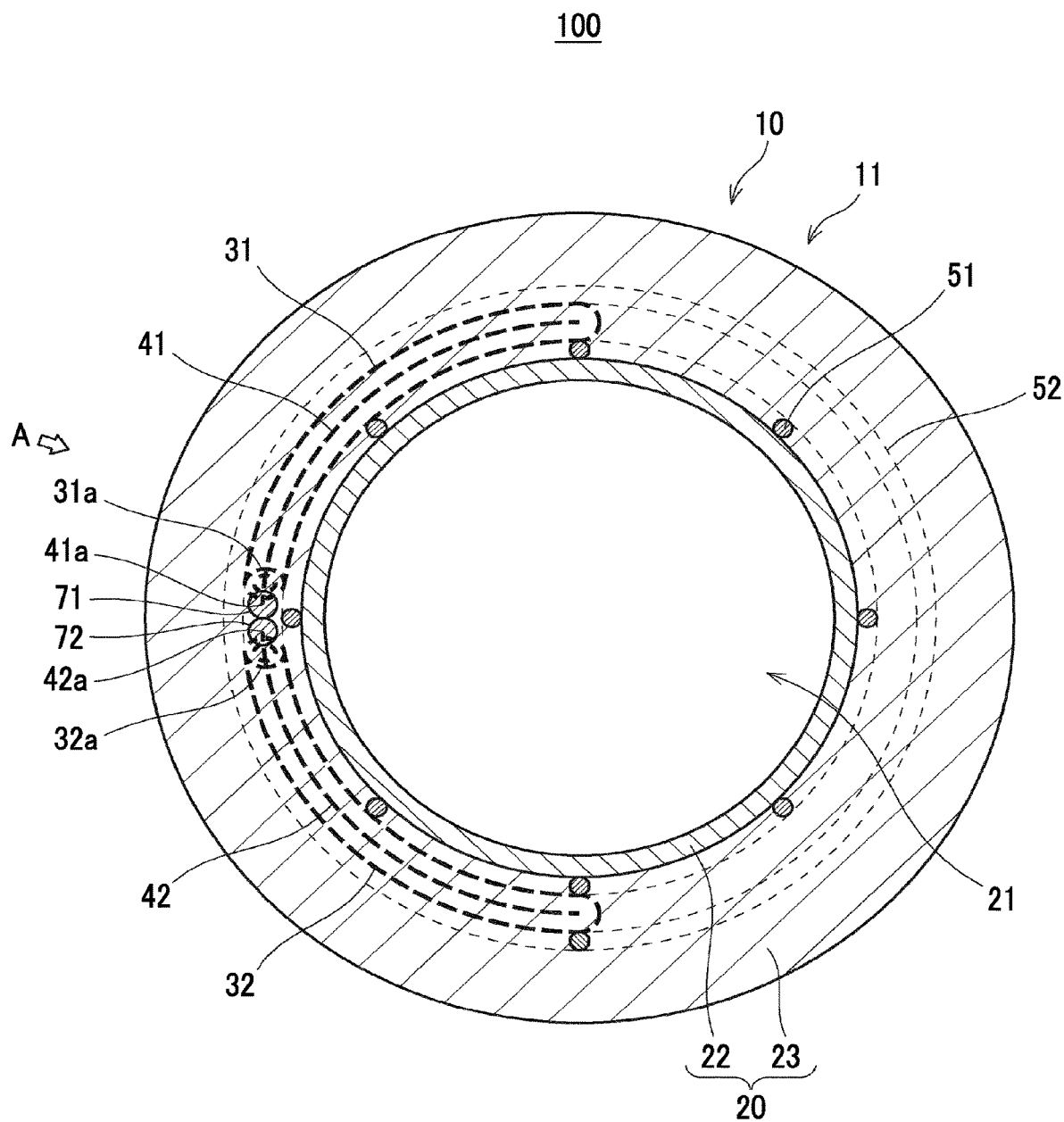
FIG. 4 is a cross-sectional view of the medical device body along line C-C of FIG. 1.
Figure 5:
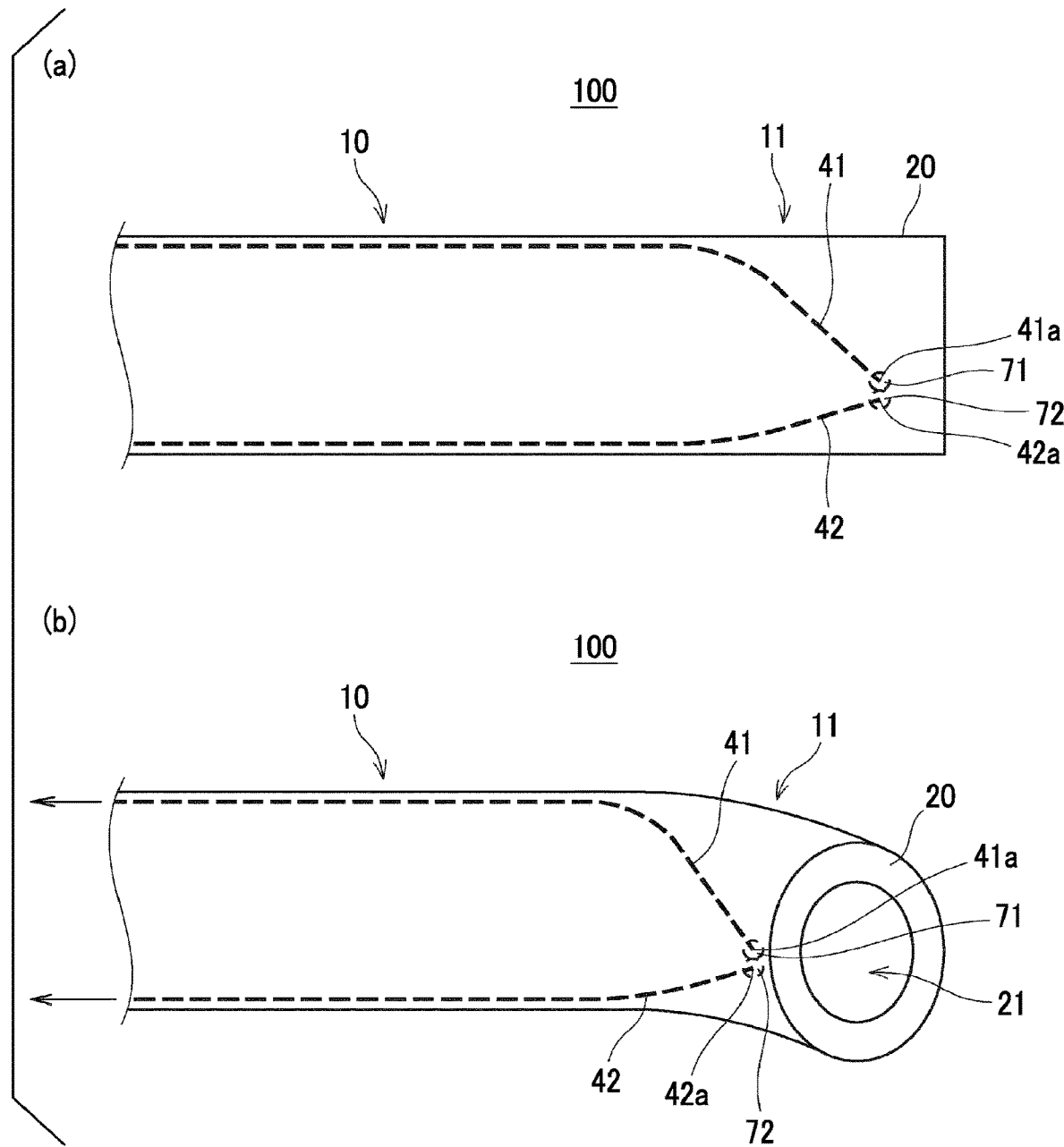
FIG. 5(a) and FIG. 5(b) are schematic views for showing the bending motion of a distal end part of the medical device body of the medical device related to Embodiments 1-1 and 2-1.

FIG. 5(*a*) and FIG. 5(*b*) are schematic views for showing a bending motion when a distal end part 11 of a medical device body 10 is seen in the direction of arrow A of FIG. 4, FIG. 5(*a*) shows a state before the bending, and FIG. 5(*b*) shows a bent state.

Figure 7:
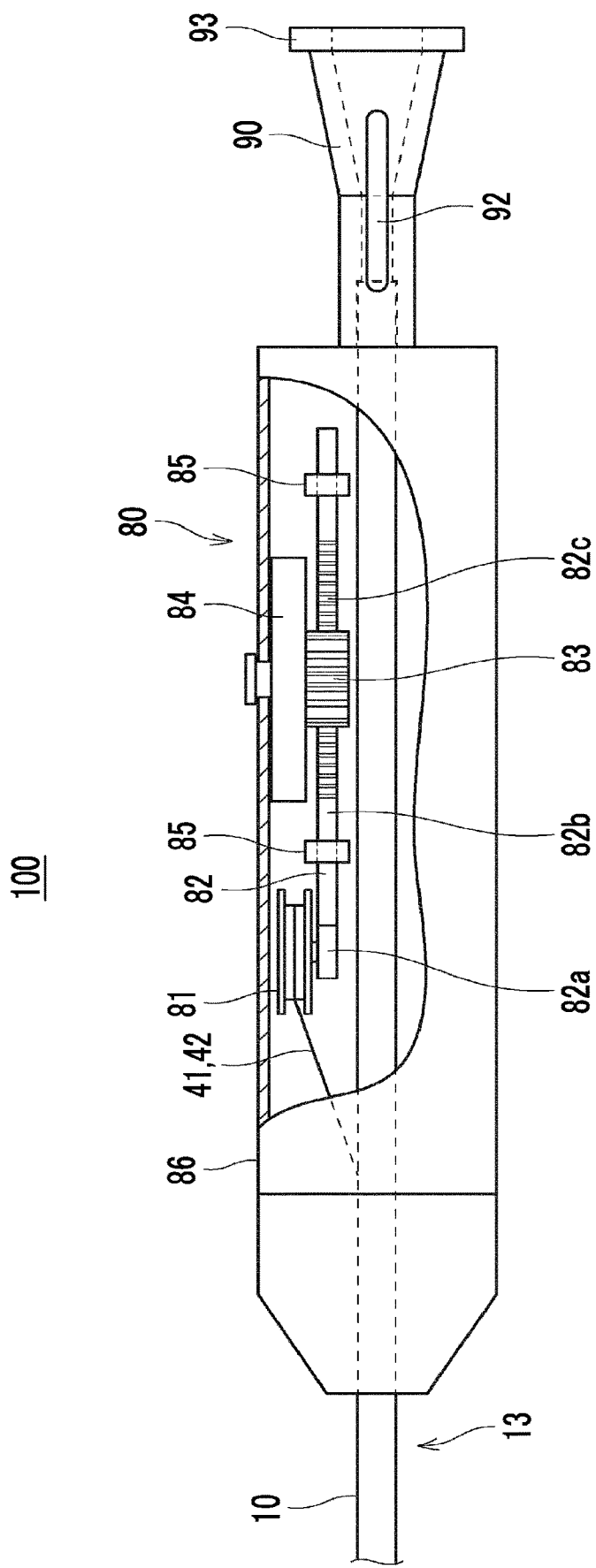
FIG. 7 is a side view showing the bending operating part and the portion in the vicinity thereof in the medical device related to Embodiments 1-1 and 2-1.

In FIG. 7, a housing 86 of a bending operating part 80 is broken partially to show the internal structure of the housing 86.

Figure 8:
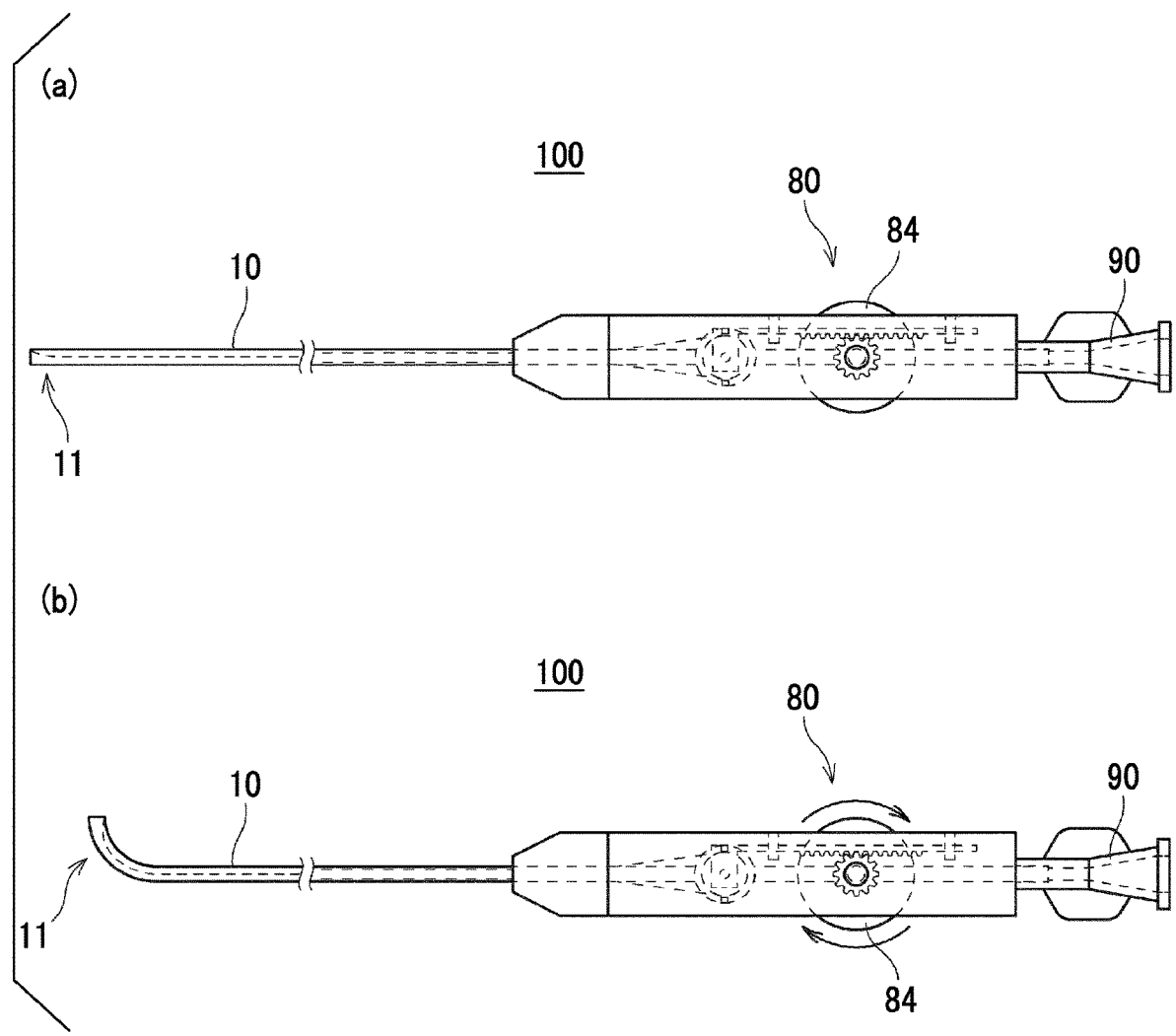
FIG. 8(a) is an overall view of the medical device related to Embodiments 1-1 and 2-1.
FIG. 8(b) is an overall view showing a state where the distal end part of the medical device body of the medical device related to Embodiments 1-1 and 2-1 is bent to one side.

In FIG. 8(*a*) and FIG. 8(*b*), a middle portion of the medical device body 10 in the longitudinal direction is broken and omitted. In the medical device body 10 shown in FIG. 8(*a*) and FIG. 8(*b*), a portion closer to a proximal end side than the omitted portion and a portion closer to the distal end side than the omitted portion have rotational phases around the axis of the medical device body 10 that are different from each other by 90 degrees.

As shown in any of FIG. 1 to FIG. 8(*b*), a medical device 100 related to the present embodiment includes the elongated medical device body 10, a first operating line 41 and a second operating line 42 that are inserted in an axial direction of the medical device body 10, and the bending operating part 80 (FIG. 6, FIG. 7) for performing the bending operation of the distal end part 11 of the medical device body 10 by pulling the first operating line 41 and the second operating line 42.

At an intermediate part 12 and a proximal end part 13 (FIG. 6, FIG. 7) in the axial direction of the medical device body 10, the first operating line 41 and the second operating line 42 extend in parallel so as to be spaced apart from each other in a circumferential direction of the medical device body 10.

At the distal end part 11 of the medical device body 10 in the axial direction, the first operating line 41 and the second operating line 42 are curved and joined together so as to approach each other in the circumferential direction of the medical device body 10 gradually toward the distal end side.

Here, the fact that the first operating line 41 and the second operating line 42 are close to each other means that a distal end 41*a* of the first operating line 41 and a distal end 42*a* of the second operating line 42 are joined together. It is preferable that the distal end 41*a* of the first operating line 41 and the distal end 42*a* of the second operating line 42 are close to each other at a distance smaller than the thickness of a resin tube 20 to be described below.

According to the present embodiment, the distal end part 11 of the medical device body 10 can be bent as shown in FIG. 5(a) and FIG. 5(b) by pulling both of the first operating line 41 and the second operating line 42. In this case, the load of pulling the distal end part 11 of the medical device body 10 with the first operating line 41 and the load of pulling the distal end part 11 with the second operating line 42 can be balanced with each other. Therefore, occurrence of a phenomenon in which the medical device body 10 rotates around the axis such that the first operating line 41 or the second operating line 42 tends to take a shortcut can be limited.

Thus, even when the distal end part 11 is further bent after the medical device body 10 passes through a body cavity, such as a curved blood vessel, it is possible to more reliably bend the distal end part 11 in a desired direction.

In addition, as in the case of the present embodiment, in a case where the number of operating lines provided in the medical device 100 is two and these operating lines are joined together, a direction in which the distal end part 11 can be bent by pulling the operating line is one direction.

The medical device 100 is, typically, a catheter.

The medical device body 10 includes the resin tube 20 of which an inner cavity is as a lumen 21.

In the case of the present embodiment, the resin tube 20 has a layer structure including a hollow tubular inner layer 22 of which an inner cavity is the lumen 21, and a hollow tubular outer layer 23 that is formed coaxially with the inner layer 22 and at an outer periphery of the inner layer 22. The inner layer 22 and the outer layer 23 are respectively made of resin materials. An inner peripheral surface of the outer layer 23 is joined to an outer peripheral surface of the inner layer 22.

A resin material constituting the inner layer 22 and a resin material constituting the outer layer 23 may be different from each other, or may be the same as each other.

A hydrophilic coat may be formed on an outer surface layer of the medical device body 10 as necessary.

The lumen 21 is continuously formed from a distal end of the medical device body 10 to a proximal end thereof, and opens at the distal end and the proximal end of the medical device body 10, respectively.

The medical device body 10 further includes a first hollow tube 31 and a second hollow tube 32 that are buried in the resin tube 20. The first operating line 41 is inserted through the first hollow tube 31, and the second operating line 42 is inserted through the second hollow tube 32.

The first hollow tube 31 and the second hollow tube 32 are respectively sublumen tubes, and inner cavities of these sublumen tubes are sublumens. That is, the operating lines (the first operating line 41, the second operating line 42) are respectively inserted through the sublumens.

The internal diameters of the first hollow tube 31 and the second hollow tube 32 are smaller than the internal diameter of the lumen 21.

The first operating line 41 and the second operating line 42 are respectively constituted of thin lines, such as metal or resin.

In addition, in the case of the present embodiment, the first hollow tube 31 and the second hollow tube 32 are disposed avoiding a position on an in-course side when the distal end part 11 of the medical device body 10 is bent. Therefore, the bending of the distal end part 11 can be easily performed. Since the first hollow tube 31 and the second hollow tube 32 are spaced apart from the in-course side, particularly on a further proximal end side in the distal end part 11, the bending becomes easy.

At the distal end part 11 of the medical device body 10, the first hollow tube 31 and the second hollow tube 32 are curved so as to approach each other in the circumferential direction of the medical device body 10 gradually toward the distal end side. Accordingly, the first operating line 41 within the first hollow tube 31 and the second operating line 42 within the second hollow tube 32 are curved so as to approach each other in the circumferential direction of the medical device body 10 gradually toward the distal end side.

In addition, the first hollow tube 31 and the second hollow tube 32 do not intersect each other. Additionally, the first operating line 41 and the second operating line 42 do not intersect each other.

In this way, the medical device body 10 is configured to include the resin tube 20 having the lumen 21, and the first hollow tube 31 and the second hollow tube 32 that are buried in the resin tube 20 and allows the first operating line 41 and the second operating line 42 to be respectively inserted therethrough. At the distal end part 11 of the medical device body 10 in the axial direction, the first hollow tube 31 and the second hollow tube 32 are curved so as to approach each other in the circumferential direction of the medical device body 10 gradually toward the distal end side.

In addition, a region where the first operating line 41 and the second operating line 42 approach each other in the circumferential direction of the medical device body 10 gradually toward the distal end side in the axial direction of the medical device body 10 is referred to as a curved region 15. A proximal end position 15a of the curved region 15 is a position where the first operating line 41 and the second operating line 42 starts to be curved toward each other, and a distal end position 15b of the curved region 15 is a position where the first operating line 41 and the second operating line 42 finishes being curved toward each other.

In the case of the present embodiment, the distal end position 15b of the curved region 15 is a position where the distal ends 41a and 42a of the first operating line 41 and the second operating line 42 are disposed, or a position in the vicinity thereof.

The distal end 41a of the first operating line 41 protrudes from a distal end 31a of the first hollow tube 31. Similarly, the distal end 42a of the second operating line 42 protrudes from a distal end 32a of the second hollow tube 32.

For example, the distal end 41a is located in the vicinity of the distal end 31a, and the distal end 42a is located in the vicinity of the distal end 32a.

The medical device body 10 includes, for example, a braid layer 51 buried in the resin tube 20. Accordingly, the medical device body 10 is reinforced by the braid layer 51. The braid layer 51 is configured by braiding two or more wires. The braid layer 51 is disposed, for example, around the inner layer 22.

In addition, the first hollow tube 31 and the second hollow tube 32 are disposed, for example, on a further radially outer side (at a position far from the axis of the medical device body 10) of the medical device body 10 than the braid layer 51.

The medical device body 10 further includes a winding wire 52 buried in the resin tube 20. The winding wire 52 is wound on a further radially outer side of the medical device body 10 than the braid layer 51, the first hollow tube 31, and the second hollow tube 32. For example, the winding wire 52 constrains the first hollow tube 31 and the second hollow tube 32 to the braid layer 51.

Figure 3:
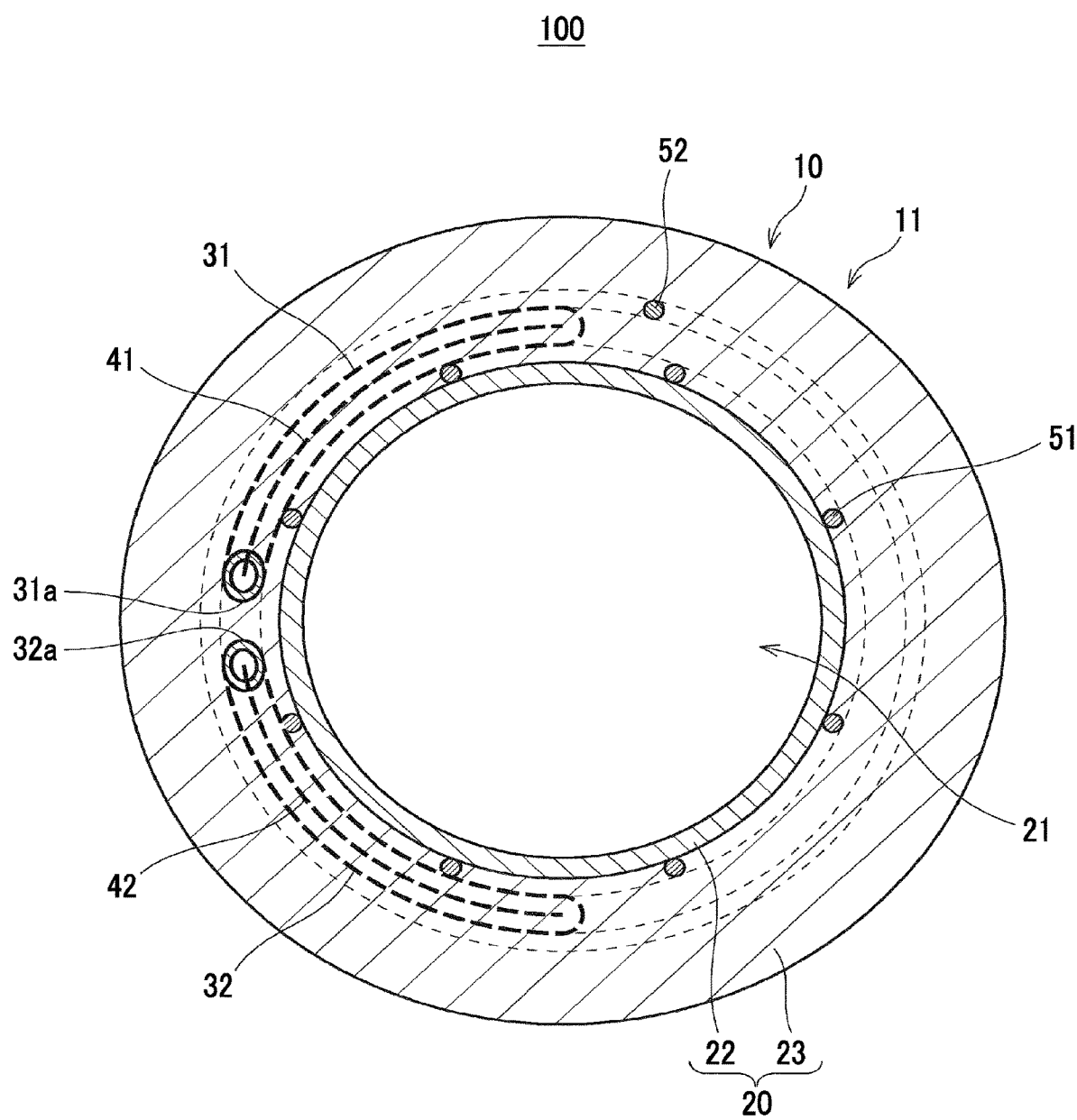
FIG. 3 is a cross-sectional view of the medical device body along line B-B of FIG. 1.

In the curved region 15, the first hollow tube 31 and the second hollow tube 32 are disposed along an outer periphery of the braid layer 51 (refer to FIG. 3 and FIG. 4).

In the curved region 15, the distance between the first hollow tube 31 and the second hollow tube 32 in the circumferential direction of the medical device body 10 decreases gradually toward the distal end side, and the distance between the first operating line 41 and the second operating line 42 in the circumferential direction of the medical device body 10 decreases gradually toward the distal end side.

In addition, the first hollow tube 31 and the second hollow tube 32 are deformed in a curved shape, for example, on a further distal end side than the proximal end position 15a of the curved region 15. The first hollow tube 31 and the second hollow tube 32 may be respectively fixed to at least one of the braid layer 51 or the inner layer 22 at the proximal end position 15a of the curved region 15, or a distal end of the winding wire 52 may be disposed at the proximal end position 15a of the curved region 15, and the first hollow tube 31 and the second hollow tube 32 may not be constrained by the winding wire 52 on a further distal end side than the proximal end position 15a.

At the intermediate part 12 and the proximal end part 13 in the axial direction of the medical device body 10, the first operating line 41 and the second operating line 42 are disposed at positions that face each other in the circumferential direction of the medical device body 10.

In the case of the present embodiment, for example, as shown in FIG. 2, at the intermediate part 12 of the medical device body 10, the first operating line 41 and the second operating line 42 face each other by 180 degrees in the circumferential direction of the medical device body 10 with the axis of the medical device body 10 as a reference. Similarly, even at the proximal end part 13 of the medical device body 10 and the proximal end position 15a of the curved region 15, the first operating line 41 and the second operating line 42 face each other by 180 degrees in the circumferential direction of the medical device body 10. That is, at the intermediate part 12, the proximal end part 13, and the proximal end position 15a of the curved region 15, the phase difference between the first operating line 41 and the second operating line 42 in the circumferential direction of the medical device body 10 is 180 degrees.

The phase difference between the first operating line 41 and the second operating line 42 in the circumferential direction of the medical device body 10 decreases gradually toward the distal end side in the curved region 15, and at the distal end position 15b of the curved region 15, for example, the phase difference is about 0. In the case of the present embodiment, the first operating line 41 and the second operating line 42 are rotated by 90 degrees in the circumferential direction of the medical device body 10 in the curved region 15.

However, the fact that the first operating line 41 and the second operating line 42 disposed at positions that face each other in the circumferential direction of the medical device body 10 is not limited to this example, and means that the first operating line 41 and the second operating line 42 are spaced apart from each other by 120 degrees or more in the circumferential direction of the medical device body 10.

Additionally, in the case of the present embodiment, at the intermediate part 12, the proximal end part 13, and the proximal end position 15a of the curved region 15 in of the medical device body 10, the first hollow tube 31 and the second hollow tube 32 face each other 180 degrees in the circumferential direction of the medical device body 10 with the axis of the medical device body 10 as a reference. That is, at the intermediate part 12, the proximal end part 13, and the proximal end position 15a of the curved region 15, the phase difference between the first hollow tube 31 and the second hollow tube 32 in the circumferential direction of the medical device body 10 is 180 degrees. The phase difference decreases gradually toward the distal end side in the curved region 15.

The distal end part 11 of the medical device body 10 is provided with a ring-shaped marker 70 made of a radiopaque metallic material.

The marker 70 is disposed coaxially with the lumen 21 and around the lumen 21.

The marker 70 is disposed, for example, around the braid layer 51.

The distal end 41a of the first operating line 41 is fixed to the marker 70 by a first fixing part 71 that is, for example, spot-shaped solder.

Similarly, the distal end 42a of the second operating line 42 is fixed to the marker 70 by the first fixing part 71 that is, for example, spot-shaped solder.

The first fixing part 71 and the second fixing part 72 are disposed, for example, at an end part of the marker 70 on the proximal end side.

In the case of the present embodiment, the distal end 41a of the first operating line 41 and the distal end 42a of the second operating line 42 are coupled to each other. That is, the distal ends of the first operating line 41 and the second operating line 42 are coupled to each other.

More specifically, the first fixing part 71 and the second fixing part 72 are adjacent to and in contact with each other. That is, the first fixing part 71 and the second fixing part 72 are integrated with each other.

In addition, the distal end 41a and the distal end 42a may be fixed to the marker 70 by a single fixing part.

Next, a hub 90 provided at a proximal end part of the medical device body 10 will be described with reference to FIGS. 6 and 7.

The hub 90 has a coupling part 93 for inserting an injector (syringe), which is not shown, from a proximal end of the hub 90. A thread groove is formed at an outer periphery of the coupling part 93 so that the syringe can be detachably fixed. Two wing parts 92, which face each other via an axis of the hub 90, are provided at an outer periphery of the hub 90.

The proximal end part of the medical device body 10 is inserted into and fixed to a distal end part of the hub 90. Accordingly, the lumen 21 inside the medical device body 10 and an internal space of the hub 90 communicate with each other.

By rotating the wing parts 92 about the axis of the hub 90, a torque operation for rotating the entire medical device body 10 about an axis is possible.

The housing 86 of the bending operating part 80 to be described below is connected and fixed to a distal end side of the hub 90.

Next, the bending operating part 80 provided in the medical device 100 will be described with reference to FIGS. 6 and 7.

The medical device 100 includes the bending operating part 80 for performing the bending operation of the distal end part 11 of the medical device body 10 by pulling the first operating line 41 and the second operating line 42.

The bending operating part 80 is configured to include a rotating member 81 that is rotatably journaled and is engaged with the first operating line 41 and the second operating line 42, and to which a proximal end part of the first operating line 41 and a proximal end part of the second operating line 42 are fixed, and a moving mechanism that moves the rotating member 81 in a pulling direction in which the first operating line 41 and the second operating line 42 are pulled, and an opposite direction opposite to the pulling direction.

The rotating member 81 is, for example, a pulley.

Here, in the present specification, "a certain member is rotatable" includes not only an aspect in which the member is rotatable 360 degrees or more but also an aspect in which only oscillation in a predetermined angle range of less than 360 degrees is possible.

Figure 6:
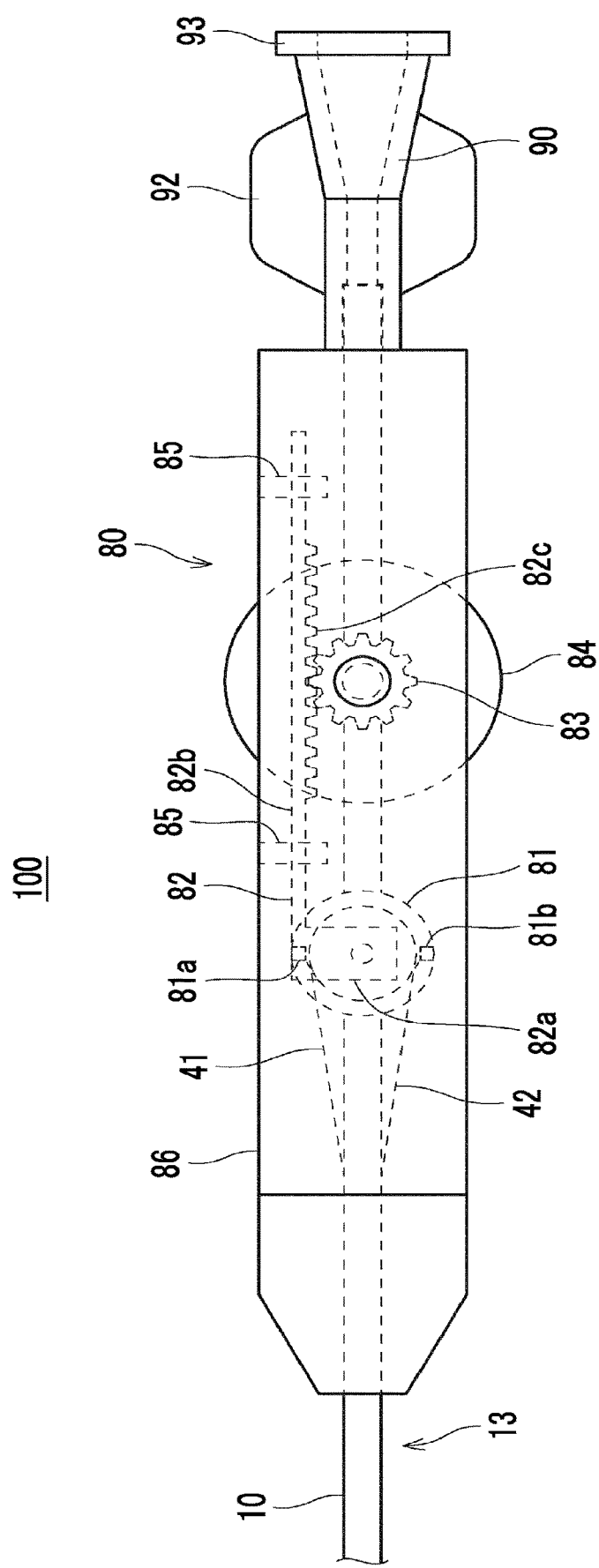
FIG. 6 is a plan view showing a bending operating part and a portion in the vicinity thereof in the medical device related to Embodiments 1-1 and 2-1.

As shown in FIG. 6, the rotating member 81 has an engaging part formed in a circular shape centered on a rotation center of the rotating member 81, and the first operating line 41 and the second operating line 42 are engaged with the engaging part. In addition, the engaging part of the rotating member 81 is not limited to the circular shape, and may have a circular shape.

In this way, the rotating member 81 has the engaging part that is engaged with the first operating line 41 and the second operating line, and the engaging part is formed in a circular shape or circular-arc shape centered on the rotation center of the rotating member 81.

The moving mechanism is configured to include a forward/backward movable member 82 and a pinion 83.

The forward/backward movable member 82 includes a holding part 82*a* that rotatably holds the rotating member 81, and a rod-shaped part 82*b* that extends from the holding part 82*a* to a proximal end side of the medical device body 10.

A rack part 82*c* is formed in the rod-shaped part 82*b*.

The bending operating part 80 further includes a housing 86 that is a body part of the bending operating part 80, a dial operating part 84 rotatably journaled to the housing 86, a pinion 83 provided integrally with the dial operating part 84, and a guide 85 (for example, a pair of front and rear guides 85) that is provided on an inner surface of the housing 86 to guide the rod-shaped part 82*b* in a longitudinal direction of the rod-shaped part 82*b*.

The proximal end part 13 of the medical device body 10 is guided to a proximal end side of the housing 86 through the inside of the housing 86, and is inserted into and fixed to the distal end part of the hub 90.

A rotating shaft of the dial operating part 84 extends in the direction orthogonal to an axis direction of the medical device body 10 within the housing 86.

The pinion 83 is formed integrally with the dial operating part 84 on one face side of the dial operating part 84, and is disposed coaxially with the rotating shaft of the dial operating part 84.

A gear at an outer periphery of the pinion 83 meshes with a gear of the rack part 82*c* of the forward/backward movable member 82.

At least a portion of the dial operating part 84 is exposed to the outside of the housing 86 so that an operation in which an operator who performs the operation of the medical device 100 rotates the dial operating part 84 can be performed from the outside of the housing 86.

The first operating line 41 and the second operating line 42 are delivered from the medical device body 10 within the housing 86.

The proximal end part of the first operating line 41 is wound around the rotating member 81, for example, by one and a half turns, and a proximal end of the first operating line 41 is fixed to the rotating member 81 by a first fixing part 81*a* (FIG. 6).

Similarly, the second operating line 42 is wound around the rotating member 81, for example, by one and a half turns, and a proximal end of the second operating line 42 is fixed to the rotating member 81 by a second fixing part 81*b* (FIG. 6).

A winding direction of the first operating line 41 and a winding direction of the second operating line 42 around the rotating member 81 are mutually opposite directions. For this reason, the rotational angle of the rotating member 81 is autonomously adjusted to an angle at which the tension of the first operating line 41 and the tension of the second operating line 42 are balanced with each other.

As an operator who performs the operation of the medical device 100 grips the housing 86 or the hub 90 to rotate the dial operating part 84, the pinion 83 integral with the dial operating part 84 rotates about an axis. Along with this, the forward/backward movable member 82 having the rack part 82*c* moves forward (moves to a distal end side of the medical device body 10) or moves backward (moves to the proximal end side of the medical device body 10) in the axial direction of the medical device body 10 relative to the housing 86.

In FIG. 6, by rotating the dial operating part 84 in the clockwise direction, the forward/backward movable member 82 and the rotating member 81 moves backward, and both of the first operating line 41 and the second operating line 42 are pulled to the proximal end side of the medical device body 10.

In this way, the bending operating part 80 includes an operation receiving part (dial operating part 84) that operates in response to the operation of a user (operator), and as the power of the operation receiving part to the rotating member 81 via the moving mechanism, the rotating member 81 is adapted to move in the pulling direction and the direction opposite to the pulling direction.

More specifically, as described above, the operation receiving part (dial operating part 84) is journaled in a rotationally operable manner, the moving mechanism includes the pinion 83 provided integrally and coaxially with the operation receiving part, and a rack member (forward/backward movable member 82) that moves forward and backward in an interlocking manner with the rotation of the pinion 83, and the rotating member 81 is journaled to the rack member.

In this way, the first operating line 41 and the second operating line 42 are pulled at a time by the operation on the bending operating part 80.

Here, "the first operating line 41 and the second operating line 42 are pulled at a time" means that a timing when both of the first operating line 41 and the second operating line 42 are pulled is present, and is not limited to timings when pulling is started by the first operating line 41 and the second operating line 42 being the same, and is not limited to timings when pulling is ended by the first operating line 41 and the second operating line 42 being the same.

For example, as shown in FIG. 8(*a*), when the distal end part 11 of the medical device body 10 has a linear shape, both of the first operating line 41 and the second operating line 42 are pulled to the proximal end side of the medical device body 10 if the dial operating part 84 is rotated in the clockwise direction in FIG. 8(*b*). Therefore, the distal end part 11 of the medical device body 10 is bent in one direction.

In addition, if the dial operating part 84 is rotated in the counterclockwise direction from the state of FIG. 8(*b*), the forward/backward movable member 82 and the rotating member 81 move forward, and the tension of the first operating line 41 and the second operating line 42 is released. Therefore, the distal end part 11 of the medical device body 10 is allowed to return linearly.

In this way, in the case of the present embodiment, the bending operating part 80 is configured to receive the operation performed by a user with a rotating mechanism (dial operating part 84) and convert a force applied to the rotating mechanism by this operation into a forward/backward movement in the axial direction of the medical device body 10 with a conversion mechanism constituted of the pinion 83 and the rack (rack part 82c).

Next, examples of the materials of the respective units of the medical device 100 will be described.

As the materials of the inner layer 22, for example, resin materials, such as polytetrafluoroethylene (PTFE), polyvinylidene fluoride (PVDF), and perfluoroalkoxy fluororesin (PFA), can be used.

As the materials of the outer layer 23, in addition to polyimide (PI), polyamide imide (PAI), and polyethylene terephthalate (PET), resin materials, such as polyethylene (PE), polyamide (PA), nylon elastomer, polyurethane (PU), ethylene-vinyl acetate resin (EVA), polyvinyl chloride (PVC), or polypropylene (PP), can be used.

As the materials of the first hollow tube 31 and the second hollow tube 32, for example, resin materials, such as polytetrafluoroethylene (PTFE), polyvinylidene fluoride (PVDF), and perfluoroalkoxy fluororesin (PFA), can be used.

Although metallic materials, such as stainless steel and tungsten, are preferable as the materials of the wire that constitutes the braid layer 51, the materials of the wire may be, for example, resin materials.

Although the metallic materials, such as stainless steel and tungsten, are preferable as the materials of the wire that constitutes the winding wire 52, the materials of the wire may be, for example, resin materials.

According to the medical device 100 related to Embodiment 1-1 as described above, the distal end part 11 of the medical device body 10 can be bent by pulling both of the first operating line 41 and the second operating line 42. In that case, a load for pulling the distal end part 11 of the medical device body 10 with the first operating line 41, and a load for pulling the distal end part 11 with the second operating line 42 can be balanced with each other. Therefore, the occurrence of the phenomenon in which the medical device body 10 rotates around the axis such that the first operating line 41 or the second operating line 42 tends to take a shortcut can be limited.

Therefore, it is possible to more reliably bend the distal end part 11 of the medical device body 10 in a desired direction.

Embodiment 1-2

Figure 9:
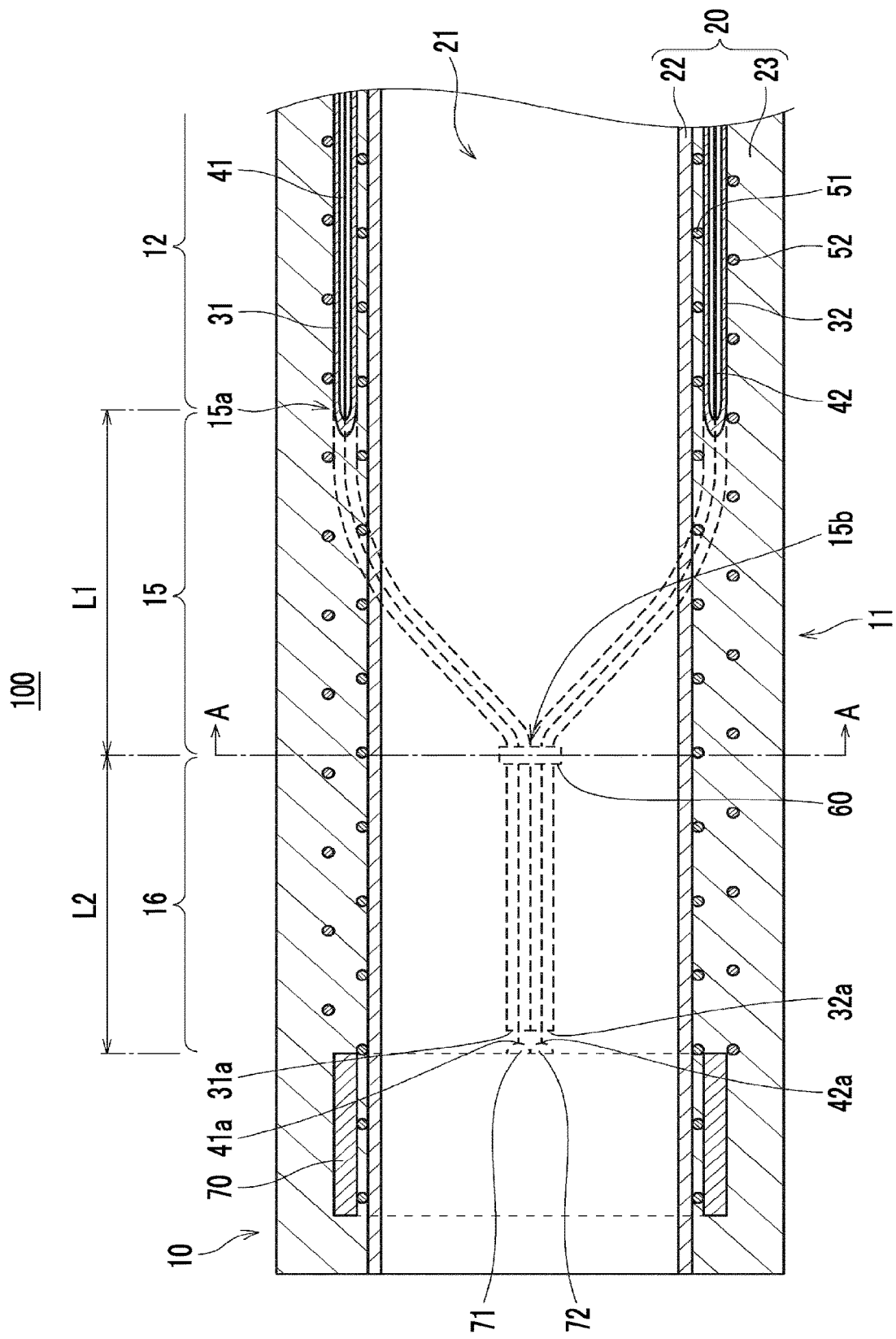
FIG. 9 is a longitudinal sectional view showing a portion on a distal end side in a medical device body of a medical device related to Embodiment 1-2 and 2-2.

Next, the medical device 100 related to Embodiment 1-2 will be described with reference to FIG. 9 to FIG. 11(*b*).

Figure 10:
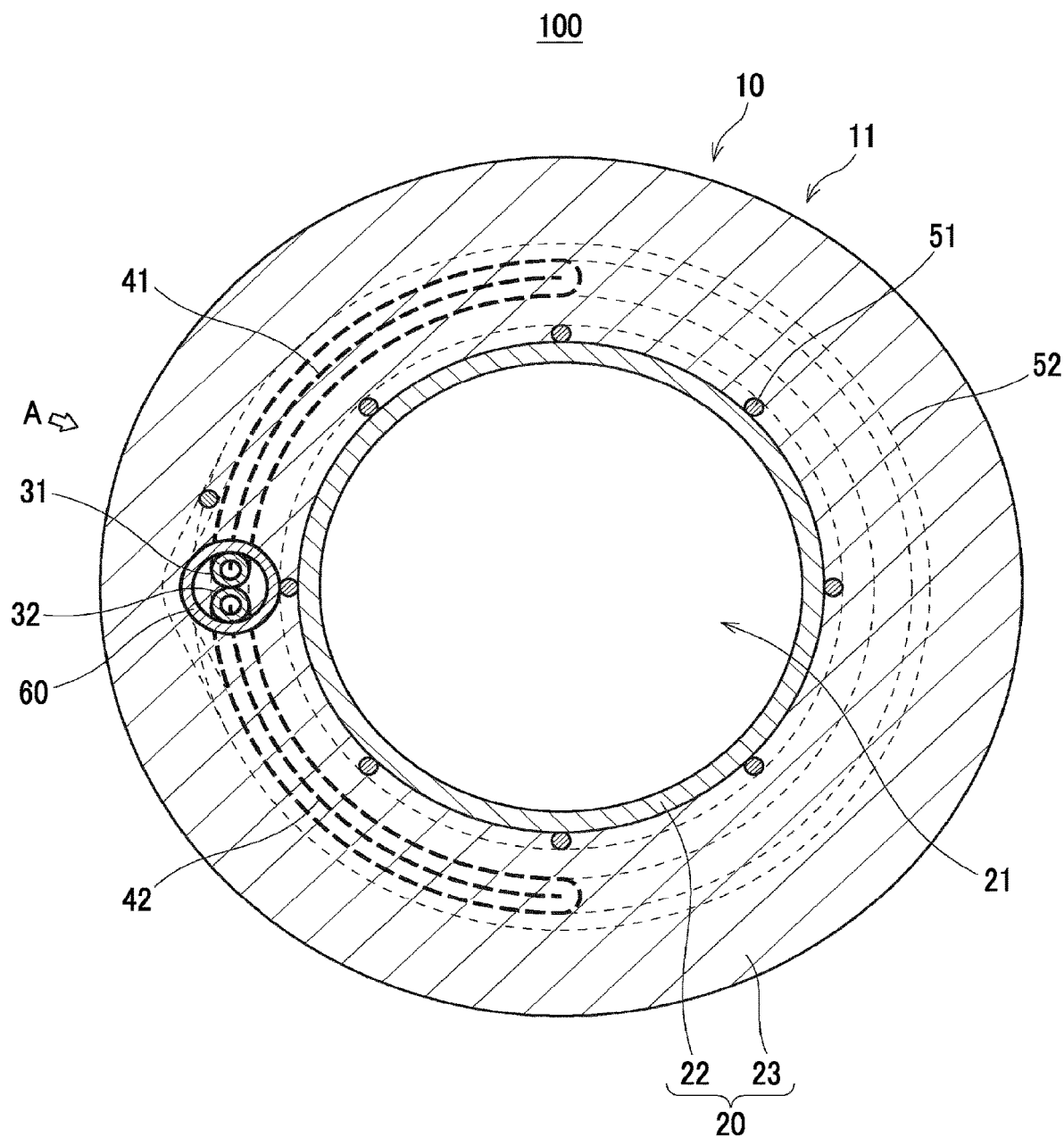
FIG. 10 is a cross-sectional view of the medical device body along line A-A of FIG. 9.
Figure 11:
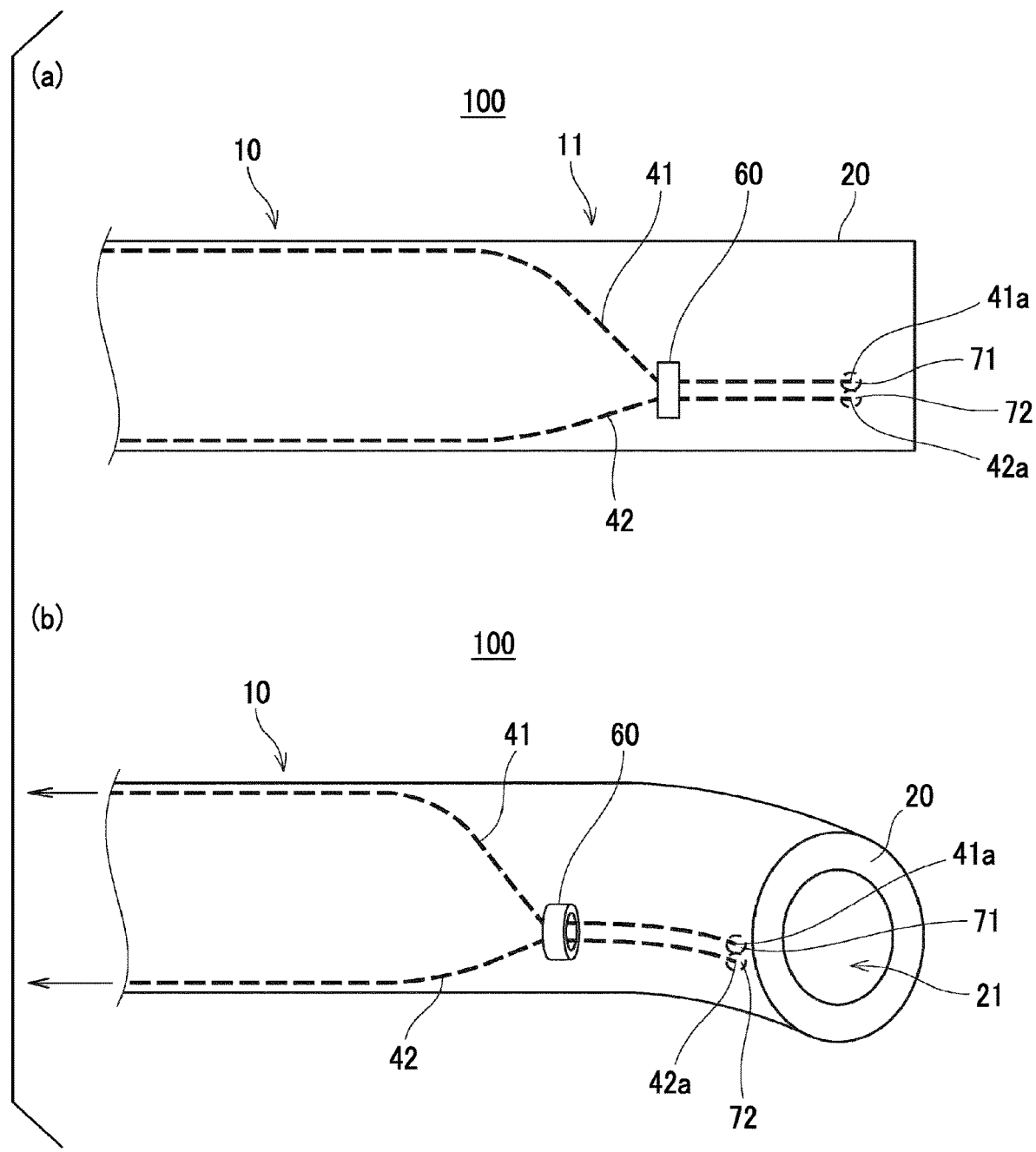
FIG. 11(*a*) and FIG. 11(*b*) are schematic views for showing the bending motion of a distal end part of the medical device body of the medical device related to Embodiments 1-2 and 2-2.
Figure 12:
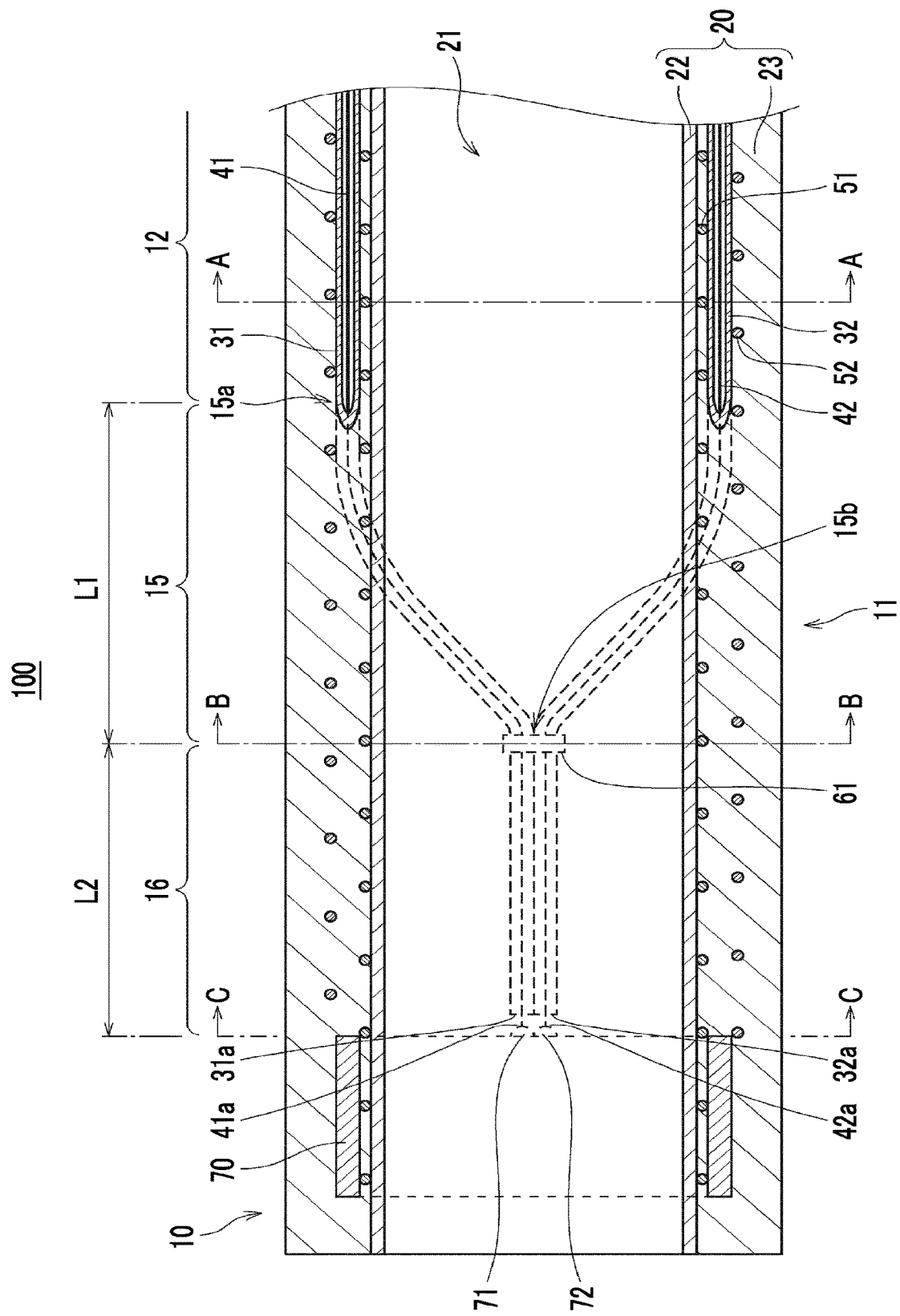
FIG. 12 is a longitudinal sectional view showing a portion on a distal end side in a medical device body of a medical device related to Embodiments 1-3 and 2-3.

FIG. 11(*a*) and FIG. 11(*b*) are schematic views for showing the bending motion when the distal end part 11 of the medical device body 10 is seen in the direction of arrow A of FIG. 10, FIG. 11(*a*) shows the state before the bending, and FIG. 11(*b*) shows the bent state.

The medical device 100 related to the present embodiment is different from the medical device 100 related to the above Embodiment 1-1 in terms of points to be described below, and is configured similarly to the medical device 100 related to the above Embodiment 1-1 in terms of the other points.

In the case of the present embodiment, the parallel region 16 where the first operating line 41 and the second operating line 42 extend in parallel close to each other is formed between the distal end (distal end position 15b) of the curved region 15, and the distal ends 41a and 42a of the first operating line 41 and the second operating line 42.

That is, the medical device body 10 is configured to include the resin tube 20 having the lumen 21, the first operating line 41 and the second operating line 42 are inserted around the lumen 21 of the resin tube 20, the first operating line 41 and the second operating line 42 are close to each other at a distance smaller than the thickness of the resin tube 20, at the distal end (distal end position 15b) of the curved region 15 curved such that the first operating line 41 and the second operating line 42 approach each other in the circumferential direction of the medical device body 10 gradually toward the distal end side, and the parallel region 16 where the first operating line 41 and the second operating line 42 extend in parallel close to each other is formed between the distal end (distal end position 15b) of the curved region 15, and the distal ends 41a and 42a of the first operating line 41 and the second operating line 42.

In the parallel region 16, the first hollow tube 31 and the second hollow tube 32 extend in parallel in abutment with or close to each other.

More specifically, in the case of the present embodiment, the medical device 100 further includes the annular member 60 buried in the resin tube 20 at the distal end part of the curved region 15. The annular member 60 is configured to have a rigidity higher than the resin tube 20, and have an external diameter smaller than the thickness of the resin tube 20 (refer to FIG. 10).

Also, the first operating line 41 and the second operating line 42 are inserted through the annular member 60.

Accordingly, the fluctuations of the paths of the first operating line 41 and the second operating line 42 can be more reliably limited.

More specifically, in the case of the present embodiment, the first hollow tube 31 and the second hollow tube 32 are inserted through the annular member 60.

That is, the medical device body 10 is buried in the resin tube 20, and are configured to include the first hollow tube 31 and the second hollow tube 32 through which the first operating line 41 and the second operating line 42 are respectively inserted, the first hollow tube 31 and the second hollow tube 32 are inserted through the annular member 60, and in the curved region 15, the first hollow tube 31 and the second hollow tube 32 are curved so as to approach each other in the circumferential direction of the medical device body 10 gradually toward the distal end side.

Although the materials of the annular member 60 are not particularly limited, the annular member 60 can be made of, for example, metal or hard resin.

Even in the case of the present embodiment, by pulling both of the first operating line 41 and the second operating line 42, the distal end part 11 of the medical device body 10 can be bent as shown in FIG. 11(*a*) and FIG. 11(*b*).

In this case, the bending angle in the parallel region 16 becomes steeper than the bending angle in the curved region 15.

As an example, the distance (the distance L2 shown in FIG. 9) from the distal end (distal end position 15b) of the curved region 15 to the distal ends 41a and 42a of the first operating line 41 and the second operating line 42 in the axial direction of the medical device body 10 is longer than the distance (the distance L1 shown in FIG. 9) from the proximal end (proximal end position 15a) of the curved region 15 to the distal end (distal end position 15b) thereof.

By virtue of such a configuration, the distal end part 11 can be more easily bent.

Additionally, the bending of the distal end part 11 can be caused mainly in the parallel region 16. For this reason, the friction between the first operating line 41 and the first hollow tube 31 in the curved region 15 and the friction between the second operating line 42 and the second hollow tube 32 can be substantially uniformly maintained irrespective of the bending angle of the distal end part 11. Therefore, the magnitude of a force required for pulling the first operating line 41 and the second operating line 42 can be substantially uniformly maintained irrespective of the bending angle of the distal end part 11.

Additionally, as another example, the distance (distance L1 shown in FIG. 9) from the proximal end (proximal end position 15a) of the curved region 15 to the distal end (distal end position 15b) thereof in the axial direction of the medical device body 10 is longer than the distance (distance L2 shown in FIG. 9) from the distal end (distal end position 15b) of the curved region 15 to the distal ends 41a and 42a of the first operating line 41 and the second operating line 42.

By virtue of such a configuration, the flexibility of the distal end part 11 can be limited to some extent.

Additionally, the curving of the first operating line 41, the second operating line 42, the first hollow tube 31, and the second hollow tube 32 in the curved region 15 can be made gentle. Therefore, the friction between the first operating line 41 and the first hollow tube 31 in the curved region 15 and the friction between the second operating line 42 and the second hollow tube 32 can be reduced.

Additionally, the length region where the first hollow tube 31 and the second hollow tube 32 translate close to each other in the distal end part 11 of the medical device body 10, that is, the length region with high rigidity is high becomes short. Therefore, excellent selectivity (excellent blood vessel selectivity or the like) when the distal end part 11 of the medical device body 10 is bent and is made to enter a branched body cavity can be obtained.

In addition, the distance L1 and the distance L2 may be the same. In this case, the smoothness of the pulling of the first operating line 41 and the second operating line 42 and the excellent selectivity when the distal end part 11 of the medical device body 10 is bent and is made to enter a branched body cavity can be obtained in a well-balanced manner.

Embodiment 1-3

Next, the medical device 100 related to Embodiment 1-3 will be described with reference to FIG. 12 to FIG. 18(c).

Figure 15:
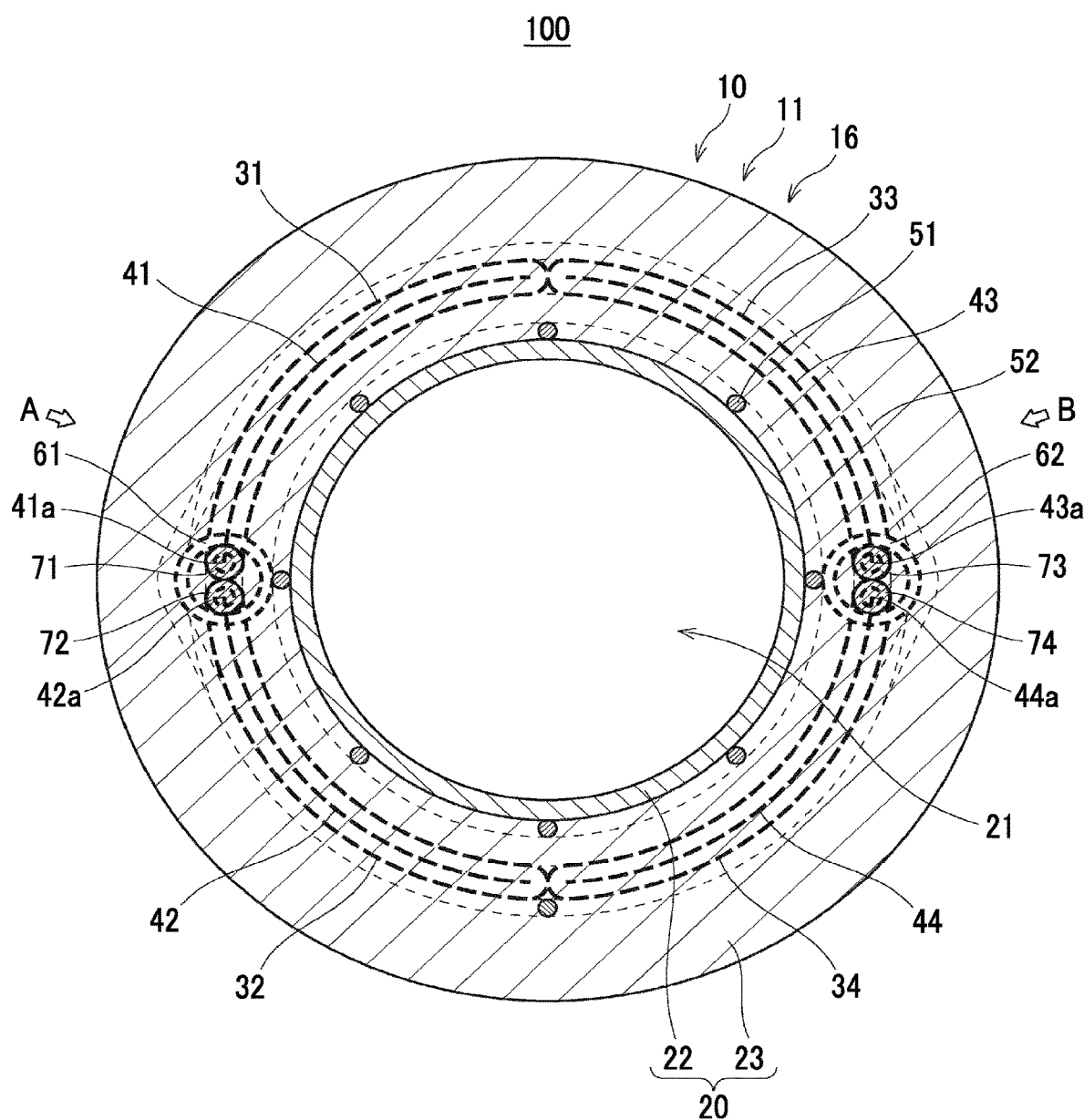
FIG. 15 is a cross-sectional view of the medical device body along line C-C of FIG. 12.

FIG. 16(a) and FIG. 16(b) are schematic views for showing a bending motion when the distal end part 11 of the medical device body 10 is seen in the direction of arrow A of FIG. 15, FIG. 16(a) shows a state before the bending, and FIG. 16(b) shows a bent state.

FIG. 16(c) and FIG. 16(d) are schematic views for showing a bending motion when the distal end part 11 of the medical device body 10 is seen in the direction of arrow B of FIG. 15, FIG. 16(c) shows a state before the bending, and FIG. 16(d) shows a bent state.

In FIG. 18(a), FIG. 18(b), and FIG. 18(c), a middle portion of the medical device body 10 in the longitudinal direction is broken and omitted. In the medical device body 10 shown in FIG. 8(a), FIG. 8(b), and FIG. 18(c), a portion closer to a proximal end side than the omitted portion and a portion closer to the distal end side than the omitted portion have rotational phases around the axis of the medical device body 10 that are different from each other by 90 degrees.

The medical device 100 related to the present embodiment is different from the medical device 100 related to the above Embodiment 1-2 in terms of points to be described below, and is configured similarly to the medical device 100 related to the above Embodiment 1-2 in terms of the other points.

The medical device 100 related to the present embodiment includes a third operating line 43 and a fourth operating line 44 that are inserted in the axial direction of the medical device body 10. The third operating line 43 and the fourth operating line 44 are respectively constituted of thin wires, such as metal or resin, similarly to the first operating line 41 and the second operating line 42.

The medical device body 10 further includes a third hollow tube 33 and a fourth hollow tube 34 that are buried in the resin tube 20. The third operating line 43 is inserted through the third hollow tube 33, and the fourth operating line 44 is inserted through the fourth hollow tube 34.

The third hollow tube 33 and the fourth hollow tube 34 are respectively the same sublumen tubes as the first hollow tube 31 and the second hollow tube 32, and inner cavities of these sublumen tubes are sublumens. That is, the operating lines (the third operating line 43, the fourth operating line 44) are respectively inserted through the sublumens.

The internal diameters of the third hollow tube 33 and the fourth hollow tube 34 are smaller than the internal diameter of the lumen 21.

Figure 13:
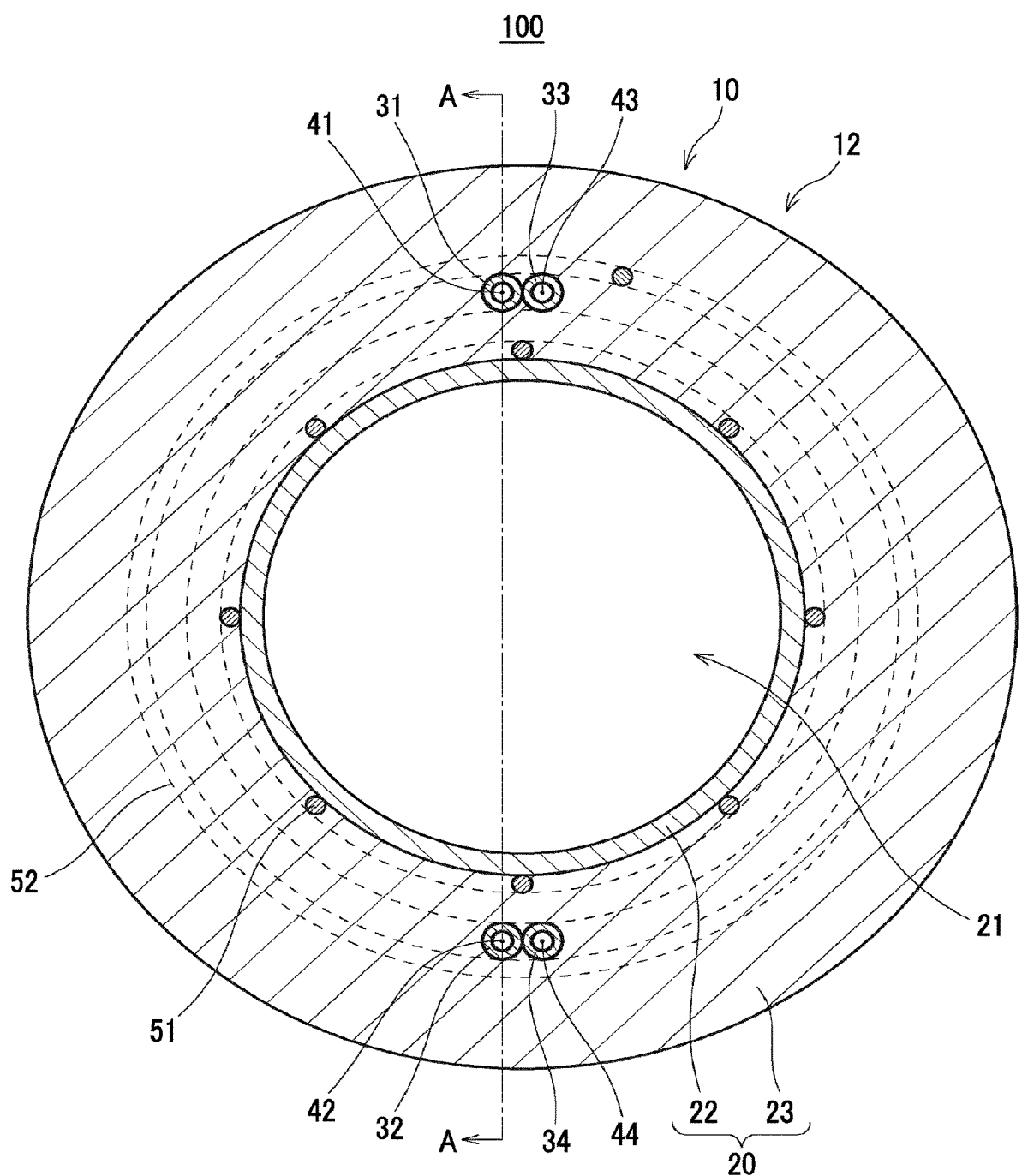
FIG. 13 is a cross-sectional view of the medical device body along line A-A of FIG. 12.

In the case of the present embodiment, in the intermediate part 12 of the medical device body 10, the first hollow tube 31 and the third hollow tube 33 extend in parallel in abutment with or close to each other, and the second hollow tube 32 and the fourth hollow tube 34 extend in parallel in abutment with or close to each other (refer to FIG. 13).

Similarly, even at the proximal end part of the medical device body 10, the first hollow tube 31 and the third hollow tube 33 extend in parallel in abutment with or close to each other, and the second hollow tube 32 and the fourth hollow tube 34 extend in parallel in abutment with or close to each other.

In the curved region 15 of the distal end part 11 of the medical device body 10, the third hollow tube 33 and the fourth hollow tube 34 are curved so as to approach each other in the circumferential direction of the medical device body 10 gradually toward the distal end side. Accordingly, the third operating line 43 within the third hollow tube 33 and the fourth operating line 44 within the fourth hollow tube 34 are curved so as to approach each other in the circumferential direction of the medical device body 10 gradually toward the distal end side.

A direction in which the third hollow tube 33 and the third operating line 43 are curved in the curved region 15 is a direction symmetrical to a direction in which the first hollow tube 31 and the first operating line 41 are curved.

Similarly, a direction in which the fourth hollow tube 34 and the fourth operating line 44 are curved in the curved region 15 is a direction symmetrical to a direction in which the second hollow tube 32 and the second operating line 42 are curved.

In addition, the respective hollow tubes (the first hollow tube 31, the second hollow tube 32, the third hollow tube 33, and the fourth hollow tube 34) do not intersect other hollow tubes. Additionally, the respective operating lines (the first operating line 41, the second operating line 42, the third operating line 43, and the fourth operating line 44) do not intersect other operating lines.

In the parallel region 16, similarly to the first operating line 41 and the second operating line 42 extending in parallel close to each other, the third operating line 43 and the fourth operating line 44 extend in parallel close to each other.

Additionally, in the parallel region 16, similarly to the first hollow tube 31 and the second hollow tube 32 extending in parallel in abutment with or close to each other, the third hollow tube 33 and the fourth hollow tube 34 extend in parallel in abutment with or close to each other.

A distal end 43a of the third operating line 43 protrudes from a distal end of the third hollow tube 33. Similarly, a distal end 44a of the fourth operating line 44 protrudes from a distal end of the fourth hollow tube 34.

The distal end 43a of the third operating line 43 is fixed to the marker 70 by a third fixing part 73 that is, for example, spot-shaped solder (FIG. 15).

Similarly, the distal end 44a of the fourth operating line 44 is fixed to the marker 70 by the fourth fixing part 74 that is, for example, spot-shaped solder.

The third fixing part 73 and the fourth fixing part 74 are disposed, for example, at an end part of the marker 70 on the proximal end side.

A region where the third fixing part 73 and the fourth fixing part 74 are disposed, and a region where the first fixing part 71 and the second fixing part 72 are disposed face each other in the circumferential direction of the medical device body 10.

In the case of the present embodiment, the distal end 43a of the third operating line 43 and the distal end 44a of the fourth operating line 44 are coupled to each other. That is, the distal ends of the third operating line 43 and the fourth operating line 44 are coupled to each other.

More specifically, the third fixing part 73 and the fourth fixing part 74 are adjacent to and in contact with each other. That is, the third fixing part 73 and the fourth fixing part 74 are integrated with each other.

In addition, the distal end 43a and the distal end 44a may be fixed to the marker 70 by a single fixing part.

Figure 14:
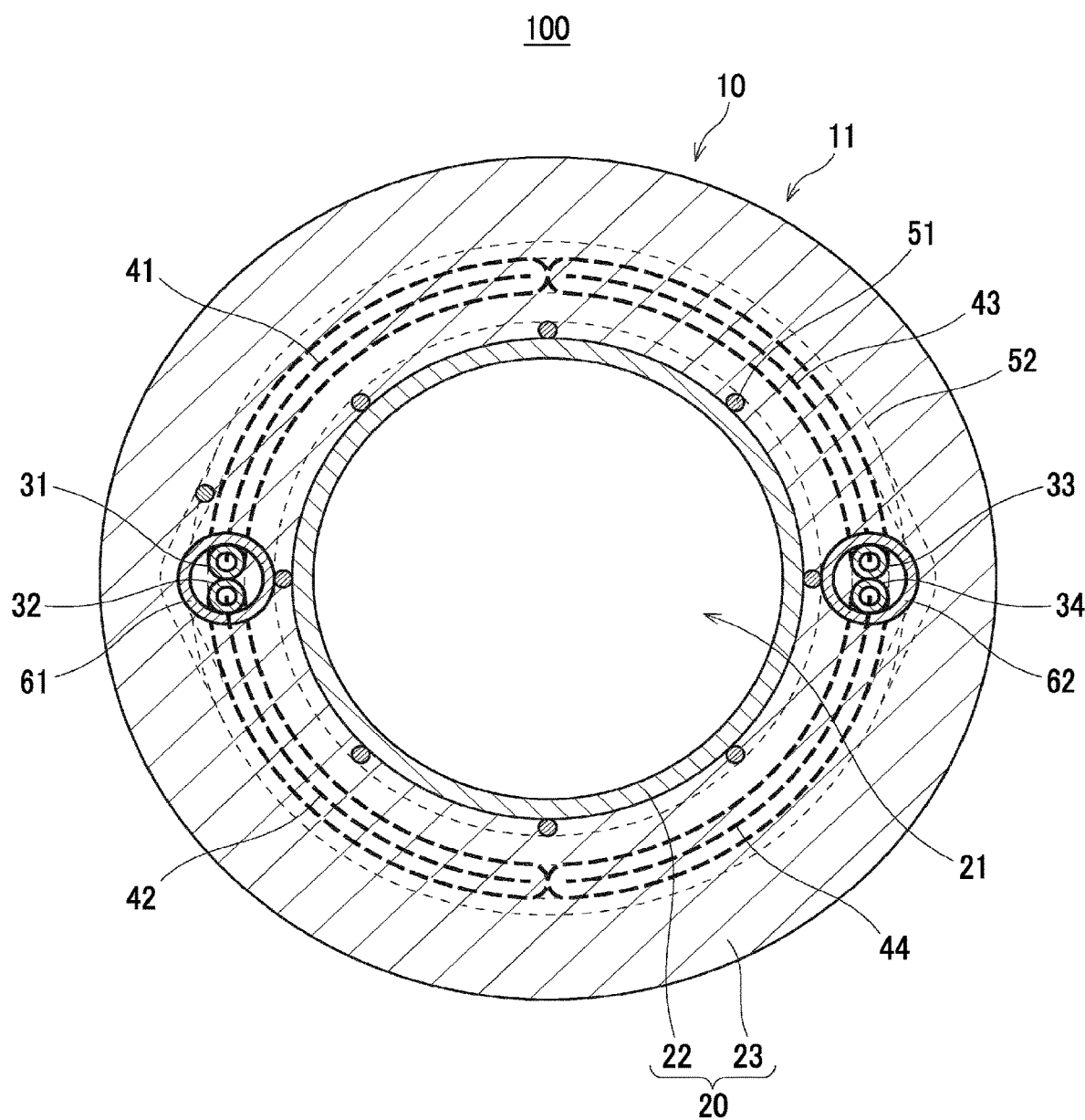
FIG. 14 is a cross-sectional view of the medical device body along line B-B of FIG. 12.

As shown in FIG. 14, in the case of the present embodiment, the medical device 100 includes a first annular member 61 buried in the resin tube 20 at the distal end part of the curved region 15 instead of the annular member 60. The first annular member 61 is the same as the annular member 60 in Embodiment 1-2, and the first hollow tube 31 and the second hollow tube 32 are inserted through the first annular member 61.

Moreover, in the case of the present embodiment, the medical device 100 includes a second annular member 62 buried in the resin tube 20 at the distal end part of the curved region 15. The second annular member 62 is the same as the first annular member 61. The third hollow tube 33 and the fourth hollow tube 34 are inserted through the second annular member 62.

The first annular member 61 and the second annular member 62 are disposed to face each other in the circumferential direction of the medical device body 10.

Even in the case of the present embodiment, by pulling both of the first operating line 41 and the second operating line 42, the distal end part 11 of the medical device body 10 can be bent in one direction as shown in FIG. 16(a) and FIG. 16(b).

Figure 16:
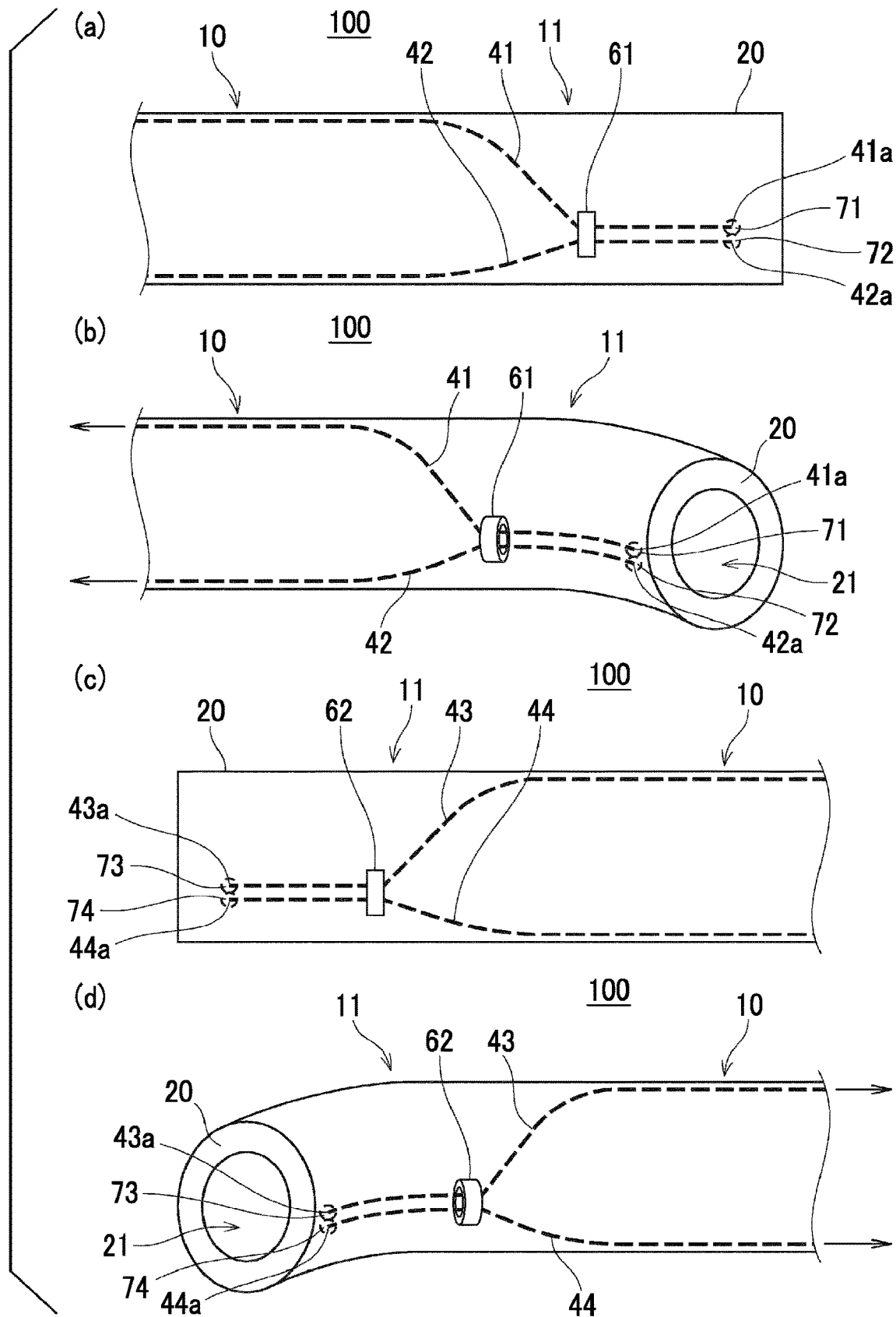
FIG. 16(*a*), FIG. 16(*b*), FIG. 16(*c*), and FIG. 16(*d*) are schematic views for showing the bending motion of a distal end part of the medical device body of the medical device related to Embodiments 1-3 and 2-3.

Moreover, in the case of the present embodiment, by pulling both of the third operating line 43 and the fourth operating line 44, the distal end part 11 of the medical device body 10 can be bent in an opposite direction opposite to the above one direction as shown in FIG. 16(c) and FIG. 16.(d).

Figure 17:
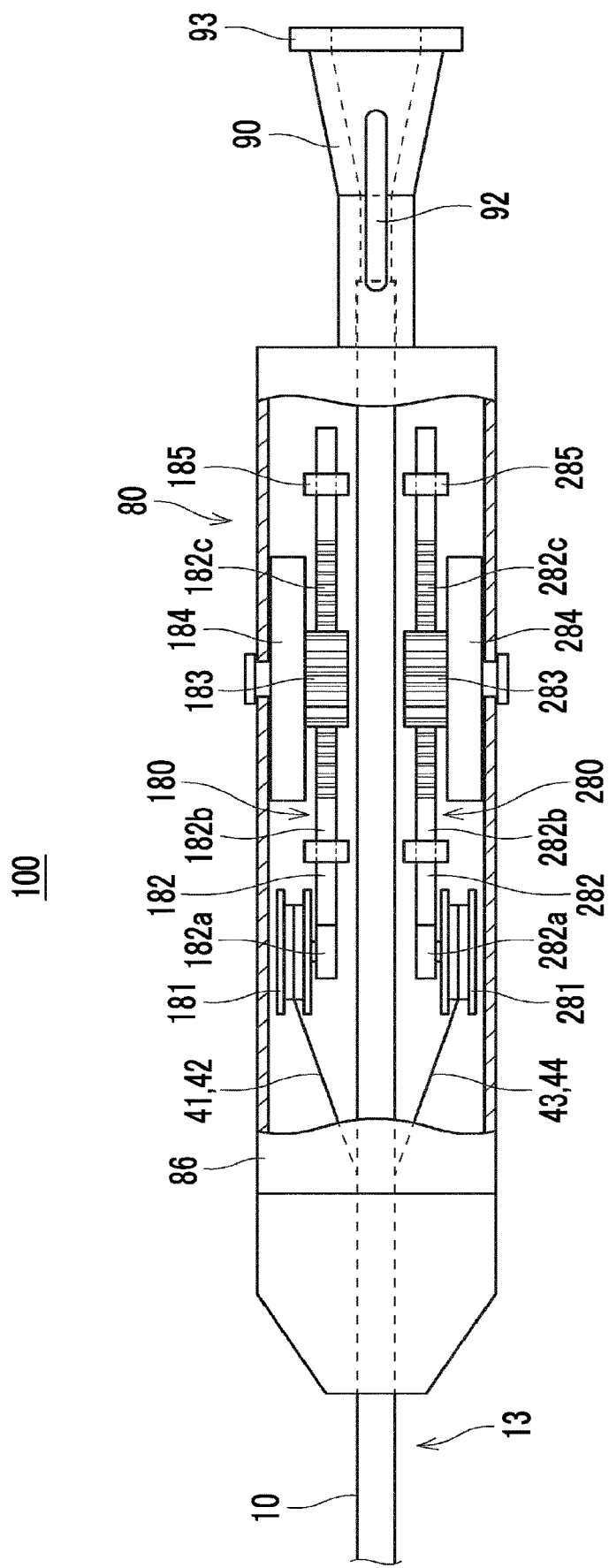
FIG. 17 is a side view showing a bending operating part and a portion in the vicinity thereof in the medical device related to Embodiments 1-3 and 2-3.

As shown in FIG. 17 and FIG. 18(a), in the case of the present embodiment, the bending operating part 80 includes a first bending operating part 180 for performing the bending operation of the distal end part 11 of the medical device body 10 by pulling the first operating line 41 and the second operating line 42, and a second bending operating part 280 for performing the bending operation of the distal end part 11 of the medical device body 10 by pulling the third operating line 43 and the fourth operating line 44.

The first bending operating part 180 includes a first rotating member 181, a first forward/backward movable member 182, a first pinion 183, a first dial operating part 184, and a first guide 185. The first rotating member 181, the first forward/backward movable member 182, the first pinion 183, the first dial operating part 184, and the first guide 185 are respectively equivalent to the rotating member 81, the forward/backward movable member 82, the pinion 83, the dial operating part 84, and the guide 85 that are described in Embodiment 1-1.

Hence, the first forward/backward movable member 182 includes a first holding part 182a, a first rod-shaped part 182b, and a first rack part 182c that are respectively equivalent to the holding part 82a, the rod-shaped part 82b, and the rack part 82c.

In Embodiment 1-1, similarly to the first operating line 41 and the second operating line 42 being wound around and fixed to the rotating member 81, the first operating line 41 and the second operating line 42 are wound around and fixed to the first rotating member 181.

The second bending operating part 280 includes a second rotating member 281, a second forward/backward movable member 282, a second pinion 283, a second dial operating part 284, and a second guide 285. The second rotating member 281, the second forward/backward movable member 282, the second pinion 283, the second dial operating part 284, and the second guide 285 are the same as the first rotating member 181, the first forward/backward movable member 182, the first pinion 183, the first dial operating part 184, and the first guide 185.

The second forward/backward movable member 282 includes a second holding part 282a, a second rod-shaped part 282b, and a second rack part 282c that are respectively the same as the first holding part 182a, the first rod-shaped part 182b, and the first rack part 182c.

Similarly to the first operating line 41 and the second operating line 42 being wound around and fixed to the first rotating member 181, the third operating line 43 and the fourth operating line 44 are wound around and fixed to the second rotating member 281.

For example, the second bending operating part 280 is disposed vertically symmetrically with respect to the first bending operating part 180 in FIG. 17.

In the case of the present embodiment, by rotating the first dial operating part 184 to move the first forward/backward movable member 182 and the first rotating member 181 backward, the first operating line 41 and the second operating line 42 can be pulled to bend the distal end part 11 of the medical device body 10 in one direction (FIG. 18(b)).

Additionally, by rotating the second dial operating part 284 to move the second the forward/backward movable member 282 and the second rotating member 281, the third operating line 43 and the fourth operating line 44 can be pulled to bend the distal end part 11 of the medical device body 10 in the direction opposite respect to the above one direction (FIG. 18(c)).

In this way, in the case of the present embodiment, the medical device 100 includes the second bending operating part 280 for performing the bending operation of the distal end part 11 of the medical device body 10 in a direction different from the bending direction of the distal end part 11 of the medical device body 10 by the pulling of the first operating line 41 and the second operating line 42, by pulling the third operating line 43 and the fourth operating line 44.

At the intermediate part 12 and the proximal end part in the axial direction of the medical device body 10, the third operating line 43 and the fourth operating line 44 extend in parallel so as to be spaced apart from each other in the circumferential direction of the medical device body 10, and at the distal end part 11 in the axial direction of the medical device body 10, the third operating line 43 and the fourth operating line 44 are curved and joined together so as to approach each other in the circumferential direction of the medical device body 10 gradually toward the distal end side.

Additionally, the third operating line 43 and the fourth operating line 44 are pulled at a time by the operation on the second bending operating part 280.

The second bending operating part 280 is configured to include a second rotating member 281 that is rotatably journaled and is engaged with the third operating line 43 and the fourth operating line 44, and to which a proximal end part of the third operating line 43 and a proximal end part of the fourth operating line 44 are fixed, and a second moving mechanism that moves the second rotating member 281 in a second pulling direction in which the third operating line 43 and the fourth operating line 44 are pulled, and an opposite direction opposite to the second pulling direction.

The second rotating member 281 has a second engaging part that is engaged with the third operating line 43 and the fourth operating line 44, and the second engaging part is formed in a circular shape or circular-arc shape centered on the rotation center of the second rotating member 281.

The second bending operating part 280 includes a second operation receiving part (second dial operating part 284) that operates in response to a user's operation, and as the power of the second operation receiving part is transmitted to the second rotating member 281 via the second moving mechanism, the second rotating member 281 moves in the second pulling direction and the direction opposite to the second pulling direction.

The second operation receiving part (second dial operating part 284) is journaled in a rotationally operable manner, and the second moving mechanism includes the second pinion 283 provided integrally and coaxially with the second operation receiving part, and a second rack member (second forward/backward movable member 282) that moves forward and backward in an interlocking manner with the rotation of the second pinion 283, and the second rotating member 281 is journaled to the second rack member.

Embodiment 1-4

Next, the medical device 100 related to Embodiment 1-4 will be described with reference to FIG. 19(*a*) and FIG. 19(*b*).

The medical device 100 related to the present embodiment is different from the medical device 100 related to the above Embodiment 1-1 in terms of points to be described below, and is configured similarly to the medical device 100 related to the above Embodiment 1-1 in terms of the other points.

In the case of the present embodiment, an easily bendable part 110 in which the flexibility of the medical device body 10 is locally high is formed in a region between the first operating line 41 and the second operating line 42 in the circumferential direction of the distal end part 11 of the medical device body 10 or a region located opposite to the region with respect to the axis of the medical device body 10.

Accordingly, since the flexibility of the distal end part 11 is improved, the tension acting on the first operating line 41 and the second operating line 42 during the bending operation can be reduced. Hence, the occurrence of the phenomenon in which the medical device body 10 rotates around the axis such that the first operating line 41 or the second operating line 42 tends to take a shortcut can be limited.

Figure 19:
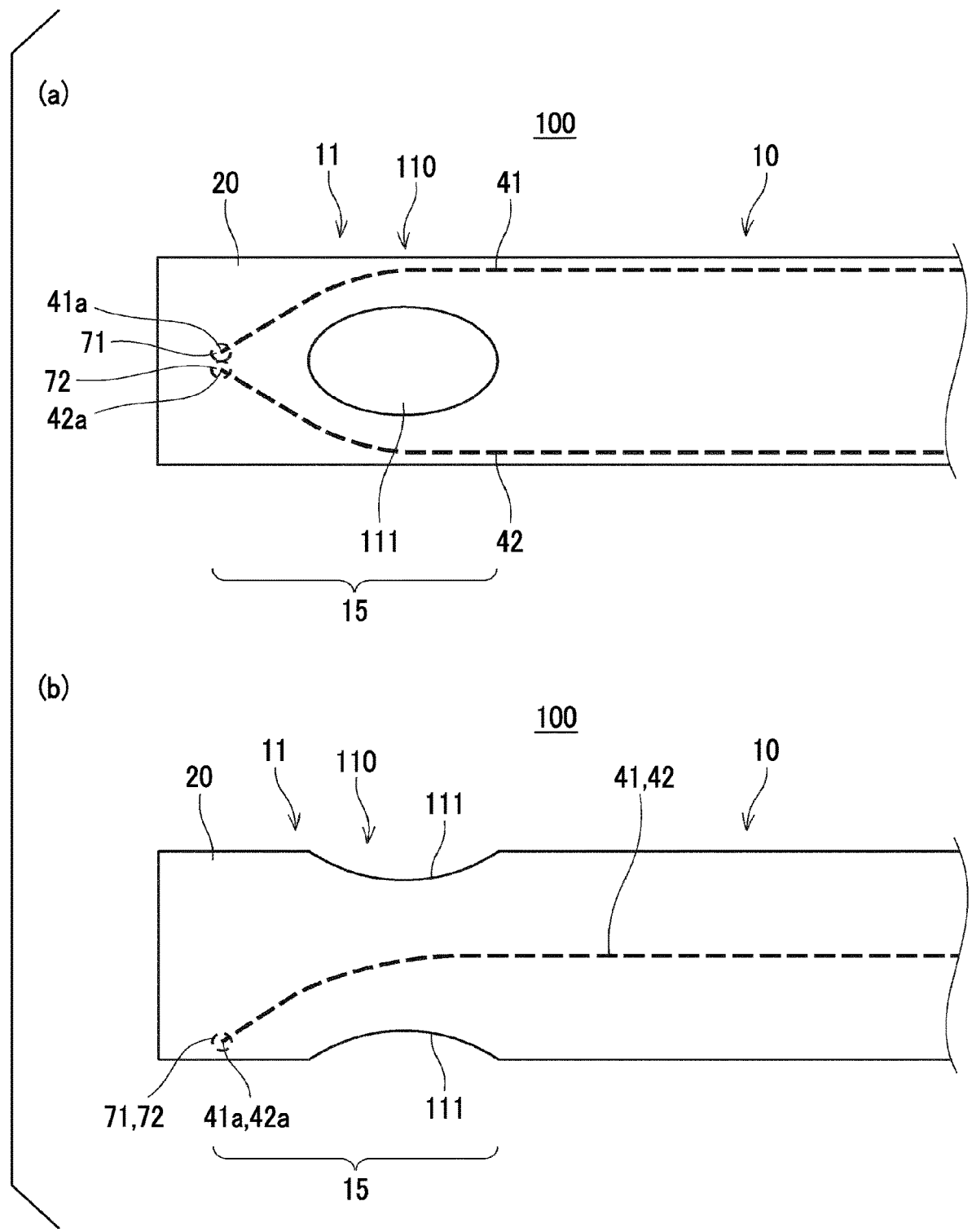
FIG. 19(*a*) and FIG. 19(*b*) are schematic views of a distal end part of a medical device body of a medical device related to Embodiments 1-4 and 2-4, and in these drawings, FIG. 19(*a*) is a plan view, and FIG. 19(*b*) is a side view.

More specifically, as shown in FIG. 19(*b*), easily bendable parts 110 are formed both in the region between the first operating line 41 and the second operating line 42 in the circumferential direction of the distal end part 11 of the medical device body 10 or the region located opposite to the region with respect to the axis of the medical device body 10.

Accordingly, the flexibility of the distal end part 11 is further improved.

The easily bendable part 110 is configured to include a notched part 111 formed on an outer surface side of the medical device body 10.

The notched part 111 can be formed in, for example, a shape gouged out in an arc as shown in FIG. 19(*b*). Accordingly, the distal end part 11 can be more steeply bent.

Embodiment 1-5

Next, the medical device 100 related to Embodiment 1-5 will be described with reference to FIG. 20(*a*) and FIG. 20(*b*).

The medical device 100 related to the present embodiment is different from the medical device 100 related to the above Embodiment 1-1 in terms of points to be described below, and is configured similarly to the medical device 100 related to the above Embodiment 1-1 in terms of the other points.

In the case of the present embodiment, an easily bendable part 110 in which the flexibility of the medical device body 10 is locally high is formed in a region between the first operating line 41 and the second operating line 42 in the circumferential direction of the distal end part 11 of the medical device body 10 or a region located opposite to the region with respect to the axis of the medical device body 10.

Accordingly, since the flexibility of the distal end part 11 is improved, the tension acting on the first operating line 41 and the second operating line 42 during the bending operation can be reduced. Hence, the occurrence of the phenomenon in which the medical device body 10 rotates around the axis such that the first operating line 41 or the second operating line 42 tends to take a shortcut can be limited.

Figure 20:
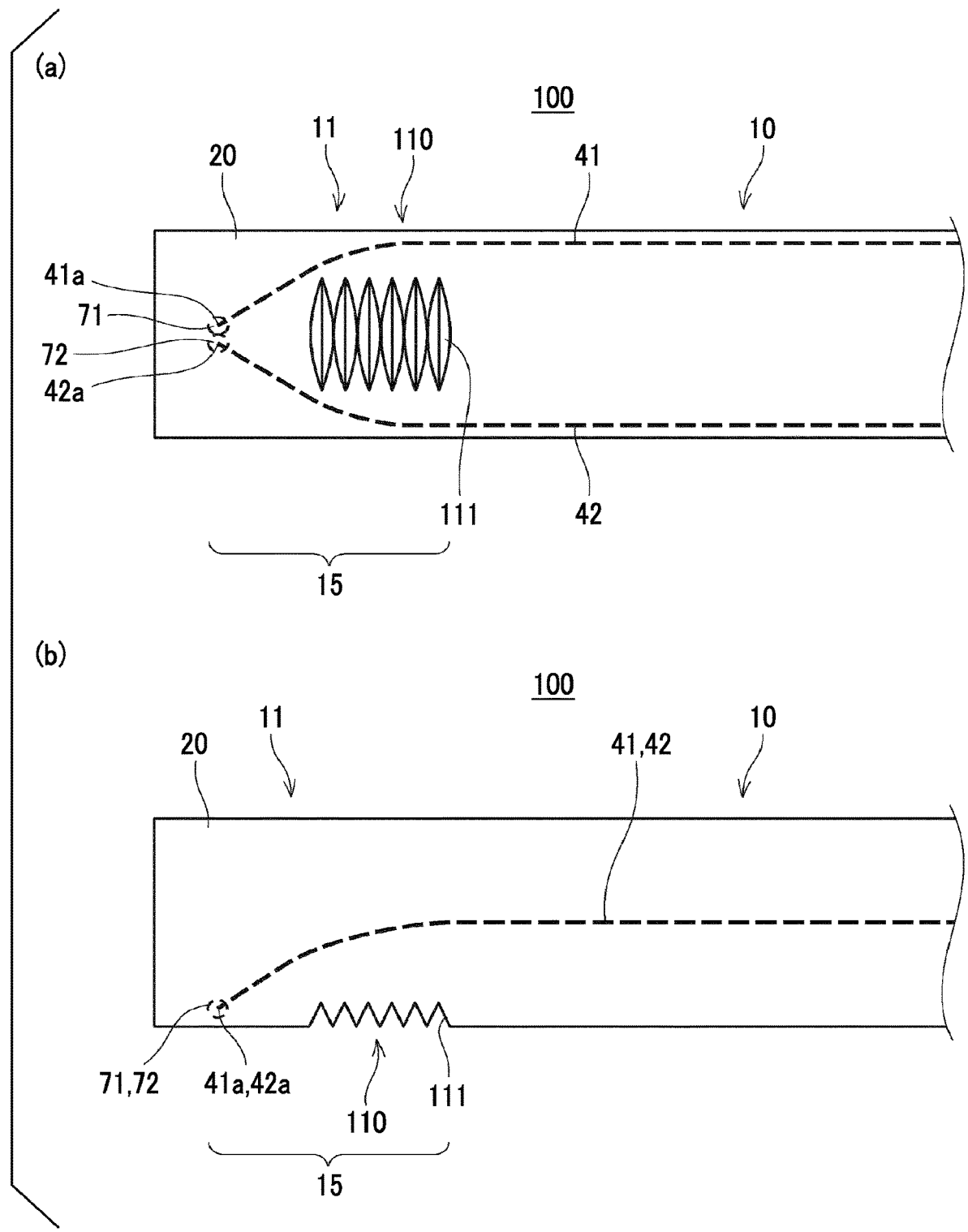
FIG. 20(*a*) and FIG. 20(*b*) are schematic views of a distal end part of a medical device body of a medical device related to Embodiments 1-5 and 2-5, and in these drawings, FIG. 20(*a*) is a plan view, and FIG. 20(*b*) is a side view.

More specifically, as shown in FIG. 20(*b*), the easily bendable part 110 is formed in the region between the first operating line 41 and the second operating line 42 in the circumferential direction of the distal end part 11 of the medical device body 10 or the easily bendable part 110 is not formed in the region located opposite to the region with respect to the axis of the medical device body 10.

However, easily bendable parts 110 may be formed both in the region between the first operating line 41 and the second operating line 42 in the circumferential direction of the distal end part 11 of the medical device body 10 or the region located opposite to the region with respect to the axis of the medical device body 10.

The easily bendable part 110 is configured to include a notched part 111 formed on an outer surface side of the medical device body 10. In the case of the present embodiment, the medical device body 10 has a plurality of notched parts 111 disposed adjacent to each other in the axial direction of the medical device body 10. The notched parts 111 are elongated in the circumferential direction of the medical device body 10, and the sectional shape thereof is a wedge shape.

In the case of the present embodiment, the distal end part 11 of the medical device body 10 is easily bent in the initial stage of the bending. However, if a certain amount of bending angle is reached, wedge-shaped inclined surfaces come in contact with each other, so that further bending becomes difficult (if a certain amount of bending angle is reached, rigidity become high).

For this reason, since the distal end part 11 of the medical device body 10 has excellent deformation resistance against compression in the axial direction when being pushed into a body cavity, the blood-vessels selectivity of the medical device 100 is excellent.

Embodiment 1-6

Next, Embodiment 1-6 will be described with reference to FIG. 21.

The medical device 100 related to the present embodiment is different from the medical device 100 related to the above Embodiment 1-3 in terms of points to be described below, and is configured similarly to the medical device 100 related to the above Embodiment 1-3 in terms of the other points.

In the case of the present embodiment, as will be described below, the configuration of the bending operating part 80 is different from the above Embodiment 1-3.

In the case of the present embodiment, the bending operating part 80 includes the housing 86, the first rotating member 181, the second rotating member 281, a dial operating part 194 (third rotating member), a first coupling wire 192 that couples the first rotating member 181 and the dial operating part 194 to each other, and a second coupling wire 193 that couples the second rotating member 281 and the dial operating part 194 to each other.

Each of the first rotating member 181 and the second rotating member 281 is, for example, a pulley.

A rotating shaft of the first rotating member 181 extends, for example, in a direction orthogonal to the axis direction (leftward-rightward direction in FIG. 21) of the medical device body 10 within the housing 86.

The rotating shaft of the first rotating member 181 is held by the housing 86 so as to be rotatable around the axis of the rotating shaft and movable relative to the housing 86 in the axis direction (leftward-rightward direction in FIG. 21) of the medical device body 10 within the housing 86. For example, the rotating shaft of the first rotating member 181 is journaled by an elongated hole (not shown) formed in the housing 86.

Similarly, a rotating shaft of the second rotating member 281 extends, for example, in the direction orthogonal to the axis direction of the medical device body 10 within the housing 86. The rotating shaft of the second rotating member 281 is held by the housing 86 so as to be rotatable around the axis of the rotating shaft and movable relative to the housing 86 in the axis direction of the medical device body 10 within the housing 86.

As an example, the rotating shaft of the first rotating member 181 and the rotating shaft of the second rotating member 281 are parallel to each other. However, these rotating shafts may not be parallel to each other.

The first operating line 41, the second operating line 42, the third operating line 43, and the fourth operating line 44 are delivered from the medical device body 10 within the housing 86.

The proximal end part of the first operating line 41 is wound around the first rotating member 181, for example, by one and a half turns, and the proximal end of the first operating line 41 is fixed to the rotating member 181. Similarly, the second operating line 42 is wound around the first rotating member 181, for example, by one and a half turns, and a proximal end of the second operating line 42 is fixed to the first rotating member 181. A winding direction of the first operating line 41 and a winding direction of the second operating line 42 around the first rotating member 181 are mutually opposite directions. For this reason, the rotational angle of the first rotating member 181 is autonomously adjusted to an angle at which the tension of the first operating line 41 and the tension of the second operating line 42 are balanced with each other.

The proximal end part of the third operating line 43 is wound around the second rotating member 281, for example, by one and a half turns, and a proximal end of the third operating line 43 is fixed to the second rotating member 281. Similarly, the fourth operating line 44 is wound around the second rotating member 281, for example, by one and a half turns, and a proximal end of the fourth operating line 44 is fixed to the second rotating member 281. A winding direction of the third operating line 43 and a winding direction of the fourth operating line 44 around the second rotating member 281 are mutually opposite directions. For this reason, the rotational angle of the second rotating member 281 is autonomously adjusted to an angle at which the tension of the third operating line 43 and the tension of the fourth operating line 44 are balanced with each other.

The dial operating part 194 is rotatably journaled to the housing 86. A rotating shaft of the dial operating part 194 extends in the direction orthogonal to the axis direction of the medical device body 10 within the housing 86.

As an example, the rotating shaft of the dial operating part 194 is parallel to the rotating shaft of the first rotating member 181 and the rotating shaft of the second rotating member 281. However, the rotating shaft of the dial operating part 194 may not be parallel to the rotating shaft of the first rotating member 181 and the rotating shaft of the second rotating member 281.

At least a portion of the dial operating part 194 is exposed to the outside of the housing 86 so that the operation in which an operator who performs the operation of the medical device 100 rotates the dial operating part 194 can be performed from the outside of the housing 86.

The dial operating part 194 includes, for example, a body part formed in a disk shape, and a winding part 191 fixed to one surface side of the body part. The winding part 191 is, for example, a cylindrical bobbin. The winding part 191 is disposed coaxially with the rotating shaft of the dial operating part 194.

A distal end of the first coupling wire 192 is coupled to the rotating shaft of the first rotating member 181. A proximal end part of the first coupling wire 192 is wound around the winding part 191, for example, by one and a half turns, and a proximal end of the first coupling wire 192 is fixed to the winding part 191 in a first coupling region 195.

Similarly, a distal end of the second coupling wire 193 is coupled to the rotating shaft of the second rotating member 281. A proximal end part of the second coupling wire 193 is wound around the winding part 191, for example, by one and a half turns, and a proximal end of the second coupling wire 193 is fixed to the winding part 191 in a second coupling region 196.

A winding direction of the first coupling wire 192 and a winding direction of the second coupling wire 193 around the winding part 191 are mutually opposite directions.

In the case of the present embodiment, as an operator who performs the operation of the medical device 100 grips the housing 86 or the hub 90 to rotate the dial operating part 194, the first coupling wire 192 or the second coupling wire 193 is selectively wound around the winding part 191. Therefore, the first rotating member 181 or the second rotating member 281 is selectively pulled to the proximal end side.

Figure 21:
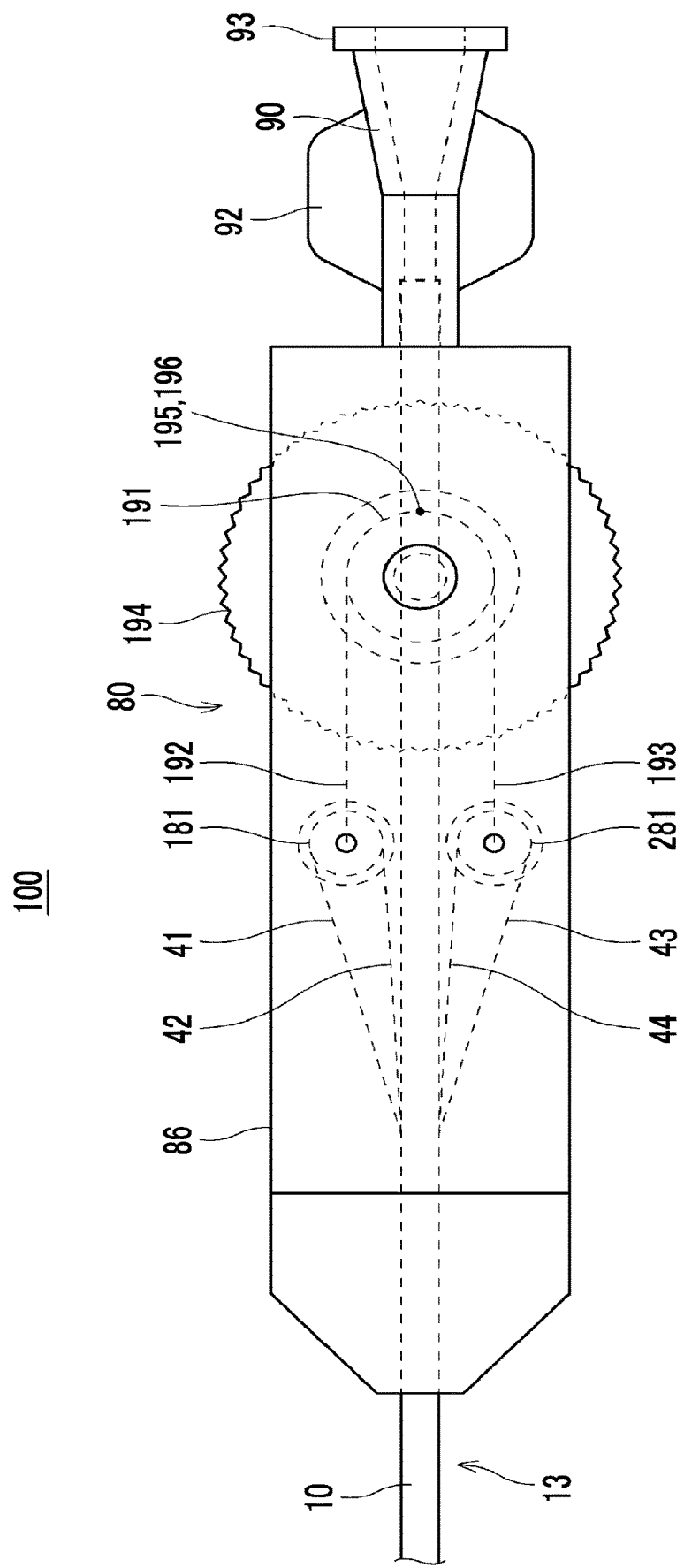
FIG. 21 is a plan view showing a bending operating part and a portion in the vicinity thereof in a medical device related to Embodiments 1-6 and 2-6.

That is, when the operation of rotating the dial operating part 194 in the clockwise direction in FIG. 21 is performed, the first coupling wire 192 is wound around the winding part 191. Therefore, the first rotating member 181 is pulled to the proximal end side. Therefore, since both of the first operating line 41 and the second operating line 42 are pulled to the proximal end side of the medical device body 10, the distal end part 11 of the medical device body 10 is bent in one direction.

Additionally, when the operation of rotating the dial operating part 194 in the counterclockwise direction in FIG. 21 is performed, the second coupling wire 193 is wound around the winding part 191. Therefore, the second rotating member 281 is pulled to the proximal end side. Therefore, since both of the third operating line 43 and the fourth operating line 44 are pulled to the proximal end side of the medical device body 10, the distal end part 11 of the medical device body 10 is bent in the above one direction.

That is, the operation of pulling both of the first operating line 41 and the second operating line 42 and the operation of pulling both of the third operating line 43 and the fourth operating line 44 can be performed by the operation on one dial operating part 194.

In this way, the medical device 100 related to the present embodiment includes the third operating line 43 and the fourth operating line 44 that are inserted in the axial direction of the medical device body 10. At the intermediate part 12 and the proximal end part 13 in the axial direction of the medical device body 10, the third operating line 43 and the fourth operating line 44 extend in parallel so as to be spaced apart from each other in the circumferential direction of the medical device body 10, and at the distal end part 11 in the axial direction of the medical device body 10, the third operating line 43 and the fourth operating line 44 are curved and joined together so as to approach each other in the circumferential direction of the medical device body 10 gradually toward the distal end side.

Then, the operation on the bending operating part 80 allows the third operating line 43 and the fourth operating line 44 to be pulled and allows the distal end part 11 of the medical device body 10 to be bent in a direction different from the bending direction of the distal end part 11 of the medical device body 10 by the pulling of the first operating line 41 and the second operating line 42.

More specifically, the bending operating part 80 includes the first rotating member 181, the second rotating member 281, and the third rotating member (dial operating part 194) that are rotatably journaled, the rotating shaft of the first rotating member 181 is coupled to the first coupling region 195 in the third rotating member, and the rotating shaft of the second rotating member 281 is coupled to the second coupling region 196 in the third rotating member.

Additionally, the proximal end part of the first operating line 41 and the proximal end part of the second operating line 42 are fixed to the first rotating member 181, and the proximal end part of the third operating line 43 and the proximal end part of the fourth operating line 44 are fixed to the second rotating member 281.

Then, as the third rotating member rotates in one direction, the first rotating member 181 is pulled and the first operating line 41 and the second operating line 42 are pulled, thereby bending the distal end part 11 of the medical device body 10, and as the third rotating member rotates in the direction opposite to the above one direction, the second rotating member 281 is pulled and the third operating line 43 and the fourth operating line 44 are pulled, thereby bending the distal end part 11 of the medical device body 10 in the direction (for example, opposite direction) different from the pulling direction of the distal end part 11 of the medical device body 10 by the pulling of the first operating line 41 and the second operating line 42.

In addition, in Embodiment 1-6, an example in which the rotating shaft of the first rotating member 181 is coupled to the third rotating member (dial operating part 194) via a wire (first coupling wire 192) and the rotating shaft of the second rotating member 281 is coupled to the third rotating member via a wire (second coupling wire 193) has been described. However, the invention is not limited to this example.

For example, the rotating shaft of the first rotating member 181 may be directly journaled to the first coupling region in the third rotating member, and the rotating shaft of the second rotating member 281 may be journaled to the second coupling region in the third rotating member. In this case, the third coupling member does not need to include the above winding part 191.

Embodiment 1-7

Next, Embodiment 1-7 will be described with reference to FIG. 22.

The medical device 100 related to the present embodiment is different from the medical device 100 related to the above Embodiment 1-6 in terms of points to be described below, and is configured similarly to the medical device 100 related to the above Embodiment 1-6 in terms of the other points.

In the case of the present embodiment, as will be described below, the configuration of the bending operating part 80 is different from the above Embodiment 1-6.

In the case of the present embodiment, the bending operating part 80 does not include the winding part 191, the first coupling wire 192, and the second coupling wire 193 that are shown in FIG. 21. Instead of this, the bending operating part 80 includes a pinion 197, a first rack member 198, a second rack member 199, and a guide 200 that are shown in FIG. 22.

The pinion 197 is formed integrally with the dial operating part 194 on one surface of the disk-shaped dial operating part 194, and is disposed coaxially with the rotating shaft of the dial operating part 194.

The first rack member 198 is a rod-shaped member that extends in the axis direction of the medical device body 10 within the housing 86. The first rotating member 181 is rotatably journaled to a distal end part of the first rack member 198. A rack, which meshes with a gear at an outer periphery of the pinion 197, is formed on one side surface of the first rack member 198.

The bending operating part 80 includes, for example, a pair of front and rear guides 200 that are provided corresponding to the first rack member 198. The first rack member 198 is linearly guided by the guides 200 so as to be linearly movable forward and backward in the axis direction of the medical device body 10 within the housing 86.

Similarly, the second rack member 199 is a rod-shaped member that extends in the axis direction of the medical device body 10 within the housing 86. The second rotating member 281 is rotatably journaled to a distal end part of the second rack member 199. The rack, which meshes with the gear at the outer periphery of the pinion 197, is formed on one side surface of the second rack member 199.

The bending operating part 80 includes, for example, a pair of front and rear guides 200 that are provided corresponding to the second rack member 199. The second rack member 199 is linearly guided by the guides 200 so as to be linearly movable forward and backward in the axis direction of the medical device body 10 within the housing 86.

Even in the case of the present embodiment, engagement and fixation of the first operating line 41 with respect to the first rotating member 181 and the second operating line 42 and engagement and fixation of the third operating line 43 with respect to the second rotating member 281 and the fourth operating line 44 are the same as those of Embodiment 1-6.

For this reason, the rotational angle of the first rotating member 181 is autonomously adjusted to an angle at which the tension of the first operating line 41 and the tension of the second operating line 42 are balanced with each other, and the rotational angle of the second rotating member 281 is autonomously adjusted to an angle at which the tension of the third operating line 43 and the tension of the fourth operating line 44 are balanced with each other.

In the case of the present embodiment, as an operator who performs the operation of the medical device 100 grips the housing 86 or the hub 90 to rotate the dial operating part 194, the first rack member 198 or the second rack member 199, which respectively meshes with the pinion 197, selectively moves to the proximal end side.

That is, when the operation of rotating the dial operating part 194 in the clockwise direction in FIG. 22 is performed, the first rack member 198 moves (moves backward) to the proximal end side. Therefore, the first rotating member 181 is pulled to the proximal end side. Therefore, since both of the first operating line 41 and the second operating line 42 are pulled to the proximal end side of the medical device body 10, the distal end part 11 of the medical device body 10 is bent in one direction.

Additionally, when the operation of rotating the dial operating part 194 in the counterclockwise direction in FIG. 22 is performed, the second rack member 199 moves (moves backward) to the proximal end side. Therefore, the second rotating member 281 is pulled to the proximal end side. Therefore, since both of the third operating line 43 and the fourth operating line 44 are pulled to the proximal end side of the medical device body 10, the distal end part 11 of the medical device body 10 is bent in the above one direction.

In addition, the second rack member 199 moves to the proximal end side when the first rack member 198 moves to the proximal end side, and the first rack member 198 moves to the distal end side when the second rack member 199 moves to the distal end side.

In this way, in the case of the present embodiment, the bending operating part 80 includes the first rotating member 181, the second rotating member 281, and the third rotating member (dial operating part 194) that are rotatably journaled, the pinion 197 provided integrally and coaxially with the third rotating member, the first rack member 198 to which the rotating shaft of the first rotating member 181 is coupled and which moves forward and backward in an interlocking manner with the rotation of the pinion 197, and the second rack member 199 to which the rotating shaft of the second rotating member 281 is coupled and which moves forward and backward always in an opposite direction opposite to the forward/backward movement direction of the first rack member 198 in an interlocking manner with the rotation of the pinion 197.

The proximal end part of the first operating line 41 and the proximal end part of the second operating line 42 are fixed to the first rotating member 181, and the proximal end part of the third operating line 43 and the proximal end part of the fourth operating line 44 are fixed to the second rotating member 281.

As the third rotating member (dial operating part 194) rotates in one direction, the first rotating member 181 is pulled via the first rack member 198 and the first operating line 41 and the second operating line 42 are pulled, thereby bending the distal end part 11 of the medical device body 10.

Additionally, as the third rotating member rotates in an opposite direction opposite to the above one direction, the second rotating member 281 is pulled via the second rack member 199 and the third operating line 43 and the fourth operating line 44 are pulled, thereby bending the distal end part 11 of the medical device body 10 in the direction different from the bending direction of the distal end part 11 of the medical device body 10 by the pulling of the first operating line 41 and the second operating line 42.

Although the respective embodiments have been described above with reference to the drawings, these are examples of the invention, and various configurations other than the above can also be adopted.

An example in which the rotating mechanism of the bending operating part 80 is the dial operating part 84 has been described in the above Embodiment 1-1. However, the rotating mechanism of the bending operating part 80 may be others (for example, a rotary lever or the like) than the dial operating part 84.

Additionally, an example in which the conversion mechanism of the bending operating part 80 is configured to include the rack (rack part 82c) and the pinion 83 has been described in the above Embodiment 1-1. However, the bending operating part 80 may be configured to include other conversion mechanisms (for example, a cam, a link mechanism, a pin, a guide with a groove, or the like).

The same applies to the other embodiments.

Additionally, an example in which the first operating line 41 and the second operating line 42 are constituted of separate thin lines has been described in the above respective embodiments. However, each of the first operating line 41 and the second operating line 42 may be constituted of a portion of one thin line. That is, the one thin line may be folded at the distal ends 41a and 42a.

Similarly, an example in which the third operating line 43 and the fourth operating line 44 are constituted of separate thin lines has been described above. However, each of the third operating line 43 and the fourth operating line 44 may be constituted of a portion of one thin line. That is, the one thin line may be folded at the distal ends 43a and 44a.

Additionally, an example in which the proximal end part of the first operating line 41 and the proximal end part of the second operating line 42 are individually fixed to the bending operating part 80 has been described in the above respective embodiments. However, the proximal end of the first operating line 41 and the proximal end of the second operating line 42 may be are connected to each other, and may be looped (looped in a portion engaged with the rotating member 81) in the bending operating part 80.

Similarly, an example in which the proximal end part of the third operating line 43 and the proximal end part of the fourth operating line 44 are individually fixed to the second bending operating part 280 has been described above. However, the proximal end of the third operating line 43 and the proximal end of the fourth operating line 44 may be connected to each other, and may be looped (looped in the portion engaged with the second rotating member 281) in the second bending operating part 280.

Figure 18:
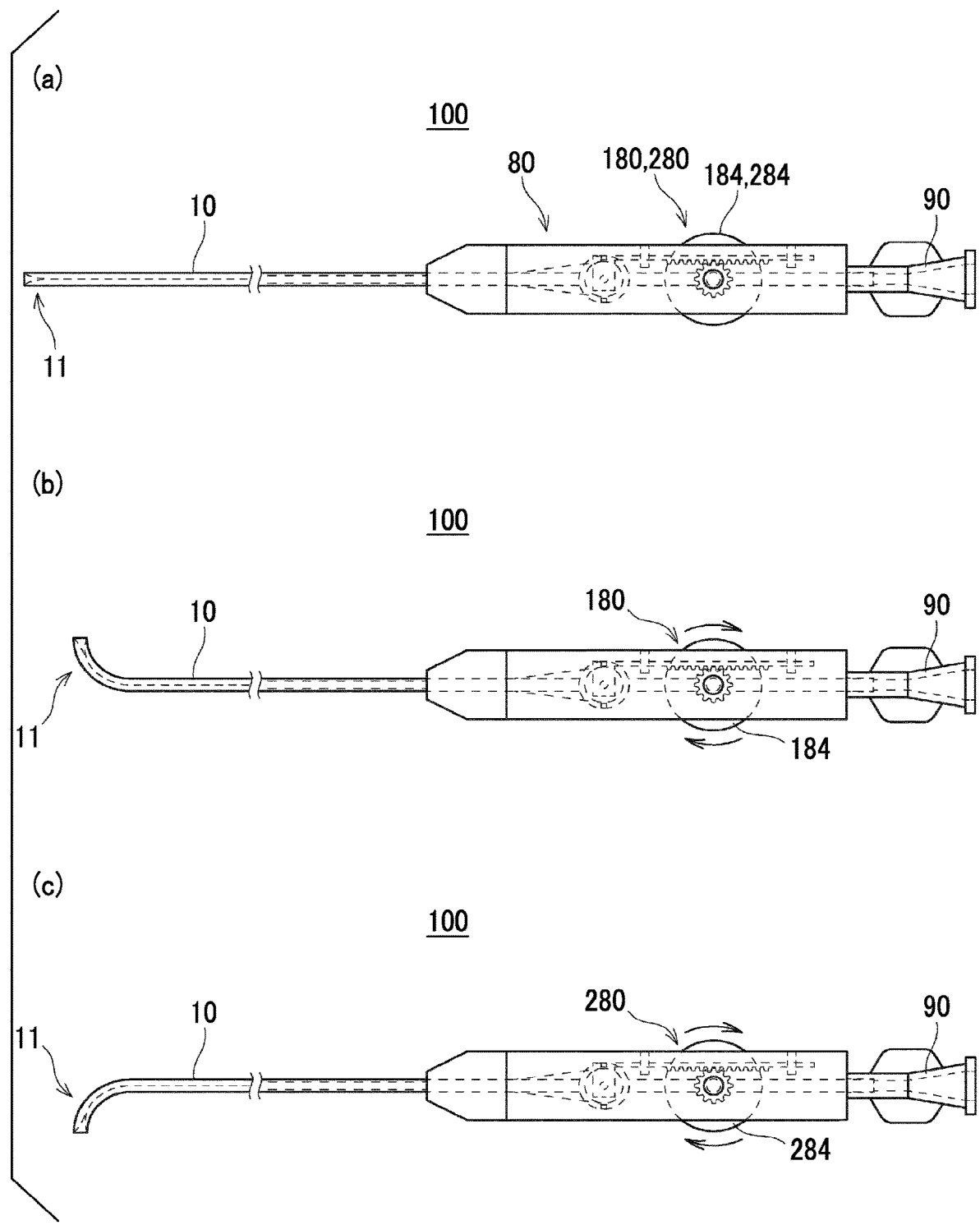
FIG. 18(*a*) is an overall view of the medical device related to Embodiments 1-3 and 2-3, FIG. 18(*b*) is an overall view showing a state where the distal end part of the medical device body of the medical device related to Embodiments 1-3 and 2-3 is bent to one side, and FIG. 18(*c*) is an overall view showing a state where the distal end part of the medical device body of the medical device related to Embodiments 1-3 and 2-3 is bent to the other side.

In the above Embodiment 1-3 (FIG. 17, FIG. 18(*a*), FIG. 18(*b*), FIG. 18(*c*)), an example in which the first dial operating part 184 and the second dial operating part 284 are disposed to overlap each other in the direction orthogonal to the plate surfaces thereof and the rotating shaft of the first dial operating part 184 and the rotating shaft of the second dial operating part 284 are disposed coaxially with each other has been described. However, the invention is not limited to this example.

For example, the rotating shaft of the first dial operating part 184 and the rotating shaft of the second dial operating part 284 do not need to be disposed coaxially with each other. For example, the first dial operating part 184 and the second dial operating part 284 may be disposed at positions different from each other in the axial direction of the medical device body 10.

Embodiment 2-1

First, Embodiment 2-1 will be described with reference to FIG. 1 to FIG. 8(*b*). In addition, FIG. 1 is the sectional view along line A-A of FIG. 2.

FIG. 5(*a*) and FIG. 5(*b*) are schematic views for showing the bending motion when the distal end part 11 of the medical device body 10 is seen in the direction of arrow A of FIG. 4, FIG. 5(*a*) shows the state before the bending, and FIG. 5(*b*) shows the bent state.

In FIG. 7, the housing 86 of the bending operating part 80 is broken partially to show the internal structure of the housing 86.

In FIG. 8(*a*) and FIG. 8(*b*), the middle portion of the medical device body 10 in the longitudinal direction is broken and omitted. In the medical device body 10 shown in FIG. 8(*a*) and FIG. 8(*b*), the portion closer to the proximal end side than the omitted portion and the portion closer to the distal end side than the omitted portion have rotational phases around the axis of the medical device body 10 that are different from each other by 90 degrees.

As shown in any of FIG. 1 to FIG. 8(*b*), the medical device 100 related to the present embodiment includes the elongated medical device body 10, the first operating line 41 and the second operating line 42 that are inserted in the axial direction of the medical device body 10, and the bending operating part 80 (FIG. 6, FIG. 7) for performing the bending operation of the distal end part 11 of the medical device body 10 by pulling the first operating line 41 and the second operating line 42.

The bending operating part 80 includes the rotating member 81 that is rotatably journaled and to which the proximal end part of the first operating line 41 and the proximal end part of the second operating line 42 are fixed, the moving mechanism that moves the rotating member 81 in the pulling direction in which the first operating line 41 and the second operating line 42 are pulled, and the direction opposite to the pulling direction, and the operation receiving part (for example, the dial operating part 84) that operates in response to the operation of a user (operator). Then, as the power of the operation receiving part is transmitted to the rotating member 81 via the moving mechanism, the rotating member 81 is adapted to move in the above pulling direction and the direction opposite to the above pulling direction.

According to the present embodiment, as a user performs the operation of moving the rotating member 81 in the above pulling direction on the operation receiving part, both of the first operating line 41 and the second operating line 42, which are fixed to the rotating member 81, can be pulled.

Accordingly, the operability according to various needs can be suitably realized, within a range according to the arrangement (the first operating line 41 and the second operating line 42 in the present embodiment) of the operating lines.

Even in the case of the present embodiment, by pulling both of the first operating line 41 and the second operating line 42, the distal end part 11 of the medical device body 10 can be bent as shown in FIG. 5(*a*) and FIG. 5(*b*). In this case, the load of pulling the distal end part 11 of the medical device body 10 with the first operating line 41 and the load of pulling the distal end part 11 with the second operating line 42 can be balanced with each other. Therefore, the occurrence of the phenomenon in which the medical device body 10 rotates around the axis such that the first operating line 41 or the second operating line 42 tends to take a shortcut can be limited.

Thus, even when the distal end part 11 is further bent after the medical device body 10 passes through a body cavity, such as a curved blood vessel, it is possible to more reliably bens the distal end part 11 in a desired direction.

More specifically, at the intermediate part 12 and the proximal end part 13 (FIG. 6, FIG. 7) of the medical device body 10 in the axial direction, the first operating line 41 and the second operating line 42 extend in parallel so as to be spaced apart from each other in the circumferential direction of the medical device body 10.

At the distal end part 11 of the medical device body 10 in the axial direction, the first operating line 41 and the second operating line 42 are curved and joined together so as to approach each other in the circumferential direction of the medical device body 10 gradually toward the distal end side.

Here, the fact that the first operating line 41 and the second operating line 42 are close to each other means that the distal end 41*a* of the first operating line 41 and the distal end 42*a* of the second operating line 42 are joined together. It is preferable that the distal end 41*a* of the first operating line 41 and the distal end 42*a* of the second operating line 42 are close to each other at a distance smaller than the thickness of the resin tube 20 to be described below.

In addition, as in the case of the present embodiment, in a case where the number of operating lines provided in the medical device 100 is two and these operating lines are joined together, the direction in which the distal end part 11 can be bent by pulling the operating line is one direction.

Here, in the catheter of Patent Document 1, when the distal end part is further bent after passing through a body cavity, such as a curved blood vessel, the distal end part can be easily bent in an inward direction of the curve. However, the distal end part is not easily bent in an outward direction.

This is because, if an operating line located on an outcourse side of the curve is pulled to bend a distal end of the catheter in the outward direction, the catheter may rotate in a direction in which the path of the pulled operating line becomes short and around the axis of the catheter within a curved blood vessel.

In contrast, according to the present embodiment, it is possible to more reliably bend the distal end part 11 in a desired direction as described above.

The medical device 100 is, typically, a catheter.

The medical device body 10 includes the resin tube 20 of which the inner cavity is as the lumen 21.

In the case of the present embodiment, the resin tube 20 has the layer structure including the hollow tubular inner layer 22 of which the inner cavity is the lumen 21, and the hollow tubular outer layer 23 that is formed coaxially with the inner layer 22 and at the outer periphery of the inner layer 22. The inner layer 22 and the outer layer 23 are respectively made of resin materials. The inner peripheral surface of the outer layer 23 is joined to the outer peripheral surface of the inner layer 22.

The resin material constituting the inner layer 22 and the resin material constituting the outer layer 23 may be different from each other, or may be the same as each other.

The hydrophilic coat may be formed on the outer surface layer of the medical device body 10 as necessary.

The lumen 21 is continuously formed from the distal end of the medical device body 10 to the proximal end thereof, and opens at the distal end and the proximal end of the medical device body 10, respectively.

The medical device body 10 further includes the first hollow tube 31 and the second hollow tube 32 that are buried in the resin tube 20. The first operating line 41 is inserted through the first hollow tube 31, and the second operating line 42 is inserted through the second hollow tube 32.

The first hollow tube 31 and the second hollow tube 32 are respectively sublumen tubes, and the inner cavities of these sublumen tubes are sublumens. That is, the operating lines (the first operating line 41, the second operating line 42) are respectively inserted through the sublumens.

The internal diameters of the first hollow tube 31 and the second hollow tube 32 are smaller than the internal diameter of the lumen 21.

The first operating line 41 and the second operating line 42 are respectively constituted of thin lines, such as metal or resin.

In addition, in the case of the present embodiment, the first hollow tube 31 and the second hollow tube 32 are disposed avoiding the position on the in-course side when the distal end part 11 of the medical device body 10 is bent. Therefore, the bending of the distal end part 11 can be easily performed. Since the first hollow tube 31 and the second hollow tube 32 are spaced apart from the in-course side, particularly on a further proximal end side in the distal end part 11, the bending becomes easy.

At the distal end part 11 of the medical device body 10, the first hollow tube 31 and the second hollow tube 32 are curved so as to approach each other in the circumferential direction of the medical device body 10 gradually toward the distal end side. Accordingly, the first operating line 41 within the first hollow tube 31 and the second operating line 42 within the second hollow tube 32 are curved so as to approach each other in the circumferential direction of the medical device body 10 gradually toward the distal end side.

In addition, the first hollow tube 31 and the second hollow tube 32 do not intersect each other. Additionally, the first operating line 41 and the second operating line 42 do not intersect each other.

In this way, the medical device body 10 is configured to include the resin tube 20 having the lumen 21, and the first hollow tube 31 and the second hollow tube 32 that are buried in the resin tube 20 and allows the first operating line 41 and the second operating line 42 to be respectively inserted therethrough. At the distal end part 11 of the medical device body 10 in the axial direction, the first hollow tube 31 and the second hollow tube 32 are curved so as to approach each other in the circumferential direction of the medical device body 10 gradually toward the distal end side.

In addition, the region where the first operating line 41 and the second operating line 42 approach each other in the circumferential direction of the medical device body 10 gradually toward the distal end side in the axial direction of the medical device body 10 is referred to as the curved region 15. The proximal end position 15a of the curved region 15 is a position where the first operating line 41 and the second operating line 42 starts to be curved toward each other, and the distal end position 15b of the curved region 15 is a position where the first operating line 41 and the second operating line 42 finishes being curved toward each other.

In the case of the present embodiment, the distal end position 15b of the curved region 15 is a position where the distal ends 41a and 42a of the first operating line 41 and the second operating line 42 are disposed, or a position in the vicinity thereof.

The distal end 41a of the first operating line 41 protrudes from the distal end 31a of the first hollow tube 31. Similarly, the distal end 42a of the second operating line 42 protrudes from the distal end 32a of the second hollow tube 32.

For example, the distal end 41a is located in the vicinity of the distal end 31a, and the distal end 42a is located in the vicinity of the distal end 32a.

The medical device body 10 includes, for example, the braid layer 51 buried in the resin tube 20. Accordingly, the medical device body 10 is reinforced by the braid layer 51. The braid layer 51 is configured by braiding two or more wires. The braid layer 51 is disposed, for example, around the inner layer 22.

In addition, the first hollow tube 31 and the second hollow tube 32 are disposed, for example, on a further radially outer side (at a position far from the axis of the medical device body 10) of the medical device body 10 than the braid layer 51.

The medical device body 10 further includes the winding wire 52 buried in the resin tube 20. The winding wire 52 is wound on a further radially outer side of the medical device body 10 than the braid layer 51, the first hollow tube 31, and the second hollow tube 32. For example, the winding wire 52 constrains the first hollow tube 31 and the second hollow tube 32 with respect to the braid layer 51.

In the curved region 15, the first hollow tube 31 and the second hollow tube 32 are disposed along the outer periphery of the braid layer 51 (refer to FIG. 3 and FIG. 4).

In the curved region 15, the distance between the first hollow tube 31 and the second hollow tube 32 in the circumferential direction of the medical device body 10 decreases gradually toward the distal end side, and the distance between the first operating line 41 and the second operating line 42 in the circumferential direction of the medical device body 10 decreases gradually toward the distal end side.

In addition, the first hollow tube 31 and the second hollow tube 32 are deformed in a curved shape, for example, on a further distal end side than the proximal end position 15a of the curved region 15. The first hollow tube 31 and the second hollow tube 32 may be respectively fixed to at least one of the braid layer 51 or the inner layer 22 at the proximal end position 15a of the curved region 15, or the distal end of the winding wire 52 may be disposed at the proximal end position 15a of the curved region 15, and the first hollow tube 31 and the second hollow tube 32 may not be constrained by the winding wire 52 on a further distal end side than the proximal end position 15a.

At the intermediate part 12 and the proximal end part 13 in the axial direction of the medical device body 10, the first operating line 41 and the second operating line 42 are disposed at positions that face each other in the circumferential direction of the medical device body 10.

In the case of the present embodiment, for example, as shown in FIG. 2, at the intermediate part 12 of the medical device body 10, the first operating line 41 and the second operating line 42 face each other by 180 degrees in the circumferential direction of the medical device body 10 with the axis of the medical device body 10 as a reference. Similarly, even at the proximal end part 13 of the medical device body 10 and the proximal end position 15a of the curved region 15, the first operating line 41 and the second operating line 42 face each other by 180 degrees in the circumferential direction of the medical device body 10. That is, at the intermediate part 12, the proximal end part 13, and the proximal end position 15a of the curved region 15, the phase difference between the first operating line 41 and the second operating line 42 in the circumferential direction of the medical device body 10 is 180 degrees.

The phase difference between the first operating line 41 and the second operating line 42 in the circumferential direction of the medical device body 10 decreases gradually toward the distal end side in the curved region 15, and at the distal end position 15b of the curved region 15, for example, the phase difference is about 0. In the case of the present embodiment, the first operating line 41 and the second operating line 42 are rotated by 90 degrees in the circumferential direction of the medical device body 10 in the curved region 15.

However, the fact that the first operating line 41 and the second operating line 42 disposed at positions that face each other in the circumferential direction of the medical device body 10 is not limited to this example, and means that the first operating line 41 and the second operating line 42 are spaced apart from each other by 120 degrees or more in the circumferential direction of the medical device body 10.

Additionally, in the case of the present embodiment, at the intermediate part 12, the proximal end part 13, and the proximal end position 15a of the curved region 15 in of the medical device body 10, the first hollow tube 31 and the second hollow tube 32 face each other 180 degrees in the circumferential direction of the medical device body 10 with the axis of the medical device body 10 as a reference. That is, at the intermediate part 12, the proximal end part 13, and the proximal end position 15a of the curved region 15, the phase difference between the first hollow tube 31 and the second hollow tube 32 in the circumferential direction of the medical device body 10 is 180 degrees. The phase difference decreases gradually toward the distal end side in the curved region 15.

The distal end part 11 of the medical device body 10 is provided with a ring-shaped marker 70 made of a radiopaque metallic material.

The marker 70 is disposed coaxially with the lumen 21 and around the lumen 21.

The marker 70 is disposed, for example, around the braid layer 51.

The distal end 41a of the first operating line 41 is fixed to the marker 70 by the first fixing part 71 that is, for example, spot-shaped solder.

Similarly, the distal end 42a of the second operating line 42 is fixed to the marker 70 by the first fixing part 71 that is, for example, spot-shaped solder.

The first fixing part 71 and the second fixing part 72 are disposed, for example, at the end part of the marker 70 on the proximal end side.

In the case of the present embodiment, the distal end 41a of the first operating line 41 and the distal end 42a of the second operating line 42 are coupled to each other. That is, the distal ends of the first operating line 41 and the second operating line 42 are coupled to each other.

More specifically, the first fixing part 71 and the second fixing part 72 are adjacent to and in contact with each other. That is, the first fixing part 71 and the second fixing part 72 are integrated with each other.

In addition, the distal end 41a and the distal end 42a may be fixed to the marker 70 by a single fixing part.

Next, the hub 90 provided at the proximal end part of the medical device body 10 will be described with reference to FIGS. 6 and 7.

The hub 90 has the coupling part 93 for inserting an injector (syringe), which is not shown, from the proximal end of the hub 90. The thread groove is formed at an outer periphery of the coupling part 93 so that the syringe can be detachably fixed.

The two wing parts 92, which face each other via the axis of the hub 90, are provided at the outer periphery of the hub 90. The proximal end part of the medical device body 10 is inserted into and fixed to the distal end part of the hub 90. Accordingly, the lumen 21 inside the medical device body 10 and the internal space of the hub 90 communicate with each other.

By rotating the wing parts 92 about the axis of the hub 90, a torque operation for rotates of the entire medical device body 10 about an axis is possible.

The housing 86 of the bending operating part 80 to be described below is connected and fixed to the distal end side of the hub 90.

Next, the bending operating part 80 provided in the medical device 100 will be described with reference to FIGS. 6 and 7.

The medical device 100 includes the bending operating part 80 for performing the bending operation of the distal end part 11 of the medical device body 10 by pulling the first operating line 41 and the second operating line 42.

The bending operating part 80 is configured to include the rotating member 81 that is rotatably journaled and is engaged with the first operating line 41 and the second operating line 42, and to which the proximal end part of the first operating line 41 and the proximal end part of the second operating line 42 are fixed, and the moving mechanism that moves the rotating member 81 in the pulling direction in which the first operating line 41 and the second operating line 42 are pulled, and the direction opposite to the pulling direction.

The rotating member 81 is, for example, a pulley.

Here, in the present specification, "a certain member is rotatable" includes not only an aspect in which the member is rotatable 360 degrees or more but also an aspect in which only oscillation in a predetermined angle range of less than 360 degrees is possible.

As shown in FIG. 6, the rotating member 81 has the engaging part formed in a circular shape centered on the rotation center of the rotating member 81, and the first operating line 41 and the second operating line 42 are engaged with the engaging part. In addition, the engaging part of the rotating member 81 is not limited to the circular shape, and may have a circular shape.

In this way, the rotating member 81 has the engaging part that is engaged with the first operating line 41 and the second operating line, and the engaging part is formed in a circular shape or circular-arc shape centered on the rotation center of the rotating member 81.

The moving mechanism is configured to include the forward/backward movable member 82 and the pinion 83.

The forward/backward movable member 82 includes the holding part 82a that rotatably holds the rotating member 81, and the rod-shaped part 82b that extends from the holding part 82a to the proximal end side of the medical device body 10.

The rack part 82c is formed in the rod-shaped part 82b.

The bending operating part 80 further includes the housing 86 that is a body part of the bending operating part 80, the dial operating part 84 rotatably journaled to the housing 86, the pinion 83 provided integrally with the dial operating part 84, and the guide 85 (for example, the pair of front and rear guides 85) that is provided on the inner surface of the housing 86 to guide the rod-shaped part 82b in the longitudinal direction of the rod-shaped part 82b.

The proximal end part 13 of the medical device body 10 is guided to the proximal end side of the housing 86 through the inside of the housing 86, and is inserted into and fixed to the distal end part of the hub 90.

The rotating shaft of the dial operating part 84 extends in the direction orthogonal to the axis direction of the medical device body 10 within the housing 86. The pinion 83 is formed integrally with the dial operating part 84 on one face side of the dial operating part 84, and is disposed coaxially with the rotational axis of the dial operating part 84.

The gear at the outer periphery of the pinion 83 meshes with the gear of the rack part 82c of the forward/backward movable member 82.

At least a portion of the dial operating part 84 is exposed to the outside of the housing 86 so that the operation in which an operator who performs the operation of the medical device 100 rotates the dial operating part 84 can be performed from the outside of the housing 86.

The entire rotating member 81 is housed in the housing 86. That is, the bending operating part 80 includes the housing 86, and the entire rotating member 81 is housed in the housing 86.

The first operating line 41 and the second operating line 42 are delivered from the medical device body 10 within the housing 86.

The proximal end part of the first operating line 41 is wound around the rotating member 81, for example, by one and a half turns, and the proximal end of the first operating line 41 is fixed to the rotating member 81 by the first fixing part 81a (FIG. 6).

Similarly, the second operating line 42 is wound around the rotating member 81, for example, by one and a half turns, and the proximal end of the second operating line 42 is fixed to the rotating member 81 by the second fixing part 81b (FIG. 6).

The winding direction of the first operating line 41 and the winding direction of the second operating line 42 around the rotating member 81 are mutually opposite directions. For this reason, the rotational angle of the rotating member 81 is autonomously adjusted to an angle at that the tension of the first operating line 41 and the tension of the second operating line 42 are balanced with each other.

As an operator who performs the operation of the medical device 100 grips the housing 86 or the hub 90 to rotate the dial operating part 84, the pinion 83 integral with the dial operating part 84 rotates about an axis. Along with this, the forward/backward movable member 82 having the rack part 82c moves forward (moves to the distal end side of the medical device body 10) or moves backward (moves to the proximal end side of the medical device body 10) in the axial direction of the medical device body 10 relative to the housing 86.

In FIG. 6, by rotating the dial operating part 84 in the clockwise direction, the forward/backward movable member 82 and the rotating member 81 moves backward, and both of the first operating line 41 and the second operating line 42 are pulled to the proximal end side of the medical device body 10.

In this way, the operation receiving part (dial operating part 84) is journaled in a rotationally operable manner, the moving mechanism includes the pinion 83 provided integrally and coaxially with the operation receiving part, and the rack member (forward/backward movable member 82) that moves forward and backward in an interlocking manner with the rotation of the pinion 83, and the rotating member 81 is journaled to the rack member.

In this way, the first operating line 41 and the second operating line 42 are pulled at a time by the operation on the bending operating part 80.

Here, "the first operating line 41 and the second operating line 42 are pulled at a time" means that a timing when both of the first operating line 41 and the second operating line 42 are pulled is present, and is not limited to timings when pulling is started by the first operating line 41 and the second operating line 42 being the same, and is not limited to timings when pulling is ended by the first operating line 41 and the second operating line 42 being the same.

For example, as shown in FIG. 8(a), when the distal end part 11 of the medical device body 10 has a linear shape, both of the first operating line 41 and the second operating line 42 are pulled to the proximal end side of the medical device body 10 if the dial operating part 84 is rotated in the clockwise direction in FIG. 8(b). Therefore, the distal end part 11 of the medical device body 10 is bent in one direction.

In addition, if the dial operating part 84 is rotated in the counterclockwise direction from the state of FIG. 8(b), the forward/backward movable member 82 and the rotating member 81 move forward, and the tension of the first operating line 41 and the second operating line 42 is released. Therefore, the distal end part 11 of the medical device body 10 is allowed to return linearly.

In this way, in the case of the present embodiment, the bending operating part 80 is configured to receive the operation performed by a user with the rotating mechanism (dial operating part 84) and convert a force applied to the rotating mechanism by this operation into a forward/backward movement in the axial direction of the medical device body 10 with the conversion mechanism constituted of the pinion 83 and the rack (rack part 82c).

Next, examples of the materials of the respective units of the medical device 100 will be described.

As the materials of the inner layer 22, for example, resin materials, such as polytetrafluoroethylene (PTFE), polyvinylidene fluoride (PVDF), and perfluoroalkoxy fluororesin (PFA), can be used.

As the materials of the outer layer 23, in addition to polyimide (PI), polyamide imide (PAI), and polyethylene terephthalate (PET), resin materials, such as polyethylene (PE), polyamide (PA), nylon elastomer, polyurethane (PU), ethylene-vinyl acetate resin (EVA), polyvinyl chloride (PVC), or polypropylene (PP), can be used.

As the materials of the first hollow tube 31 and the second hollow tube 32, for example, resin materials, such as polytetrafluoroethylene (PTFE), polyvinylidene fluoride (PVDF), and perfluoroalkoxy fluororesin (PFA), can be used.

Although metallic materials, such as stainless steel and tungsten, are preferable as the materials of the wire that constitutes the braid layer 51, the materials of the wire may be, for example, resin materials.

Although the metallic materials, such as stainless steel and tungsten, are preferable as the materials of the wire that constitutes the winding wire 52, the materials of the wire may be, for example, resin materials.

According to the medical device 100 related to Embodiment 2-1 as described above, the distal end part 11 of the medical device body 10 can be bent by pulling both of the first operating line 41 and the second operating line 42. In that case, the load for pulling the distal end part 11 of the medical device body 10 with the first operating line 41, and the load for pulling the distal end part 11 with the second operating line 42 can be balanced with each other. Therefore, the occurrence of the phenomenon in which the medical device body 10 rotates around the axis such that the first operating line 41 or the second operating line 42 tends to take a shortcut can be limited.

Therefore, it is possible to more reliably bend the distal end part 11 of the medical device body 10 in a desired direction.

Embodiment 2-2

Next, the medical device 100 related to Embodiment 2-2 will be described with reference to FIG. 9 to FIG. 11(b).

FIG. 11(a) and FIG. 11(b) are schematic views for showing a bending motion when the distal end part 11 of the medical device body 10 is seen in the direction of arrow A of FIG. 10, FIG. 11(a) shows a state before the bending, and FIG. 11(b) shows a bent state.

The medical device 100 related to the present embodiment is different from the medical device 100 related to the above Embodiment 2-1 in terms of points to be described below, and is configured similarly to the medical device 100 related to the above Embodiment 2-1 in terms of the other points.

In the case of the present embodiment, the parallel region 16 where the first operating line 41 and the second operating line 42 extend in parallel close to each other is formed between a distal end (distal end position 15b) of the curved region 15, and the distal ends 41a and 42a of the first operating line 41 and the second operating line 42.

That is, the medical device body 10 is configured to include the resin tube 20 having the lumen 21, the first operating line 41 and the second operating line 42 are inserted around the lumen 21 of the resin tube 20, the first operating line 41 and the second operating line 42 are close to each other at a distance smaller than the thickness of the resin tube 20, at the distal end (distal end position 15b) of the curved region 15 curved such that the first operating line 41 and the second operating line 42 approach each other in the circumferential direction of the medical device body 10 gradually toward the distal end side, and the parallel region 16 where the first operating line 41 and the second operating line 42 extend in parallel close to each other is formed between the distal end (distal end position 15b) of the curved region 15, and the distal ends 41a and 42a of the first operating line 41 and the second operating line 42.

In the parallel region 16, the first hollow tube 31 and the second hollow tube 32 extend in parallel in abutment with or close to each other.

More specifically, in the case of the present embodiment, the medical device 100 further includes an annular member 60 buried in the resin tube 20 at the distal end part of the curved region 15.

The annular member 60 is configured to have a rigidity higher than the resin tube 20, and have an external diameter smaller than the thickness of the resin tube 20 (refer to FIG. 10).

Also, the first operating line 41 and the second operating line 42 are inserted through the annular member 60.

Accordingly, the fluctuations of the paths of the first operating line 41 and the second operating line 42 can be more reliably limited.

More specifically, in the case of the present embodiment, the first hollow tube 31 and the second hollow tube 32 are inserted through the annular member 60.

That is, the medical device body 10 is buried in the resin tube 20, and are configured to include the first hollow tube 31 and the second hollow tube 32 through which the first operating line 41 and the second operating line 42 are respectively inserted, the first hollow tube 31 and the second hollow tube 32 are inserted through the annular member 60, and in the curved region 15, the first hollow tube 31 and the second hollow tube 32 are curved so as to approach each other in the circumferential direction of the medical device body 10 gradually toward the distal end side.

Although the materials of the annular member 60 are not particularly limited, the annular member 60 can be made of, for example, metal or hard resin.

Even in the case of the present embodiment, by pulling both of the first operating line 41 and the second operating line 42, the distal end part 11 of the medical device body 10 can be bent as shown in FIG. 11(a) and FIG. 11(b).

In this case, the bending angle in the parallel region 16 becomes steeper than the bending angle in the curved region 15.

As an example, the distance (the distance L2 shown in FIG. 9) from the distal end (distal end position 15b) of the curved region 15 to the distal ends 41a and 42a of the first operating line 41 and the second operating line 42 in the axial direction of the medical device body 10 is longer than the distance (the distance L1 shown in FIG. 9) from the proximal end (proximal end position 15a) of the curved region 15 to the distal end (distal end position 15b) thereof.

By virtue of such a configuration, the distal end part 11 can be more easily bent.

Additionally, the bending of the distal end part 11 can be caused mainly in the parallel region 16. For this reason, the friction between the first operating line 41 and the first hollow tube 31 in the curved region 15 and the friction between the second operating line 42 and the second hollow tube 32 can be substantially uniformly maintained irrespective of the bending angle of the distal end part 11. Therefore, the magnitude of a force required for pulling the first operating line 41 and the second operating line 42 can be substantially uniformly maintained irrespective of the bending angle of the distal end part 11.

Additionally, as another example, the distance (distance L1 shown in FIG. 9) from the proximal end (proximal end position 15a) of the curved region 15 to the distal end (distal end position 15b) thereof in the axial direction of the medical device body 10 is longer than the distance (distance L2 shown in FIG. 9) from the distal end (distal end position 15b) of the curved region 15 to the distal ends 41a and 42a of the first operating line 41 and the second operating line 42.

By virtue of such a configuration, the flexibility of the distal end part 11 can be limited to some extent.

Additionally, the curving of the first operating line 41, the second operating line 42, the first hollow tube 31, and the second hollow tube 32 in the curved region 15 can be made gentle. Therefore, the friction between the first operating line 41 and the first hollow tube 31 in the curved region 15 and the friction between the second operating line 42 and the second hollow tube 32 can be reduced.

Additionally, the length region where the first hollow tube 31 and the second hollow tube 32 translate close to each other in the distal end part 11 of the medical device body 10, that is, the length region with high rigidity is high becomes short. Therefore, excellent selectivity (excellent blood vessel selectivity or the like) when the distal end part 11 of the medical device body 10 is bent and is made to enter a branched body cavity can be obtained.

In addition, the distance L1 and the distance L2 may be the same. In this case, the smoothness of the pulling of the first operating line 41 and the second operating line 42 and the excellent selectivity when the distal end part 11 of the medical device body 10 is bent and is made to enter a branched body cavity can be obtained in a well-balanced manner.

Embodiment 2-3

Next, the medical device 100 related to Embodiment 2-3 will be described with reference to FIG. 12 to FIG. 18(c).

FIG. 16(a) and FIG. 16(b) are schematic views for showing the bending motion when the distal end part 11 of the medical device body 10 is seen in the direction of arrow A of FIG. 15, FIG. 16(a) shows the state before the bending, and FIG. 16(b) shows the bent state.

FIG. 16(c) and FIG. 16(d) are schematic views for showing the bending motion when the distal end part 11 of the medical device body 10 is seen in the direction of arrow B of FIG. 15, FIG. 16(c) shows the state before the bending, and FIG. 16(d) shows the bent state.

In FIG. 18(a), FIG. 18(b), and FIG. 18(c), the middle portion of the medical device body 10 in the longitudinal direction is broken and omitted. In the medical device body 10 shown in FIG. 18(a), FIG. 8(b), and FIG. 18(c), a portion closer to a proximal end side than the omitted portion and a portion closer to the distal end side than the omitted portion have rotational phases around the axis of the medical device body 10 that are different from each other by 90 degrees.

The medical device 100 related to the present embodiment is different from the medical device 100 related to the above Embodiment 2-2 in terms of points to be described below, and is configured similarly to the medical device 100 related to the above Embodiment 2-2 in terms of the other points.

The medical device 100 related to the present embodiment includes the third operating line 43 and the fourth operating line 44 that are inserted in the axial direction of the medical device body 10. The third operating line 43 and the fourth operating line 44 are respectively constituted of thin wires, such as metal or resin, similarly to the first operating line 41 and the second operating line 42.

The medical device body 10 further includes the third hollow tube 33 and the fourth hollow tube 34 that are buried in the resin tube 20. The third operating line 43 is inserted through the third hollow tube 33, and the fourth operating line 44 is inserted through the fourth hollow tube 34.

The third hollow tube 33 and the fourth hollow tube 34 are respectively the same sublumen tubes as the first hollow tube 31 and the second hollow tube 32, and inner cavities of these sublumen tubes are sublumens. That is, the operating lines (the third operating line 43, the fourth operating line 44) are respectively inserted through the sublumens.

The internal diameters of the third hollow tube 33 and the fourth hollow tube 34 are smaller than the internal diameter of the lumen 21.

In the case of the present embodiment, in the intermediate part 12 of the medical device body 10, the first hollow tube 31 and the third hollow tube 33 extend in parallel in abutment with or close to each other, and the second hollow tube 32 and the fourth hollow tube 34 extend in parallel in abutment with or close to each other (refer to FIG. 13).

Similarly, even at the proximal end part of the medical device body 10, the first hollow tube 31 and the third hollow tube 33 extend in parallel in abutment with or close to each other, and the second hollow tube 32 and the fourth hollow tube 34 extend in parallel in abutment with or close to each other.

In the curved region 15 of the distal end part 11 of the medical device body 10, the third hollow tube 33 and the fourth hollow tube 34 are curved so as to approach each other in the circumferential direction of the medical device body 10 gradually toward the distal end side. Accordingly, the third operating line 43 within the third hollow tube 33 and the fourth operating line 44 within the fourth hollow tube 34 are curved so as to approach each other in the circumferential direction of the medical device body 10 gradually toward the distal end side.

The direction in which the third hollow tube 33 and the third operating line 43 are curved in the curved region 15 is a direction symmetrical to the direction in which the first hollow tube 31 and the first operating line 41 are curved.

Similarly, the direction in which the fourth hollow tube 34 and the fourth operating line 44 are curved in the curved region 15 is a direction symmetrical to the direction in which the second hollow tube 32 and the second operating line 42 are curved.

In addition, the respective hollow tubes (the first hollow tube 31, the second hollow tube 32, the third hollow tube 33, and the fourth hollow tube 34) do not intersect other hollow tubes. Additionally, the respective operating lines (the first operating line 41, the second operating line 42, the third operating line 43, and the fourth operating line 44) do not intersect other operating lines.

In the parallel region 16, similarly to the first operating line 41 and the second operating line 42 extending in parallel close to each other, the third operating line 43 and the fourth operating line 44 extend in parallel close to each other.

Additionally, in the parallel region 16, similarly to the first hollow tube 31 and the second hollow tube 32 extending in parallel in abutment with or close to each other, the third hollow tube 33 and the fourth hollow tube 34 extend in parallel in abutment with or close to each other.

The distal end 43a of the third operating line 43 protrudes from the distal end of the third hollow tube 33. Similarly, the distal end 44a of the fourth operating line 44 protrudes from the distal end of the fourth hollow tube 34.

The distal end 43a of the third operating line 43 is fixed to the marker 70 by the third fixing part 73 that is, for example, spot-shaped solder (FIG. 15).

Similarly, the distal end 44a of the fourth operating line 44 is fixed to the marker 70 by the fourth fixing part 74 that is, for example, spot-shaped solder.

The third fixing part 73 and the fourth fixing part 74 are disposed, for example, at the end part of the marker 70 on the proximal end side.

The region where the third fixing part 73 and the fourth fixing part 74 are disposed, and the region where the first fixing part 71 and the second fixing part 72 are disposed face each other in the circumferential direction of the medical device body 10.

In the case of the present embodiment, the distal end 43a of the third operating line 43 and the distal end 44a of the fourth operating line 44 are coupled to each other. That is, the distal ends of the third operating line 43 and the fourth operating line 44 are coupled to each other.

More specifically, the third fixing part 73 and the fourth fixing part 74 are adjacent to and in contact with each other. That is, the third fixing part 73 and the fourth fixing part 74 are integrated with each other.

In addition, the distal end 43a and the distal end 44a may be fixed to the marker 70 by a single fixing part.

As shown in FIG. 14, in the case of the present embodiment, the medical device 100 includes the first annular member 61 buried in the resin tube 20 at the distal end part of the curved region 15 instead of the annular member 60. The first annular member 61 is the same as the annular member 60 in Embodiment 2-2, and the first hollow tube 31 and the second hollow tube 32 are inserted through the first annular member 61.

Moreover, in the case of the present embodiment, the medical device 100 includes the second annular member 62 buried in the resin tube 20 at the distal end part of the curved region 15. The second annular member 62 is the same as the first annular member 61. The third hollow tube 33 and the fourth hollow tube 34 are inserted through the second annular member 62.

The first annular member 61 and the second annular member 62 are disposed to face each other in the circumferential direction of the medical device body 10.

Even in the case of the present embodiment, by pulling both of the first operating line 41 and the second operating line 42, the distal end part 11 of the medical device body 10 can be bent in one direction as shown in FIG. 16(a) and FIG. 16(b).

Moreover, in the case of the present embodiment, by pulling both of the third operating line 43 and the fourth operating line 44, the distal end part 11 of the medical device body 10 can be bent in an opposite direction opposite to the above one direction as shown in FIG. 16(c) and FIG. 16.(d).

As shown in FIG. 17 and FIG. 18(a), in the case of the present embodiment, the bending operating part 80 includes the first bending operating part 180 for performing the bending operation of the distal end part 11 of the medical device body 10 by pulling the first operating line 41 and the second operating line 42, and the second bending operating part 280 for performing the bending operation of the distal end part 11 of the medical device body 10 by pulling the third operating line 43 and the fourth operating line 44.

The first bending operating part 180 includes the first rotating member 181, the first forward/backward movable member 182, a first pinion 183, the first dial operating part 184, and the first guide 185. The first rotating member 181, the first forward/backward movable member 182, the first pinion 183, the first dial operating part 184, and the first guide 185 are respectively equivalent to the rotating member 81, the forward/backward movable member 82, the pinion 83, the dial operating part 84, and the guide 85 that are described in Embodiment 2-1.

Hence, the first forward/backward movable member 182 includes the first holding part 182a, the first rod-shaped part 182b, and the first rack part 182c that are respectively equivalent to the holding part 82a, the rod-shaped part 82b, and the rack part 82c.

In Embodiment 2-1, similarly to the first operating line 41 and the second operating line 42 operating line being wound around and fixed to the rotating member 81, the first operating line 41 and the second operating line 42 operating line are wound around and fixed to the first rotating member 181.

The second bending operating part 280 includes the second rotating member 281, the second forward/backward movable member 282, the second pinion 283, the second dial operating part 284, and the second guide 285. The second rotating member 281, the second forward/backward movable member 282, the second pinion 283, the second dial operating part 284, and the second guide 285 are the same as the first rotating member 181, the first forward/backward movable member 182, the first pinion 183, the first dial operating part 184, and the first guide 185.

The second forward/backward movable member 282 includes the second holding part 282a, the second rod-shaped part 282b, and the second rack part 282c that are respectively the same as the first holding part 182a, the first rod-shaped part 182b, and the first rack part 182c.

Similarly to the first operating line 41 and the second operating line 42 being wound around and fixed to the first rotating member 181, the third operating line 43 and the fourth operating line 44 are wound around and fixed to the second rotating member 281.

For example, the second bending operating part 280 is disposed vertically symmetrically with respect to the first bending operating part 180 in FIG. 17.

In the case of the present embodiment, by rotating the first dial operating part 184 to move the first forward/backward movable member 182 and the first rotating member 181 backward, the first operating line 41 and the second operating line 42 can be pulled to bend the distal end part 11 of the medical device body 10 in one direction (FIG. 18(b)).

Additionally, by rotating the second dial operating part 284 to move the second the forward/backward movable member 282 and the second rotating member 281, the third operating line 43 and the fourth operating line 44 can be pulled to bend the distal end part 11 of the medical device body 10 in the direction opposite respect to the above one direction (FIG. 18(c)).

In this way, in the case of the present embodiment, the medical device 100 includes the second bending operating part 280 for performing the bending operation of the distal end part 11 of the medical device body 10 in a direction different from the direction of the bending of the distal end part 11 of the medical device body 10 by the pulling of the first operating line 41 and the second operating line 42, by pulling the third operating line 43 and the fourth operating line 44.

At the intermediate part 12 and the proximal end part in the axial direction of the medical device body 10, the third operating line 43 and the fourth operating line 44 extend in parallel so as to be spaced apart from each other in the circumferential direction of the medical device body 10, and at the distal end part 11 in the axial direction of the medical device body 10, the third operating line 43 and the fourth operating line 44 are curved and joined together so as to approach each other in the circumferential direction of the medical device body 10 gradually toward the distal end side.

Additionally, the third operating line 43 and the fourth operating line 44 are pulled at a time by the operation on the second bending operating part 280.

The second bending operating part 280 includes the second rotating member 281 that is rotatably journaled and to which the proximal end part of the third operating line 43 and the proximal end part of the fourth operating line 44 are fixed, the second moving mechanism that moves the second rotating member 281 in a second pulling direction in which the third operating line 43 and the fourth operating line 44 are pulled, and an opposite direction opposite to the second pulling direction, and the second operation receiving part (for example, the second dial operating part 284) that operates in response to a user's (operator's) operation. Then, as the power of the second operation receiving part is transmitted to the second rotating member 281 via the second moving mechanism, the second rotating member 281 is adapted to move in the second pulling direction and the direction opposite to the second pulling direction.

In addition, in the case of the present embodiment, the second pulling direction is the same direction as the above pulling direction.

More specifically, the third operating line 43 and the fourth operating line 44 are engaged with the second rotating member 281, and the proximal end part of the third operating line 43 and the proximal end part of the fourth operating line 44 are fixed to the second rotating member 281.

As described above, the bending operating part 80 includes the housing 86. Also, the entire rotating member (first rotating member 181) and the entire second rotating member 281 are housed in the housing 86.

The second rotating member 281 has the second engaging part that is engaged with the third operating line 43 and the fourth operating line 44, and the second engaging part is formed in a circular shape or circular-arc shape centered on the rotation center of the second rotating member 281.

The second operation receiving part (second dial operating part 284) is journaled in a rotationally operable manner, and the second moving mechanism includes the second pinion 283 provided integrally and coaxially with the second operation receiving part, and the second rack member (second forward/backward movable member 282) that moves forward and backward in an interlocking manner with the rotation of the second pinion 283, and the second rotating member 281 is journaled to the second rack member.

Embodiment 2-4

Next, the medical device 100 related to Embodiment 2-4 will be described with reference to FIG. 19(*a*) and FIG. 19(*b*).

The medical device 100 related to the present embodiment is different from the medical device 100 related to the above Embodiment 2-1 in terms of points to be described below, and is configured similarly to the medical device 100 related to the above Embodiment 2-1 in terms of the other points.

In the case of the present embodiment, the easily bendable part 110 in which the flexibility of the medical device body 10 is locally high is formed in the region between the first operating line 41 and the second operating line 42 in the circumferential direction of the distal end part 11 of the medical device body 10 or the region located opposite to the region with respect to the axis of the medical device body 10.

Accordingly, since the flexibility of the distal end part 11 is improved, the tension acting on the first operating line 41 and the second operating line 42 during the bending operation can be reduced. Hence, the occurrence of the phenomenon in which the medical device body 10 rotates around the axis such that the first operating line 41 or the second operating line 42 tends to take a shortcut can be limited.

More specifically, as shown in FIG. 19(*b*), the easily bendable parts 110 are formed both in the region between the first operating line 41 and the second operating line 42 in the circumferential direction of the distal end part 11 of the medical device body 10 or the region located opposite to the region with respect to the axis of the medical device body 10.

Accordingly, the flexibility of the distal end part 11 is further improved.

The easily bendable part 110 is configured to include the notched part 111 formed on the outer surface side of the medical device body 10.

The notched part 111 can be formed in, for example, a shape gouged out in an arc as shown in FIG. 19(*b*).

Accordingly, the distal end part 11 can be more steeply bent.

Embodiment 2-5

Next, the medical device 100 related to Embodiment 2-5 will be described with reference to FIG. 20(*a*) and FIG. 20(*b*).

The medical device 100 related to the present embodiment is different from the medical device 100 related to the above Embodiment 2-1 in terms of points to be described below, and is configured similarly to the medical device 100 related to the above Embodiment 2-1 in terms of the other points.

In the case of the present embodiment, an easily bendable part 110 in which the flexibility of the medical device body 10 is locally high is formed in the region between the first operating line 41 and the second operating line 42 in the circumferential direction of the distal end part 11 of the medical device body 10 or the region located opposite to the region with respect to the axis of the medical device body 10.

Accordingly, since the flexibility of the distal end part 11 is improved, the tension acting on the first operating line 41 and the second operating line 42 during the bending operation can be reduced. Hence, the occurrence of the phenomenon in which the medical device body 10 rotates around the axis such that the first operating line 41 or the second operating line 42 tends to take a shortcut can be limited.

More specifically, as shown in FIG. 20(*b*), the easily bendable part 110 is formed in the region between the first operating line 41 and the second operating line 42 in the circumferential direction of the distal end part 11 of the medical device body 10 or the easily bendable part 110 is not formed in the region located opposite to the region with respect to the axis of the medical device body 10.

However, the easily bendable parts 110 may be formed both in the region between the first operating line 41 and the second operating line 42 in the circumferential direction of the distal end part 11 of the medical device body 10 or the region located opposite to the region with respect to the axis of the medical device body 10.

The easily bendable part 110 is configured to include the notched part 111 formed on the outer surface side of the medical device body 10.

In the case of the present embodiment, the medical device body 10 has the plurality of notched parts 111 disposed adjacent to each other in the axial direction of the medical device body 10. The notched parts 111 are elongated in the circumferential direction of the medical device body 10, and the sectional shape thereof is a wedge shape.

In the case of the present embodiment, the distal end part 11 of the medical device body 10 is easily bent in the initial stage of the bending. However, if a certain amount of bending angle is reached, wedge-shaped inclined surfaces come in contact with each other, so that further bending becomes difficult (if a certain amount of bending angle is reached, rigidity becomes high).

For this reason, since the distal end part 11 of the medical device body 10 has excellent deformation resistance against compression in the axial direction when being pushed into a body cavity, the blood-vessels selectivity of the medical device 100 is excellent.

Embodiment 2-6

Next, Embodiment 2-6 will be described with reference to FIG. 21.

The medical device 100 related to the present embodiment is different from the medical device 100 related to the above Embodiment 2-3 in terms of points to be described below, and is configured similarly to the medical device 100 related to the above Embodiment 2-3 in terms of the other points.

In the case of the present embodiment, as will be described below, the configuration of the bending operating part 80 is different from the above Embodiment 2-3.

In the case of the present embodiment, the bending operating part 80 includes the housing 86, the first rotating member 181 (rotating member), the second rotating member 281, the dial operating part 194 (third rotating member), the first coupling wire 192 that couples the first rotating member 181 and the dial operating part 194 to each other, and the second coupling wire 193 that couples the second rotating member 281 and the dial operating part 194 to each other.

Each of the first rotating member 181 and the second rotating member 281 is, for example, a pulley.

The rotating shaft of the first rotating member 181 extends, for example, in a direction orthogonal to the axis direction (leftward-rightward direction in FIG. 21) of the medical device body 10 within the housing 86.

The rotating shaft of the first rotating member 181 is held by the housing 86 so as to be rotatable around the axis of the rotating shaft and movable relative to the housing 86 in the axis direction (leftward-rightward direction in FIG. 21) of the medical device body 10 within the housing 86. For example, the rotating shaft of the first rotating member 181 is journaled by an elongated hole (not shown) formed in the housing 86.

Similarly, the rotating shaft of the second rotating member 281 extends, for example, in the direction orthogonal to the axis direction of the medical device body 10 within the housing 86. The rotating shaft of the second rotating member 281 is held by the housing 86 so as to be rotatable around the axis of the rotating shaft and movable relative to the housing 86 in the axis direction (leftward-rightward direction in FIG. 21) of the medical device body 10 within the housing 86.

As an example, the rotating shaft of the first rotating member 181 and the rotating shaft of the second rotating member 281 are parallel to each other. However, these rotating shafts may not be parallel to each other.

The first operating line 41, the second operating line 42, the third operating line 43, and the fourth operating line 44 are delivered from the medical device body 10 within the housing 86.

The proximal end part of the first operating line 41 is wound around the first rotating member 181, for example, by one and a half turns, and the proximal end of the first operating line 41 is fixed to the first rotating member 181. Similarly, the second operating line 42 is wound around the first rotating member 181, for example, by one and a half turns, and a proximal end of the second operating line 42 is fixed to the first rotating member 181. The winding direction of the first operating line 41 and the winding direction of the second operating line 42 around the first rotating member 181 are mutually opposite directions. For this reason, the rotational angle of the first rotating member 181 is autonomously adjusted to an angle at which the tension of the first operating line 41 and the tension of the second operating line 42 are balanced with each other.

The proximal end part of the third operating line 43 is wound around the second rotating member 281, for example, by one and a half turns, and the proximal end of the third operating line 43 is fixed to the second rotating member 281. Similarly, the fourth operating line 44 is wound around the second rotating member 281, for example, by one and a half turns, and the proximal end of the fourth operating line 44 is fixed to the second rotating member 281. The winding direction of the third operating line 43 and the winding direction of the fourth operating line 44 around the second rotating member 281 are mutually opposite directions. For this reason, the rotational angle of the second rotating member 281 is autonomously adjusted to an angle at which the tension of the third operating line 43 and the tension of the fourth operating line 44 are balanced with each other.

The dial operating part 194 is rotatably journaled to the housing 86. The rotating shaft of the dial operating part 194 extends in the direction orthogonal to the axis direction of the medical device body 10 within the housing 86.

As an example, the rotating shaft of the dial operating part 194 is parallel to the rotating shaft of the first rotating member 181 and the rotating shaft of the second rotating member 281. However, the rotating shaft of the dial operating part 194 may not be parallel to the rotating shaft of the first rotating member 181 and the rotating shaft of the second rotating member 281.

At least a portion of the dial operating part 194 is exposed to the outside of the housing 86 so that the operation in which an operator who performs the operation of the medical device 100 rotates the dial operating part 194 can be performed from the outside of the housing 86.

The dial operating part 194 includes, for example, the body part formed in a disk shape, and the winding part 191 fixed to one surface side of the body part.

The winding part 191 is, for example, a cylindrical bobbin. The winding part 191 is disposed coaxially with the rotating shaft of the dial operating part 194.

The distal end of the first coupling wire 192 is coupled to the rotating shaft of the first rotating member 181. The proximal end part of the first coupling wire 192 is wound around the winding part 191, for example, by one and a half turns, and the proximal end of the first coupling wire 192 is fixed to the winding part 191 in a first coupling region 195.

Similarly, the distal end of the second coupling wire 193 is coupled to the rotating shaft of the second rotating member 281. The proximal end part of the second coupling wire 193 is wound around the winding part 191, for example, by one and a half turns, and the proximal end of the second coupling wire 193 is fixed to the winding part 191 in a second coupling region 196.

The winding direction of the first coupling wire 192 and the winding direction of the second coupling wire 193 around the winding part 191 are mutually opposite directions.

In the case of the present embodiment, as an operator who performs the operation of the medical device 100 grips the housing 86 or the hub 90 to rotate the dial operating part 194, the first coupling wire 192 or the second coupling wire 193 is selectively wound around the winding part 191. Therefore, the first rotating member 181 or the second rotating member 281 is selectively pulled to the proximal end side.

That is, when the operation of rotating the dial operating part 194 in the clockwise direction in FIG. 21 is performed, the first coupling wire 192 is wound around the winding part 191. Therefore, the first rotating member 181 is pulled to the proximal end side. Therefore, since both of the first operating line 41 and the second operating line 42 are pulled to the proximal end side of the medical device body 10, the distal end part 11 of the medical device body 10 is bent in one direction.

Additionally, when the operation of rotating the dial operating part 194 in the counterclockwise direction in FIG. 21 is performed, the second coupling wire 193 is wound around the winding part 191. Therefore, the second rotating member 281 is pulled to the proximal end side. Therefore, since both of the third operating line 43 and the fourth operating line 44 are pulled to the proximal end side of the medical device body 10, the distal end part 11 of the medical device body 10 is bent in the above one direction.

That is, the operation of pulling both of the first operating line 41 and the second operating line 42 and the operation of pulling both of the third operating line 43 and the fourth operating line 44 can be performed by the operation on one dial operating part 194.

In this way, the medical device 100 related to the present embodiment includes the third operating line 43 and the fourth operating line 44 that are inserted in the axial direction of the medical device body 10, and the operation on the bending operating part 80 allows the third operating line 43 and the fourth operating line 44 to be pulled and allows the distal end part 11 of the medical device body 10 to be bent in a direction different from the bending direction of the distal end part 11 of the medical device body 10 by the pulling of the first operating line 41 and the second operating line 42.

More specifically, the bending operating part 80 further includes the second rotating member 281 and the third rotating member (dial operating part 194) that are rotatably journaled, in addition to the rotating member (first rotating member 181), the rotating shaft of the rotating member is coupled to the first coupling region 195 in the third rotating member, and the rotating shaft of the second rotating member 281 is coupled to the second coupling region 196 in the third rotating member.

Additionally, the proximal end part of the first operating line 41 and the proximal end part of the second operating line 42 are fixed to the rotating member, and the proximal end part of the third operating line 43 and the proximal end part of the fourth operating line 44 are fixed to the second rotating member 281.

Then, as the third rotating member rotates in one direction, the rotating member is pulled and the first operating line 41 and the second operating line 42 are pulled, thereby bending the distal end part 11 of the medical device body 10, and as the third rotating member rotates in the direction opposite to the above one direction, the second rotating member 281 is pulled and the third operating line 43 and the fourth operating line 44 are pulled, thereby bending the distal end part 11 of the medical device body 10 in the direction (for example, opposite direction) different from the pulling direction of the distal end part 11 of the medical device body 10 by the pulling of the first operating line 41 and the second operating line 42.

In addition, in Embodiment 2-6, an example in which the rotating shaft of the rotating member (first rotating member 181) is coupled to the third rotating member (dial operating part 194) via a wire (first coupling wire 192) and the rotating shaft of the second rotating member 281 is coupled to the third rotating member via a wire (second coupling wire 193) has been described. However, the invention is not limited to this example.

For example, the rotating shaft of the rotating member may be directly journaled to the first coupling region in the third rotating member, and the rotating shaft of the second rotating member 281 may be journaled to the second coupling region in the third rotating member. In this case, the third coupling member does not need to include the above winding part 191.

Embodiment 2-7

Next, Embodiment 2-7 will be described with reference to FIG. 22.

The medical device 100 related to the present embodiment is different from the medical device 100 related to the above Embodiment 2-6 in terms of points to be described below, and is configured similarly to the medical device 100 related to the above Embodiment 2-6 in terms of the other points.

In the case of the present embodiment, as will be described below, the configuration of the bending operating part 80 is different from the above Embodiment 2-6.

In the case of the present embodiment, the bending operating part 80 does not include the winding part 191, the first coupling wire 192, and the second coupling wire 193 that are shown in FIG. 21. Instead of this, the bending operating part 80 includes the pinion 197, the first rack member 198, the second rack member 199, and the guide 200 that are shown in FIG. 22.

The pinion 197 is formed integrally with the dial operating part 194 on one surface of the disk-shaped dial operating part 194, and is disposed coaxially with the rotating shaft of the dial operating part 194.

The first rack member 198 is a rod-shaped member that extends in the axis direction of the medical device body 10 within the housing 86. The first rotating member 181 (rotating member) is rotatably journaled to the distal end part of the first rack member 198. The rack, which meshes with the gear at the outer periphery of the pinion 197, is formed on one side surface of the first rack member 198. The bending operating part 80 includes, for example, the pair of front and rear guides 200 that are provided corresponding to the first rack member 198. The first rack member 198 is linearly guided by the guides 200 so as to be linearly movable forward and backward in the axis direction of the medical device body 10 within the housing 86.

Similarly, the second rack member 199 is a rod-shaped member that extends in the axis direction of the medical device body 10 within the housing 86. The second rotating member 281 is rotatably journaled to the distal end part of the second rack member 199. The rack, which meshes with the gear at the outer periphery of the pinion 197, is formed on one side surface of the second rack member 199.

The bending operating part 80 includes, for example, the pair of front and rear guides 200 that are provided corresponding to the second rack member 199. The second rack member 199 is linearly guided by the guides 200 so as to be linearly movable forward and backward in the axis direction of the medical device body 10 within the housing 86.

Even in the case of the present embodiment, the engagement and fixation of the first operating line 41 with respect to the first rotating member 181 and the second operating line 42 and engagement and fixation of the third operating line 43 with respect to the second rotating member 281 and the fourth operating line 44 are the same as those of Embodiment 2-6.

For this reason, the rotational angle of the first rotating member 181 is autonomously adjusted to an angle at which the tension of the first operating line 41 and the tension of the second operating line 42 are balanced with each other, and the rotational angle of the second rotating member 281 is autonomously adjusted to an angle at which the tension of the third operating line 43 and the tension of the fourth operating line 44 are balanced with each other.

In the case of the present embodiment, as an operator who performs the operation of the medical device 100 grips the housing 86 or the hub 90 to rotate the dial operating part 194, the first rack member 198 or the second rack member 199, which respectively meshes with the pinion 197, selectively moves to the proximal end side.

That is, when the operation of rotating the dial operating part 194 in the clockwise direction in FIG. 22 is performed, the first rack member 198 moves (moves backward) to the proximal end side. Therefore, the first rotating member 181 is pulled to the proximal end side. Therefore, since both of the first operating line 41 and the second operating line 42 are pulled to the proximal end side of the medical device body 10, the distal end part 11 of the medical device body 10 is bent in one direction.

Additionally, when the operation of rotating the dial operating part 194 in the counterclockwise direction in FIG. 22 is performed, the second rack member 199 moves (moves backward) to the proximal end side. Therefore, the second rotating member 281 is pulled to the proximal end side. Therefore, since both of the third operating line 43 and the fourth operating line 44 are pulled to the proximal end side of the medical device body 10, the distal end part 11 of the medical device body 10 is bent in the above one direction.

In addition, the second rack member 199 moves to the proximal end side when the first rack member 198 moves to the proximal end side, and the first rack member 198 moves to the distal end side when the second rack member 199 moves to the distal end side.

In this way, in the case of the present embodiment, the bending operating part 80 includes the second rotating member 281 and the third rotating member (dial operating part 194) that are rotatably journaled, the pinion 197 provided integrally and coaxially with the third rotating member, the first rack member 198 to which the rotating shaft of the first rotating member 181 is coupled and which moves forward and backward in an interlocking manner with the rotation of the pinion 197, and the second rack member 199 to which the rotating shaft of the second rotating member 281 is coupled and which moves forward and backward always in the direction opposite to the forward/backward movement direction of the first rack member 198 in an interlocking manner with the rotation of the pinion 197, in addition to the rotating member (first rotating member 181).

The proximal end part of the first operating line 41 and the proximal end part of the second operating line 42 are fixed to the rotating member (first rotating member 181), and the proximal end part of the third operating line 43 and the proximal end part of the fourth operating line 44 are fixed to the second rotating member 281.

As the third rotating member (dial operating part 194) rotates in one direction, the first rotating member 181 is pulled via the first rack member 198 and the first operating line 41 and the second operating line 42 are pulled, thereby bending the distal end part 11 of the medical device body 10.

Additionally, as the third rotating member rotates in the direction opposite to the above one direction, the second rotating member 281 is pulled via the second rack member 199 and the third operating line 43 and the fourth operating line 44 are pulled, thereby bending the distal end part 11 of the medical device body 10 in the direction different from the bending direction of the distal end part 11 of the medical device body 10 by the pulling of the first operating line 41 and the second operating line 42.

Although the respective embodiments have been described above with reference to the drawings, these are examples of the invention, and various configurations other than the above can also be adopted.

An example in which the rotating mechanism of the bending operating part 80 is the dial operating part 84 has been described in the above Embodiment 2-1. However, the rotating mechanism of the bending operating part 80 may be others (for example, a rotary lever or the like) than the dial operating part 84.

Additionally, an example in which the conversion mechanism of the bending operating part 80 is configured to include the rack (rack part 82c) and the pinion 83 has been described in the above Embodiment 2-1. However, the bending operating part 80 may be configured to include other conversion mechanisms (for example, a cam, a link mechanism, a pin, a guide with a groove, or the like).

The same applies to the other embodiments.

Additionally, an example in which the first operating line 41 and the second operating line 42 are constituted of separate thin lines has been described in the above respective embodiments. However, each of the first operating line 41 and the second operating line 42 may be constituted of a portion of one thin line. That is, the one thin line may be folded at the distal ends 41a and 42a.

Similarly, an example in which the third operating line 43 and the fourth operating line 44 are constituted of separate thin lines has been described above. However, each of the third operating line 43 and the fourth operating line 44 may be constituted of a portion of one thin line. That is, the one thin line may be folded at the distal ends 43a and 44a.

Additionally, an example in which the proximal end part of the first operating line 41 and the proximal end part of the second operating line 42 are individually fixed to the bending operating part 80 has been described in the above respective embodiments. However, the proximal end of the first operating line 41 and the proximal end of the second operating line 42 may be are connected to each other, and may be looped (looped in a portion engaged with the rotating member 81) in the bending operating part 80.

Similarly, an example in which the proximal end part of the third operating line 43 and the proximal end part of the fourth operating line 44 are individually fixed to the second bending operating part 280 has been described above. However, the proximal end of the third operating line 43 and the proximal end of the fourth operating line 44 may be connected to each other, and may be looped (looped in the portion engaged with the second rotating member 281) in the second bending operating part 280.

In the above Embodiment 2-3 (FIG. 17, FIG. 18(*a*), FIG. 18(*b*), FIG. 18(*c*)), an example in which the first dial operating part 184 and the second dial operating part 284 are disposed to overlap each other in the direction orthogonal to the plate surfaces thereof and the rotating shaft of the first dial operating part 184 and the rotating shaft of the second dial operating part 284 are disposed coaxially with each other has been described. However, the invention is not limited to this example.

For example, the rotating shaft of the first dial operating part 184 and the rotating shaft of the second dial operating part 284 do not need to be disposed coaxially with each other. For example, the first dial operating part 184 and the second dial operating part 284 may be disposed at positions different from each other in the axial direction of the medical device body 10.

Additionally, in the above Embodiment 2-1, an example in which the number of operating lines provided in the medical device 100 is two and two operating lines are joined together has been described. However, in the above Embodiment 2-3, an example in which the number of operating lines provided in the medical device 100 is four and these operating lines are joined together has been described.

However, the invention is not limited to this, and the medical device 100 may have a configuration in which two operating lines extend in parallel from distal ends of the operating lines to proximal ends thereof and the operating lines are not joined together. In this case, the two operating lines are disposed at positions that face each other in the circumferential direction of the medical device body 10. In this case, for example, by pulling the two operating lines in a state where the medical device 100 is made to enter a body cavity using a technique called "Over The Wire", the medical device body 10 can be stiffened, and the medical device body 10 can be held in a bent shape along the bending of the body cavity. In addition, in a case where the two operating lines extend in parallel from the distal ends of the operating lines to the proximal ends thereof, the medical device 100 may be an active catheter in which the bending operation of the distal end part 11 is allowed by the operating lines, or may be of a type in which the operating lines are used exclusively for stiffening the medical device body 10. In a case where the medical device 100 is the active catheter, the distal end part 11 is further bent in a state where the medical device body 10 is stiffened as described above. Accordingly, the occurrence of the phenomenon in which the medical device body 10 rotates around the axis such that the operating lines tend to take a shortcut can be limited. Even in this case, in a case where the number of operating lines is four, a pair of operating lines among these operating lines is disposed at positions that face each other in the circumferential direction of the medical device body 10, and the other pair of operating lines are disposed at positions that face each other in the circumferential direction of the medical device body 10. Then, by pulling two or four operating lines at a time, the medical device body 10 can be stiffened and the shape thereof can be maintained, or, the distal end part 11 can be further bent in that state.

Additionally, the above respective embodiments can be appropriately combined without departing from the spirit of the invention.

The present embodiment includes the following technical ideas.

(1) A medical device including an elongated medical device body; a first operating line and a second operating line that are inserted in an axial direction of the medical device body; and a bending operating part for performing a bending operation of a distal end part of the medical device body by pulling the first operating line and the second operating line, at an intermediate part and a proximal end part in the axial direction of the medical device body, the first operating line and the second operating line extending in parallel so as to be spaced apart from each other in a circumferential direction of the medical device body, and at a distal end part in the axial direction of the medical device body, a first operating line and a second operating line being curved and joined together so as to approach each other in the circumferential direction of the medical device body gradually toward a distal end side.

(2) The medical device according to (1) in which the first operating line and the second operating line are pulled at a time by an operation on the bending operating part.

(3) The medical device according to (1) or (2) in which distal ends of the first operating line and the second operating line are coupled to each other.

(4) The medical device according to any one of (1) to (3) in which at the intermediate part and the proximal end part in the axial direction of the medical device body, the first operating line and the second operating line are disposed at positions that face each other in the circumferential direction of the medical device body.

(5) The medical device according to any one of (1) to (4) in which the medical device body is configured to include a resin tube having a lumen, and a first hollow tube and a second hollow tube that are buried in the resin tube and allows the first operating line and the second operating line to be respectively inserted therethrough, and at the distal end part of the medical device body in the axial direction, the first hollow tube and the second hollow tube are curved so as to approach each other in the circumferential direction of the medical device body gradually toward the distal end side.

(6) The medical device according to any one of (1) to (5) in which the bending operating part is configured to include a rotating member that is rotatably journaled and is engaged with the first operating line and the second operating line, and to which a proximal end part of the first operating line and a proximal end part of the second operating line are fixed, and a moving mechanism that is configured to move the rotating member in a pulling direction in which the first operating line and the second operating line are pulled, and an opposite direction opposite to the pulling direction.

(7) The medical device according to any one of (1) to (6) in which an easily bendable part in which flexibility of the medical device body is locally high is formed in a region between the first operating line and the second operating line in the circumferential direction of the distal end part of the medical device body or a region located opposite to the region with respect to an axis of the medical device body.

(8) The medical device according to (7) in which the easily bendable part is configured to include a notched part formed on an outer surface side of the medical device body.

(9) The medical device according to any one of (1) to (8) in which the medical device body is configured to include a resin tube having a lumen, the first operating line and the second operating line are inserted around the lumen of the resin tube, and the first operating line and the second operating line are close to each other at a distance smaller than a thickness of the resin tube, at a distal end of a curved region curved such that the first operating line and the second operating line approach each other in the circumferential direction of the medical device body gradually toward the distal end side, and a parallel region where the first operating line and the second operating line extend in parallel close to each other is formed between a distal end of the curved region, and distal ends of the first operating line and the second operating line.

(10) The medical device according to (9) in which a distance from the distal end of the curved region to the distal ends of the first operating line and the second operating line is longer than a distance from a proximal end of the curved region to the distal end thereof in the axial direction of the medical device body.

(11) The medical device according to claim 9 in which a distance from a proximal end of the curved region to the distal end thereof is longer than a distance from the distal end of the curved region to the distal ends of the first operating line and the second operating line in the axial direction of the medical device body.

(12) The medical device according to any one of (9) to (11) further including an annular member buried in the resin tube at a distal end part of the curved region, the annular member is configured to have a rigidity higher than the resin tube, and have an external diameter smaller than the thickness of the resin tube, and the first operating line and the second operating line are inserted through the annular member.

(13) The medical device according to (12) in which the medical device body is configured to include a first hollow tube and a second hollow tube that are buried in the resin tube and allows the first operating line and the second operating line to be respectively inserted therethrough, the first hollow tube and the second hollow tube are inserted through the annular member, and in the curved region, the first hollow tube and the second hollow tube are curved so as to approach each other in the circumferential direction of the medical device body gradually toward the distal end side.

(14) The medical device according to any one (1) to (13) further including a third operating line and a fourth operating line that are inserted in the axial direction of the medical device body; and a second bending operating part for performing a bending operation of the distal end part of the medical device body in a direction different from a bending direction of the distal end part of the medical device body by the pulling of the first operating line and the second operating line, by pulling the third operating line and the fourth operating line, the intermediate part and the proximal end part in the axial direction of the medical device body, the third operating line and the fourth operating line extending in parallel so as to be spaced apart from each other in the circumferential direction of the medical device body, and at the distal end part in the axial direction of the medical device body, the third operating line and the fourth operating line being curved and joined together so as to approach each other in the circumferential direction of the medical device body gradually toward the distal end side.

(15) The medical device according to (14) in which the third operating line and the fourth operating line are pulled at a time by an operation on the second bending operating part.

(16) The medical device according to (6) in which the rotating member has an engaging part that is engaged with the first operating line and the second operating line, and the engaging part is formed in a circular shape or circular-arc shape centered on a rotation center of the rotating member.

(17) The medical device according to (6) or (16) in which the bending operating part includes an operation receiving part that operates in response to a user's operation, and as power of the operation receiving part is transmitted to the rotating member via the moving mechanism, the rotating member moves in the pulling direction and the opposite direction.

(18) The medical device according to (17) in which the operation receiving part is journaled in a rotationally operable manner, and the moving mechanism includes a pinion provided integrally and coaxially with the operation receiving part, and a rack member that is configured to move forward and backward in an interlocking manner with the rotation of the pinion, and the rotating member is journaled to the rack member.

(19) The medical device according to (14) or (15) in which the second bending operating part is configured to include a second rotating member that is rotatably journaled and is engaged with the third operating line and the fourth operating line, and to which a proximal end part of the third operating line and a proximal end part of the fourth operating line are fixed, and a second moving mechanism that is configured to move the second rotating member in a second pulling direction in which the third operating line and the fourth operating line are pulled, and an opposite direction opposite to the second pulling direction.

(20) The medical device according to (19) in which the second rotating member has a second engaging part that is engaged with the third operating line and the fourth operating line, and the second engaging part is formed in a circular shape or circular-arc shape centered on a rotation center of the second rotating member.

(21) The medical device according to (19) or (20) in which the second bending operating part includes a second operation receiving part that operates in response to a user's operation, and as power of the second operation receiving part is transmitted to the second rotating member via the second moving mechanism, the second rotating member is configured to move in the second pulling direction and the direction opposite to the second pulling direction.

(22) The medical device according to (21) in which the second operation receiving part is journaled in a rotationally operable manner, the second moving mechanism includes a second pinion provided integrally and coaxially with the second operation receiving part, and a second rack member that is configured to move forward and backward in an interlocking manner with the rotation of the second pinion, and the second rotating member is journaled to the second rack member.

(23) The medical device according to any one of (1) to (13) further including a third operating line and a fourth operating line that are inserted in the axial direction of the medical device body, at the intermediate part and the proximal end part in the axial direction of the medical device body, the third operating line and the fourth operating line extending in parallel so as to be spaced apart from each other in the circumferential direction of the medical device body, and at the distal end part in the axial direction of the medical device body, the third operating line and the fourth operating line being curved and joined together so as to approach each other in the circumferential direction of the medical device body gradually toward the distal end side, and an operation on the bending operating part allowing the third operating line and the fourth operating line to be pulled and allows the distal end part of the medical device body to be bent in a direction different from a bending direction of the distal end part of the medical device body by the pulling of the first operating line and the second operating line.

(24) The medical device according to (23) in which the bending operating part includes a first rotating member, a second rotating member, and a third rotating member that are rotatably journaled, a rotating shaft of the first rotating member is coupled to a first coupling region in the third rotating member, a rotating shaft of the second rotating member is coupled to a second coupling region in the third rotating member, a proximal end part of the first operating line and a proximal end part of the second operating line are fixed to the first rotating member, a proximal end part of the third operating line and a proximal end part of the fourth operating line are fixed to the second rotating member, as the third rotating member rotates in one direction, the first rotating member is pulled and the first operating line and the second operating line are pulled, thereby bending the distal end part of the medical device body, and as the third rotating member rotates in an opposite direction opposite to the one direction, the second rotating member is pulled and the third operating line and the fourth operating line are pulled, thereby bending the distal end part of the medical device body in a direction different from the bending direction of the distal end part of the medical device body by the pulling of the first operating line and the second operating line.

(25) The medical device according to (23) in which the bending operating part includes a first rotating member, a second rotating member, and a third rotating member that are rotatably journaled, a pinion provided integrally and coaxially with the third rotating member, a first rack member to which a rotating shaft of the first rotating member are coupled and which moves forward and backward in an interlocking manner with the rotation of the pinion, and a second rack member to which a rotating shaft of the second rotating member is coupled and which moves forward and backward always in an opposite direction opposite to a forward/backward movement direction of the first rack member in an interlocking manner with the rotation of the pinion, a proximal end part of the first operating line and a proximal end part of the second operating line being fixed to the first rotating member, a proximal end part of the third operating line and a proximal end part of the fourth operating line being fixed to the second rotating member, as the third rotating member rotates in one direction, the first rotating member being pulled via the first rack member and the first operating line and the second operating line are pulled, thereby bending the distal end part of the medical device body, and as the third rotating member rotates in an opposite direction opposite to the one direction, the second rotating member being pulled via the second rack member and the third operating line and the fourth operating line being pulled, thereby bending the distal end part of the medical device body in a direction different from the bending direction of the distal end part of the medical device body by the pulling of the first operating line and the second operating line.

The present embodiment includes the following technical ideas.

<1> A medical device including an elongated medical device body; a first operating line and a second operating line that are inserted in an axial direction of the medical device body; and a bending operating part for performing a bending operation of a distal end part of the medical device body by pulling the first operating line and the second operating line, the bending operating part including a rotating member that is rotatably journaled and to which a proximal end part of the first operating line and a proximal end part of the second operating line are fixed, a moving mechanism that is configured to move the rotating member in a pulling direction in which the first operating line and the second operating line are pulled, and an opposite direction opposite to the pulling direction, and an operation receiving part that operates in response to a user's operation, and the rotating member moving in the pulling direction and the opposite direction as power of the operation receiving part is transmitted to the rotating member via the moving mechanism.

<2> The medical device according to <1> in which the bending operating part includes a housing, and the entire rotating member is housed in the housing.

<3> The medical device according to <1> or (2) in which the rotating member has an engaging part that is engaged with the first operating line and the second operating line, and the engaging part is formed in a circular shape or circular-arc shape centered on a rotation center of the rotating member.

<4> The medical device according to any one of <1> to <3> in which the operation receiving part is journaled in a rotationally operable manner, the moving mechanism includes a pinion provided integrally and coaxially with the operation receiving part, and a rack member that is configured to move forward and backward in an interlocking manner with the rotation of the pinion, and the rotating member is journaled to the rack member.

<5> The medical device according to any one of <1> to <4>, further including a third operating line and a fourth operating line that are inserted in the axial direction of the medical device body; and a second bending operating part for performing a bending operation of the distal end part of the medical device body in a direction different from a bending direction of the distal end part of the medical device body by the pulling of the first operating line and the second operating line, by pulling the third operating line and the fourth operating line, the second bending operating part includes a second rotating member that is rotatably journaled and to which a proximal end part of the third operating line and a proximal end part of the fourth operating line are fixed, a second moving mechanism that is configured to move the second rotating member in a second pulling direction in which the third operating line and the fourth operating line are pulled, and an opposite direction opposite to the second pulling direction, and a second operation receiving part that operates in response to a user's operation, as power of the second operation receiving part is transmitted to the second rotating member via the second moving mechanism, the second rotating member moves in the second pulling direction and the direction opposite to the second pulling direction.

<6> The medical device according to <5> in which the bending operating part includes a housing, and the entire rotating member and the entire second rotating member are housed in the housing.

<7> The medical device according to <5> or (6) in which the second rotating member has a second engaging part that is engaged with the third operating line and the fourth operating line, and the second engaging part is formed in a circular shape or circular-arc shape centered on a rotation center of the second rotating member.

<8> The medical device according to any one of <5> to <7> in which the second operation receiving part is journaled in a rotationally operable manner, the second moving mechanism includes a second pinion provided integrally and coaxially with the second operation receiving part, and a second rack member that is configured to move forward and backward in an interlocking manner with the rotation of the second pinion, and the second rotating member is journaled to the second rack member.

<9> The medical device according to (1) further including a third operating line and a fourth operating line that are inserted in the axial direction of the medical device body, an operation on the bending operating part allowing the third operating line and the fourth operating line to be pulled and allowing the distal end part of the medical device body to be bent in a direction different from a bending direction of the distal end part of the medical device body by the pulling of the first operating line and the second operating line.

<10> The medical device according to <9> in which the bending operating part further includes a second rotating member and a third rotating member that are rotatably journaled, a rotating shaft of the rotating member is coupled to a first coupling region in the third rotating member, the rotating shaft of the second rotating member is coupled to a second coupling region in the third rotating member, a proximal end part of the first operating line and a proximal end part of the second operating line are fixed to the rotating member, a proximal end part of the third operating line and a proximal end part of the fourth operating line are fixed to the second rotating member, as the third rotating member rotates in one direction, the rotating member is pulled and the first operating line and the second operating line are pulled, thereby bending the distal end part of the medical device body, and as the third rotating member rotates in an opposite direction opposite to the one direction, the second rotating member is pulled and the third operating line and the fourth operating line are pulled, thereby bending the distal end part of the medical device body in a direction different from the bending direction of the distal end part of the medical device body by the pulling of the first operating line and the second operating line.

<11> The medical device according to <9> in which the bending operating part includes a second rotating member and a third rotating member that are rotatably journaled, a pinion provided integrally and coaxially with the third rotating member, a first rack member to which a rotating shaft of the rotating member is coupled and which moves forward and backward in an interlocking manner with the rotation of the pinion, and a second rack member to which a rotating shaft of the second rotating member is coupled and which moves forward and backward always in an opposite direction opposite to a forward/backward movement direction of the first rack member in an interlocking manner with the rotation of the pinion, a proximal end part of the first operating line and a proximal end part of the second operating line are fixed to the rotating member, a proximal end part of the third operating line and a proximal end part of the fourth operating line are fixed to the second rotating member, as the third rotating member rotates in one direction, the rotating member is pulled via the first rack member and the first operating line and the second operating line are pulled, thereby bending the distal end part of the medical device body, and as the third rotating member rotates in an opposite direction opposite to the one direction, the second rotating member is pulled via the second rack member and the third operating line and the fourth operating line are pulled, thereby bending the distal end part of the medical device body in a direction different from the bending direction of the distal end part of the medical device body by the pulling of the first operating line and the second operating line.

REFERENCE SIGNS LIST

10: medical device body
11: distal end part
12: intermediate part
13: proximal end part
15: curved region
15a: proximal end position
15b: distal end position
16: parallel region
20: resin tube
21: lumen
22: inner layer
23: outer layer
31: first hollow tube
31a: distal end
32: second hollow tube
32a: distal end
33: third hollow tube
34: fourth hollow tube
41: first operating line
41a: distal end
42: second operating line
42a: distal end
43: third operating line
43a: distal end
44: fourth operating line
44a: distal end
51: braid layer
52: winding wire
60: annular member
61: first annular member
62: second annular member
70: marker
71: first fixing part
72: second fixing part
73: third fixing part
74: fourth fixing part
80: bending operating part
81: rotating member
81a: first fixing par
81b: second fixing part
82: forward/backward movable member (moving mechanism)
82a: holding part
82b: rod-shaped part
82c: rack part
83: pinion (moving mechanism)
84: dial operating part
85: guide
86: housing
90: hub
92: wing part
93: coupling part
100: medical device
110: easily bendable part
111: notched part
180: first bending operating part
181: first rotating members
182: first forward/backward movable member (moving mechanism)
182a: first holding part
182b: first rod-shaped part
182c: first rack part 183: first pinion (moving mechanism)
184: firstdial operating part
185: first guide
191: winding part
192: first coupling wire
193: second coupling wire
194: dial operating part (third rotating member)
195: first coupling region
196: second coupling region
197: pinion
198: first rack member
199: second rack member
200: guide
280: second bending operating part
281: second rotating member
282: second forward/backward movable member (moving mechanism)
282a: second holding part
282b: second rod-shaped part
282c: second rack part
283: second pinion (moving mechanism)
284: second dial operating part
285: second guide

The invention claimed is:

1. A medical device, comprising:
a medical device body having an elongated shape;
a plurality of operating lines comprising a first operating line and a second operating line that are inserted in an axial direction of the medical device body; and
a bending operating device that pulls the first operating line and the second operating line such that a bending operation of a distal end part of the medical device body is performed,
wherein at an intermediate part and a proximal end part in the axial direction of the medical device body, the first operating line and the second operating line extend in parallel such that the first operating line and the second operating line are spaced apart from each other in a circumferential direction of the medical device body, and at the distal end part in the axial direction of the medical device body, the first operating line and the second operating line are gradually curved toward a distal end side and joined together in the circumferential direction of the medical device body such that the first operating line and the second operating line form a curved region and that when the first operating line and the second operating line joined together extend further in parallel to form a parallel region, a distance L1 is equal to or longer than a distance L2 where the distance L1 is measured from a proximal end of the curved region to a distal end of the curved region in the axial direction of the medical device body, and the distance L2 is measured from the distal end of the curved region to distal ends of the first and second operating lines.

2. The medical device according to claim 1, wherein the first operating line and the second operating line are pulled at a time by an operation on the bending operating device.

3. The medical device according to claim 2, further comprising:
a second bending operating device,
wherein the plurality of operating lines further includes a third operating line and a fourth operating line that are inserted in the axial direction of the medical device body, at the intermediate part and the proximal end part in the axial direction of the medical device body, the third operating line and the fourth operating line extend in parallel such that the third operating line and the fourth operating line are spaced apart from each other in the circumferential direction of the medical device body, at the distal end part in the axial direction of the medical device body, the third operating line and the fourth operating line are curved and joined together such that the third operating line and the fourth operating line approach each other in the circumferential direction of the medical device body gradually toward the distal end side, and an operation on the second bending operating device allows the third operating line and the fourth operating line to be pulled and allows the distal end part of the medical device body to be bent in a direction different from a bending direction of the distal end part of the medical device body in the bending operation.

4. The medical device according to claim 3, wherein the second bending operating device includes a first rotating member, a second rotating member, and a third rotating member that are rotatably journaled, the first rotating member has a rotating shaft coupled to a first coupling region in the third rotating member, the second rotating member has a rotating shaft coupled to a second coupling region in the third rotating member, a proximal end part of the first operating line and a proximal end part of the second operating line are fixed to the first rotating member, a proximal end part of the third operating line and a proximal end part of the fourth operating line are fixed to the second rotating member, as the third rotating member rotates in one direction, the first rotating member is pulled and the first operating line and the second operating line are pulled such that the distal end part of the medical device body is bent, and as the third rotating member rotates in an opposite direction opposite to the one direction, the second rotating member is pulled and the third operating line and the fourth operating line are pulled such that the distal end part of the medical device body is bent in a direction different from the bending direction of the distal end part of the medical device body in the bending operation.

5. The medical device according to claim 3, wherein the second bending operating device includes a first rotating member, a second rotating member, and a third rotating member that are rotatably journaled, a pinion provided integrally and coaxially with the third rotating member, a first rack member to which a rotating shaft of the first rotating member is coupled and which moves forward and backward in an interlocking manner with rotation of the pinion, and a second rack member to which a rotating shaft of the second rotating member is coupled and which moves forward and backward always in an opposite direction opposite to a forward/backward movement direction of the first rack member in an interlocking manner with the rotation of the pinion, a proximal end part of the first operating line and a proximal end part of the second operating line are fixed to the first rotating member, a proximal end part of the third operating line and a proximal end part of the fourth operating line are fixed to the second rotating member, as the third rotating member rotates in one direction, the first rotating member is pulled via the first rack member and the first operating line and the second operating line are pulled such that the distal end part of the medical device body is bent, and as the third rotating member rotates in an opposite direction opposite to the one direction, the second rotating member is pulled via the second rack member and the third operating line and the fourth operating line are pulled such that the distal end part of the medical device body is bent in a direction different from the bending direction of the distal end part of the medical device body in the bending operation.

6. The medical device according to claim 1, wherein the distal ends of the first operating line and the second operating line are coupled to each other.

7. The medical device according to claim 6,
wherein the bending operating device includes a rotating member that is rotatably journaled and to which a proximal end part of the first operating line and a proximal end part of the second operating line are fixed, a moving mechanism that moves the rotating member in a pulling direction in which the first operating line and the second operating line are pulled, and an opposite direction opposite to the pulling direction, and an operation receiving part that operates in response to a user's operation, and the rotating member moving in the pulling direction and the opposite direction as power of the operation receiving part is transmitted to the rotating member via the moving mechanism.

8. The medical device according to claim 7, wherein the bending operating device includes a housing, and the rotating member is housed entirely in the housing.

9. The medical device according to claim 7, wherein the rotating member has an engaging part that is engaged with the first operating line and the second operating line, and the engaging part is formed in a circular shape or a circular-arc shape centered on a rotation center of the rotating member.

10. The medical device according to claim 7, wherein the operation receiving part is journaled in a rotationally operable manner, the moving mechanism includes a pinion provided integrally and coaxially with the operation receiving part, and a rack member configured to move forward and backward in an interlocking manner with rotation of the pinion, and the rotating member is journaled to the rack member.

11. The medical device according to claim 7, further comprising:
a second bending operating device,
wherein the plurality of operating lines further comprises a third operating line and a fourth operating line that are inserted in the axial direction of the medical device body, the second bending operating device pulls the third operating line and the fourth operating line such that a second bending operation of the distal end part of the medical device body is performed in a direction different from a bending direction of the distal end part of the medical device body in the bending operation, the second bending operating device includes a second rotating member that is rotatably journaled and to which a proximal end part of the third operating line and a proximal end part of the fourth operating line are fixed, a second moving mechanism that moves the second rotating member in a second pulling direction in which the third operating line and the fourth operating line are pulled, and an opposite direction opposite to the second pulling direction, and a second operation receiving part that operates in response to an operation of the user, and as power of the second operation receiving part is transmitted to the second rotating member via the second moving mechanism, the second rotating member moves in the second pulling direction and the opposite direction opposite to the second pulling direction.

12. The medical device according to claim 11, wherein the bending operating device includes a housing, and the rotating member and the second rotating member are housed entirely in the housing.

13. The medical device according to claim 11, wherein the second rotating member has a second engaging part that is engaged with the third operating line and the fourth operating line, and the second engaging part is formed in a circular shape or a circular-arc shape centered on a rotation center of the second rotating member.

14. The medical device according to claim 11, wherein the second operation receiving part is journaled in a rotationally operable manner, the second moving mechanism includes a second pinion provided integrally and coaxially with the second operation receiving part, and a second rack member configured to move forward and backward in an interlocking manner with rotation of the second pinion, and the second rotating member is journaled to the second rack member.

15. The medical device according to claim 7, wherein the plurality of operating lines further comprises a third operating line and a fourth operating line that are inserted in the axial direction of the medical device body such that an operation on the bending operating device allows the third operating line and the fourth operating line to be pulled and allows the distal end part of the medical device body to be bent in a direction different from a bending direction of the distal end part of the medical device body in the bending operation.

16. The medical device according to claim 15, wherein the bending operating device further includes a second rotating member and a third rotating member that are rotatably journaled, the rotating member has a rotating shaft coupled to a first coupling region in the third rotating member, the second rotating member has a rotating shaft coupled to a second coupling region in the third rotating member, the proximal end part of the first operating line and the proximal end part of the second operating line are fixed to the rotating member, a proximal end part of the third operating line and a proximal end part of the fourth operating line are fixed to the second rotating member, as the third rotating member rotates in one direction, the rotating member is pulled and the first operating line and the second operating line are pulled such that the distal end part of the medical device body is bent, and as the third rotating member rotates in an opposite direction opposite to the one direction, the second rotating member is pulled and the third operating line and the fourth operating line are pulled such that the distal end part of the medical device body is pulled in a direction different from the bending direction of the distal end part of the medical device body in the bending operation.

17. The medical device according to claim 15, wherein the bending operating device includes a second rotating member and a third rotating member that are rotatably journaled, a pinion provided integrally and coaxially with the third rotating member, a first rack member to which a rotating shaft of the rotating member is coupled and which moves forward and backward in an interlocking manner with rotation of the pinion, and a second rack member to which a rotating shaft of the second rotating member is coupled and which moves forward and backward always in an opposite direction opposite to a forward/backward movement direction of the first rack member in the interlocking manner with the rotation of the pinion, the proximal end part of the first operating line and the proximal end part of the second operating line are fixed to the rotating member, a proximal end part of the third operating line and a proximal end part of the fourth operating line are fixed to the second rotating member, as the third rotating member rotates in one direction, the rotating member is pulled via the first rack member and the first operating line and the second operating line are pulled such that the distal end part of the medical device body is bent, and as the third rotating member rotates in an opposite direction opposite to the one direction, the second rotating member is pulled via the second rack member and the third operating line and the fourth operating line are pulled such that the distal end part of the medical device body is bent in a direction different from the bending direction of the distal end part of the medical device body in the bending operation.

18. The medical device according to claim 1, wherein at the intermediate part and the proximal end part in the axial direction of the medical device body, the first operating line and the second operating line are disposed at positions that face each other in the circumferential direction of the medical device body.

19. The medical device according to claim 1, wherein the medical device body comprises a resin tube having a lumen, and a first hollow tube and a second hollow tube that are buried in the resin tube and allow the first operating line and the second operating line to be respectively inserted therethrough, and at the distal end part of the medical device body in the axial direction, the first hollow tube and the second hollow tube are curved such that the first hollow tube and the second hollow tube approach each other in the circumferential direction of the medical device body gradually toward the distal end side.

20. The medical device according to claim 1, wherein the bending operating device comprises a rotating member that is rotatably journaled and is engaged with the first operating line and the second operating line, and to which a proximal end part of the first operating line and a proximal end part of the second operating line are fixed, and a moving mechanism that moves the rotating member in a pulling direction in which the first operating line and the second operating line are pulled, and an opposite direction opposite to the pulling direction.

21. The medical device according to claim 20, wherein the rotating member has an engaging part that is engaged with the first operating line and the second operating line, and the engaging part is formed in a circular shape or a circular-arc shape centered on a rotation center of the rotating member.

22. The medical device according to claim 20, wherein the bending operating device includes an operation receiving part that operates in response to a user's operation, and as power of the operation receiving part is transmitted to the rotating member via the moving mechanism, the rotating member moves in the pulling direction and the opposite direction.

23. The medical device according to claim 22, wherein the operation receiving part is journaled in a rotationally operable manner, the moving mechanism includes a pinion provided integrally and coaxially with the operation receiving part, and a rack member configured to move forward and backward in an interlocking manner with rotation of the pinion, and the rotating member is journaled to the rack member.

24. The medical device according to claim 1, wherein the medical device body has an easily bendable part in which flexibility of the medical device body is locally high such that the easily bendable part is formed in a region between the first operating line and the second operating line in the circumferential direction of the distal end part of the medical device body or a region located opposite to the region between the first operating line and the second operating line with respect to an axis of the medical device body.

25. The medical device according to claim 24, wherein the easily bendable part comprises a notched part formed on an outer surface side of the medical device body.

26. The medical device according to claim 1, wherein the medical device body comprises a resin tube having a lumen, the first operating line and the second operating line are inserted around the lumen of the resin tube, the first operating line and the second operating line are close to each other at a distance smaller than a thickness of the resin tube, at the distal end of the curved region curved such that the first operating line and the second operating line approach each other in the circumferential direction of the medical device body gradually toward the distal end side, and the parallel region where the first operating line and the second operating line extend in parallel close to each other is formed between the distal end of the curved region, and the distal ends of the first operating line and the second operating line.

27. The medical device according to claim 26, wherein the distance L1 from the proximal end of the curved region to the distal end of the curved region is equal to the distance L2 from the distal end of the curved region to the distal ends of the first operating line and the second operating line.

28. The medical device according to claim 26, wherein the distance L1 from the proximal end of the curved region to the distal end of the curved region is longer than the distance L2 from the distal end of the curved region to the distal ends of the first operating line and the second operating line in the axial direction of the medical device body.

29. The medical device according to claim 26, further comprising:
an annular member buried in the resin tube at a distal end part of the curved region,
wherein the annular member has a rigidity higher than a rigidity of the resin tube, and has an external diameter smaller than the thickness of the resin tube, and the first operating line and the second operating line are inserted through the annular member.

30. The medical device according to claim 29, wherein the medical device body comprises a first hollow tube and a second hollow tube that are buried in the resin tube and allow the first operating line and the second operating line to be respectively inserted therethrough, the first hollow tube and the second hollow tube are inserted through the annular member, and in the curved region, the first hollow tube and the second hollow tube are curved such that the first hollow tube and the second hollow tube approach each other in the circumferential direction of the medical device body gradually toward the distal end side.

31. The medical device according to claim 1, further comprising:
a second bending operating device,
wherein the plurality of operating lines further comprises a third operating line and a fourth operating line that are inserted in the axial direction of the medical device body, the second bending operating device pulls the third operating line and the fourth operating line such that a second bending operation of the distal end part of the medical device body is performed in a direction different from a bending direction of the distal end part of the medical device body in the bending operation, at the intermediate part and the proximal end part in the axial direction of the medical device body, the third operating line and the fourth operating line extend in parallel such that the third operating line and the fourth operating line are spaced apart from each other in the circumferential direction of the medical device body, and at the distal end part in the axial direction of the medical device body, the third operating line and the fourth operating line are curved and joined together such that the third operating line and the fourth operating line approach each other in the circumferential direction of the medical device body gradually toward the distal end side.

32. The medical device according to claim 31, wherein the third operating line and the fourth operating line are pulled at a time by an operation on the second bending operating device.

33. The medical device according to claim 31, wherein the second bending operating device comprises a second rotating member that is rotatably journaled and is engaged with the third operating line and the fourth operating line, and to which a proximal end part of the third operating line and a proximal end part of the fourth operating line are fixed, and a second moving mechanism that moves the second rotating member in a second pulling direction in which the third operating line and the fourth operating line are pulled, and an opposite direction opposite to the second pulling direction.

34. The medical device according to claim 33, wherein the second rotating member has a second engaging part engaged with the third operating line and the fourth operating line, and the second engaging part is formed in a circular shape or a circular-arc shape centered on a rotation center of the second rotating member.

35. The medical device according to claim 33, wherein the second bending operating device includes a second operation receiving part that operates in response to a user's operation, and as power of the second operation receiving part is transmitted to the second rotating member via the second moving mechanism, the second rotating member moves in the second pulling direction and the opposite direction opposite to the second pulling direction.

36. The medical device according to claim 35, wherein the second operation receiving part is journaled in a rotationally operable manner, the second moving mechanism includes a second pinion provided integrally and coaxially with the second operation receiving part, and a second rack member configured to move forward and backward in an interlocking manner with rotation of the second pinion, and the second rotating member is journaled to the second rack member.

* * * * *